(12) United States Patent
Shioda et al.

(10) Patent No.: US 6,661,571 B1
(45) Date of Patent: Dec. 9, 2003

(54) SURGICAL MICROSCOPIC SYSTEM

(75) Inventors: Keiji Shioda, Hachioji (JP); Kazuhito Nakanishi, Hachioji (JP); Masakazu Mizoguchi, Tsukui-gun (JP); Masahiko Kinukawa, Sagamihara (JP); Wataru Ohno, Hachioji (JP); Toru Shinmura, Hachioji (JP); Koji Yasunaga, Hino (JP); Takashi Fukaya, Tama (JP)

(73) Assignee: Olympus Optical Co., Ltd., Tokyo (JP)

(*) Notice: Subject to any disclaimer, the term of this patent is extended or adjusted under 35 U.S.C. 154(b) by 0 days.

(21) Appl. No.: 09/663,676

(22) Filed: Sep. 18, 2000

(30) Foreign Application Priority Data

| Sep. 21, 1999 | (JP) | 11-266687 |
| Oct. 8, 1999 | (JP) | 11-288328 |
| Oct. 20, 1999 | (JP) | 11-298250 |
| Nov. 2, 1999 | (JP) | 11-312443 |
| Dec. 13, 1999 | (JP) | 11-353212 |
| Dec. 14, 1999 | (JP) | 11-354414 |

(51) Int. Cl.[7] .................................................. G02B 21/18
(52) U.S. Cl. ........................ 359/372; 359/368; 359/385
(58) Field of Search ............................... 359/368–390; 600/122–132

(56) References Cited

U.S. PATENT DOCUMENTS

| 5,095,887 A | 3/1992 | Leon et al. .................. 128/4 |
| 5,168,863 A | * 12/1992 | Kurtzer ..................... 600/122 |
| 6,081,371 A | * 6/2000 | Shioda et al. ............... 359/372 |

FOREIGN PATENT DOCUMENTS

| JP | 56-176703 | 12/1981 |
| JP | 62-166310 | 7/1987 |
| JP | 03-105305 | 5/1991 |
| JP | 03-200914 | 9/1991 |
| JP | 05-078201 | 10/1993 |
| JP | 06-175033 | 6/1994 |
| JP | 06-205793 | 7/1994 |
| JP | 06-209953 | 8/1994 |
| JP | 07-261094 | 10/1995 |
| JP | 07-281103 | 10/1995 |
| JP | 07-328015 | 12/1995 |
| JP | 09-024052 | 1/1997 |
| JP | 09-056669 | 3/1997 |
| JP | 10-333047 | 12/1998 |
| JP | 11-155798 | 6/1999 |
| JP | 2000-070284 | 3/2000 |
| JP | 2000-139949 | 5/2000 |
| JP | 2000-316873 | 11/2000 |

* cited by examiner

*Primary Examiner*—Thong Nguyen
(74) *Attorney, Agent, or Firm*—Frishauf, Holtz, Goodman & Chick, P.C.

(57) ABSTRACT

Provided is a surgical observational system capable of effectively displaying, in the field of an operating microscope, a real-time image obtained by means of an ultrasonic probe, for example, and a slice image obtained by a preoperative diagnosis on the location of the distal end portion of the probe or a three-dimensional image of an affected region, in association with an actual observational image obtained by means of the microscope. The surgical operation observational system is provided with two monitors in the operating microscope for the observation of the affected region to be operated. Images on the two monitors are alternatively superposed on the optical path of the operating microscope.

19 Claims, 50 Drawing Sheets

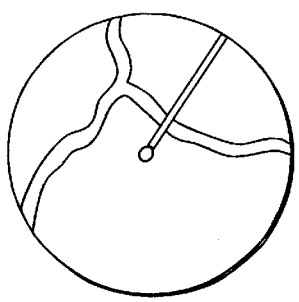
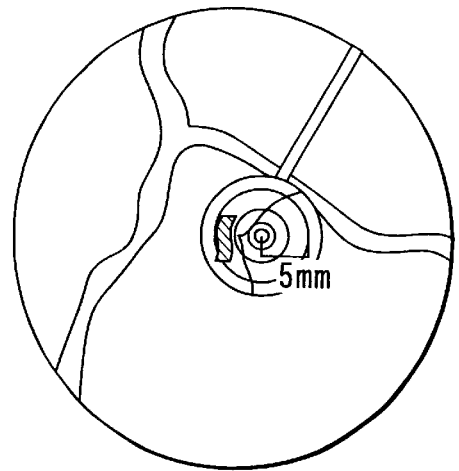
FIG. 6A          FIG. 6B
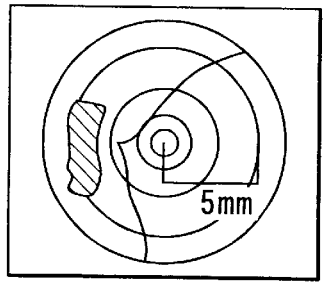
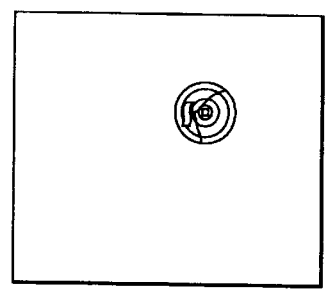
FIG. 7A          FIG. 7B

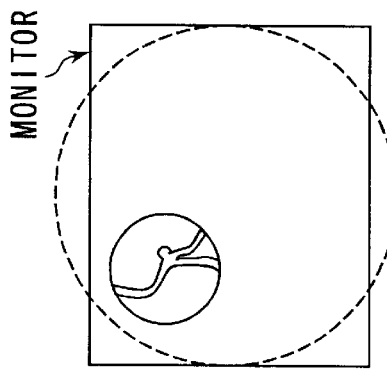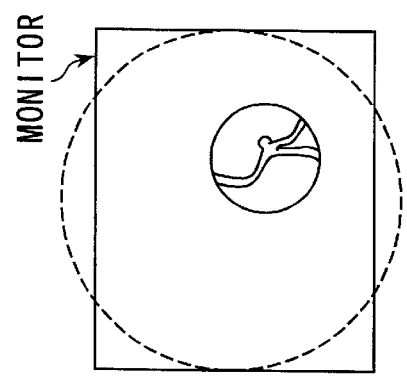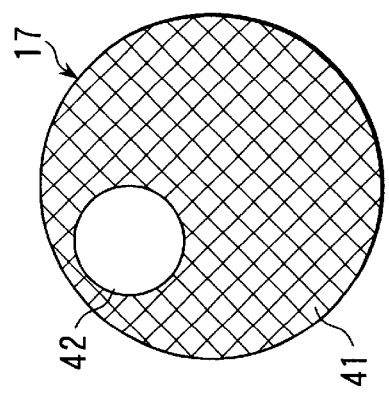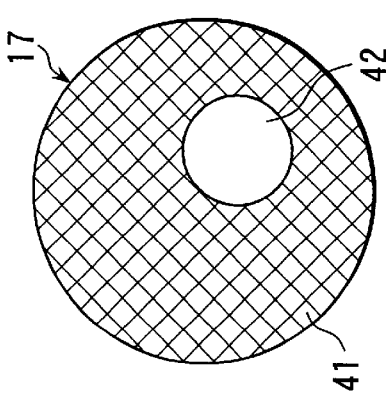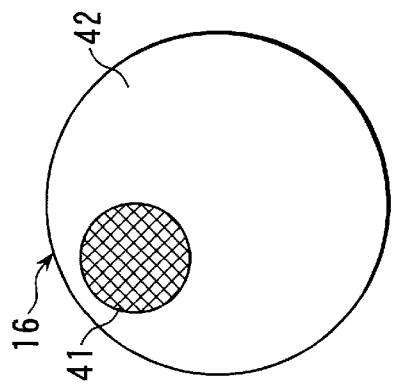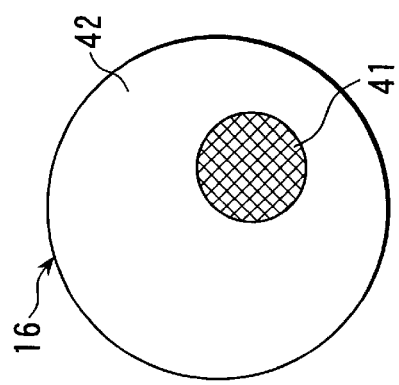

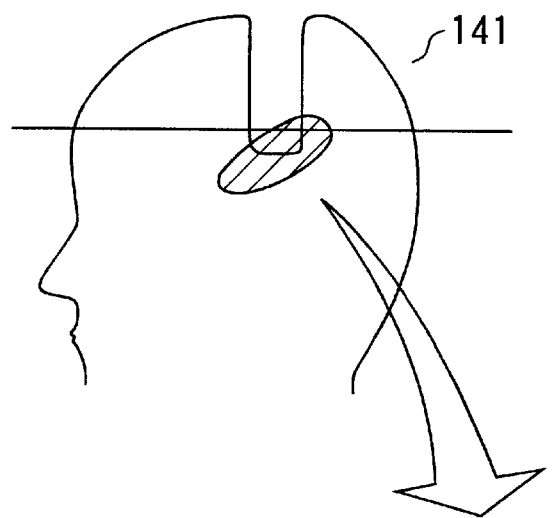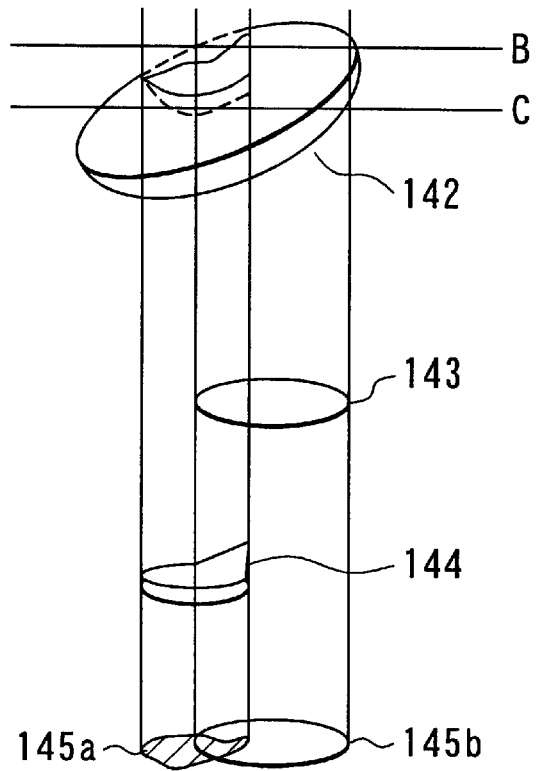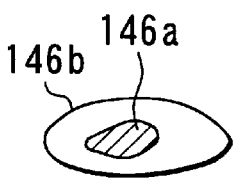
FIG. 21

SURGICAL MICROSCOPIC SYSTEM

CROSS-REFERENCE TO RELATED APPLICATIONS

This application is based upon and claims the benefit of priority from the prior Japanese Patent Applications No. 11-266687, filed Sep. 21, 1999; No. 11-288328, filed Oct. 8, 1999; No. 11-298250, filed Oct. 20, 1999; No. 11-312443, filed Nov. 2, 1999; No. 11-353212, filed Dec. 13, 1999; No. 11-354414, filed Dec. 14, 1999, the entire contents of which are incorporated herein by reference.

BACKGROUND OF THE INVENTION

The present invention relates to a surgical microscopic system adapted for microsurgery carried out under microscopic observation for neurosurgery, for example.

In order to ensure higher accuracy for a neurosurgical operation that uses an operating microscope, for example, treatment based on an endoscope, ultrasonic diagnostic apparatus, or any other diagnostic technique without the use of visible light is expected to be carried out for the tissues of regions that are not accessible to the operating microscope, such as the back or inside of an affected region, accompanied by real-time observation and diagnosis. Various surgical microscopic systems have been developed to meet this requirement.

Described in Jpn. Pat. Appln. KOKAI Publications Nos. 62-166310, 3-105305, 7-261094 are surgical observational systems in which an endoscope or the like is used to observe regions that correspond to dead angles of an operating microscope, and optical images of the observational regions are projected in the field of the microscope.

According to these conventional surgical observational systems, however, an observational image obtained by means of the endoscope or the like is only projected on the microscopic field, so that it is difficult for an operator to identify the endoscopic image that is actually observed through the field of the microscope. In the case where this technique is applied to a diagnostic apparatus, such as an ultrasonic diagnostic apparatus, which uses no visible light, the operator can hardly grasp an actually diagnosed part of a patient's body according to an image in the observational field only. Thus, the operator can discriminate the diagnosed region by the image only if s/he ideally superposes the characteristic features of the diagnostic image and the actual observational image, based on his or her experience.

Described in Jpn. Pat. Appln. KOKAI Publication No. 9-56669, moreover, is a surgical microscopic system with improved operativity, in which an endoscopic image or the like is displayed as a sub-picture in some other part of the microscopic field than the field portion where a main observational image is displayed. If the operator uses the system in combination with an endoscope or ultrasonic observer in this case, however, s/he is not provided with any means for grasping the region that is observed actually. Therefore, the operator can grasp the observational region only by randomly swinging the endoscope or ultrasonic probe in all directions and ideally superposing the characteristic features in comparison with a microscopic image.

Further, a method for guiding second observational means, such as an ultrasonic probe, into the field of an operating microscope is described in Jpn. Pat. Appln. KOKAI Publication No. 6-209953. According to this conventional technique, however, there is provided no method for effectively displaying the observational image of the second observational means in the microscopic field, so that the operator can correlate the microscopic optical image and the image of the second observational means only ideally.

Proposed in Jpn. Pat. Appln. No. 11-132688 filed by the assignee of the present invention (not published), furthermore, is a surgical microscopic system in which the direction of the observational field of an endoscope is indicated by an arrow or the like displayed in the field of a microscope. However, the microscopic optical image and the endoscopic image cannot be satisfactorily correlated by only indicating the observational direction in this manner. Thus, the operator can correlate these images only ideally in consideration of differences in rotation, magnification, etc. between them. If an ultrasonic observer is used as auxiliary observational means, moreover, the observational direction is not fixed, covering the circumferential angle of 360°, for example, so that it is hard to align observational image and an actual affected region.

Described in Jpn. Pat. Appln. KOKAI Publication No. 6-205793, moreover, is a display system that displays a preoperative diagnostic image by superposition on an image of an affected region by means of a half-mirror. Since the preoperative diagnostic image is superposed on the whole affected region image in this case, however, the microscopic field is too obscure to ensure a satisfactory actual surgical operation. Therefore, this system can only determine a preoperative position for craniotomy, and cannot accurately grasp information on the inner tissue in association with the affected region on a real-time basis during the surgical operation.

Described in Jpn. Pat. Appln. KOKAI Publication No. 9-24052, furthermore, is a method that uses fluorescent observation for the recognition of the position of a cerebral tumor, in order to extract the tumor securely under surgical microscopic observation. Although the observational tumor position can be securely recognized by this method, however, the obtained information is related only to the exposed surface of the tumor on the plane of observation at that time (during the extraction). Accordingly, information on the entire tumor (including information on inaccessible depths) inevitably depends on preoperative information.

Further, a navigation apparatus is proposed in Jpn. Pat. Appln. No. 10-248672 (not published). This navigation apparatus forms three-dimensional image data on the basis of image information from a CT scanner or MRI that is operated for a preoperative diagnosis, establishes a spatial correlation between a patient's head and the observational position of a microscope during a surgical operation, and supports the surgical operation in accordance with the three-dimensional image data. According to this navigation apparatus, the image of the entire tumor is obtained as slice image information for the observational point concerned during the surgical operation. However, only the slice image information for a focal position can be obtained on a three-dimensional observational plane of the operating microscope. Therefore, the operator must identify the position of the tumor by the slice image information with the progress of the operation.

With the recent development and spread of microsurgery, a technique for surgical operations for minute affected regions, moreover, operating microscopes have started to be extensively used for microsurgery in a wide variety of fields including ophthalmology, neurosurgery, otolaryngology, etc. Naturally, therefore, the operating microscopes are being improved to meet various requirements that depend on operators' surgical maneuvers. Recently, surgical operations have been changed into less invasive ones in consideration of earlier rehabilitation of operated patients, so that there is a demand for the way of observation of affected regions in finer tubules. For improved accuracy and safety of surgical operations in the depths of the body cavity, furthermore, hidden regions that are inaccessible to microscopic observation are expected to made observable.

As a technique to meet these requirements, a stereoscopic operating microscope described in Jpn. Pat. Appln. KOKAI Publication No. 62-166310, for example, is designed so that the inside of a tubule can be observed by means of first and second stereoscopic optical systems with different base line intervals. Since the two stereoscopic optical systems shares a finder optical system, moreover, an operator can alternatively observe images from the two optical systems. This stereoscopic operating microscope is provided with the stereoscopic optical system that includes the finder optical system and a pair of variable-magnification optical systems, left and right, having the same optical axis. An auxiliary stereoscopic optical system that is located near the main stereoscopic optical system includes image restoring means for reproducing an image from a solid-state image-pickup device for picking up an image of an observed object and image projecting means for guiding the image to the finder optical system of the stereoscopic optical system.

An optical device described in Jpn. Pat. Appln. KOKAI Publications No. 3-105305 is designed so that one or both of images from two observational means of a stereoscopic operating microscope can be alternatively observed and that the operator can select the images by means of a footswitch or the like without using his or her hand.

A system described in Jpn. Pat. Appln. KOKAI Publication No. 6-175033, moreover, is provided with position specifying means for specifying a position in or near the observational field. In this system, the relation between a reference position of an operating microscope and the position specified by means of the position specifying means is computed, and the body of the microscope is moved to the specified position.

Described in Jpn. Pat. Appln. No. 10-319190 filed by the assignee of the present invention (1998, not published), furthermore, is a system provided with drive means that causes an operating microscope and a robot manipulator to move to target positions in accordance with a preoperative diagnostic image or slice image information, thereby correlating the preoperative image and the operative field.

If the operator uses an auxiliary optical system for tubule observation to observe dead-angle regions that are inaccessible to microscopic observation, e.g., the back side of the an aneurysm, nerves cleared of a tumor, peripheral tissues, etc., as in the prior art case mentioned before, a video image picked up by means of an endoscope or other auxiliary optical system is displayed in the microscopic field. In this case, the operator's mate sometimes may observe a similar image as s/he aspirates the marrow or blood to secure the operator's field of vision.

FIGS. 74 shows an example of the system of an operating microscope a of this type. A body b of the microscope a is provided with an operator eyepiece unit c1 and a mate eyepiece unit c2. An in-field monitor (not shown) is located in a part of the field of each of the eyepiece units c1 and c2. As shown in FIGS. 75A and 75B, indexes and sub-images e1 and e2 that are different from main images d1 and d2 of the operating microscope a are projected in the main images d1 and d2.

An LCD driver f is connected to each in-field monitor. Further, a CCTV unit g is connected to the LCD driver f. A camera head i is connected to the CCTV unit q. An endoscopic image observed by means of an endoscope h is displayed on the respective in-field monitors of the operator and mate eyepiece units c1 and c2.

When a conventional operating microscope apparatus is used, moreover, an operative field j as an object of a surgical operation is observed at different angles by means of the microscope body b and the endoscope h. An optical video image then caught by the endoscope h is photoelectrically converted by means of a image-pickup device (not shown) in the TV camera head i and applied as an electrical signal to the TV camera head i to be processed therein, whereupon a TV signal is outputted. This TV signal is converted into a display mode signal of a liquid crystal display device (not shown) by means of the LCD driver f. This signal is delivered to liquid crystal image display devices (not shown) of the respective in-field monitors of the operator and mate eyepiece units c1 and c2 of the microscope a. Thereupon, endoscopic images are partially displayed as the sub-images e1 and e2 on the main images d1 and d2 of the microscope a in the microscopic field, as shown in FIGS. 75A and 75B. More specifically, in the operator eyepiece unit c1 of this operating microscope apparatus, the sub-image e1, an endoscopic image, is inserted into the main image d1 in the field of the microscope a by means of the liquid crystal image display device (not shown), as shown in FIG. 75A. Likewise, in the mate eyepiece unit c2, the sub-image e2, an endoscopic image, is inserted into the main image d2 in the field of the microscope a by means of the liquid crystal image display device (not shown), as shown in FIG. 75B.

According to this operating microscope apparatus, however, the operator and the mate have their respective observational directions. Therefore, the relation between the display position of the main image d1 in the field of the operator eyepiece unit c1 of the microscope a and the display position of the sub-image e1 in the same field is different from the relation between the display position of the main image d2 in the field of the mate eyepiece unit c2 of the microscope a and the display position of the sub-image e2 in the same field. Since the field direction of the mate is different from that of the operator, the position in the mate-side observational optical system where the in-field display image appears is inevitably different from the corresponding position in the operator-side observational optical system. Possibly, therefore, a region that can be observed through the operator-side optical system may not be able to be observed through the mate-side optical system.

Basically, moreover, the field direction on the mate side is different from the operator-side field direction. Although the microscope images are located in correct relative positions, therefore, the positional relation between the images obtained by means of the auxiliary optical system cannot be displayed correctly. Since the mate-side observational optical system is rotatable with respect to the operator-side system, furthermore, the positional relation between the images of the auxiliary optical system goes wrong if the mate-side system is rotated. If bleeding or the like occurs in any region corresponding to a dead angle of the image of the auxiliary optical system in the mate-side field, therefore, the display position of the auxiliary optical system must be controlled manually.

In carrying out a surgical operation with reference to a diagnostic image, furthermore, a preoperative diagnostic image, such as MRI or X-ray CT, sometimes may be display as each of the sub-images e1 and e2 on the video images in the main images d1 and d2 in the field of the microscope a. In this case, these sub-images, unlike the aforesaid video image of the auxiliary optical system, should never fail to be erect images, and the images that are accessible to the operator and the mate, individually, must be of the same type.

In the case where the operating microscope apparatus is used in combination with a position information detector or the like, moreover, a position information detection image and a marker for the detector must be overlaid on a microscopic image. A conventional microscopic apparatus with in-field display means requires use of one combination of an optical system and a display device for the display of an image in the microscopic field and another for the display of a marker. If the image and the marker are needed simultaneously, therefore, the display device must be changed during use or one of the devices must be replaced with an alternative device.

Conventionally, furthermore, the operator is expected to confirm the marker display of the position information detector and manually move the microscope body to the marker position. Accordingly, highly complicated maneuvers are required by a technique that uses the position information detector in combination with an auxiliary optical system such as an endoscope.

In order to make a microsurgical operation less invasive, moreover, various pieces of image information are used during the operation. The image information may be obtained by means of an endoscope for observing regions that are inaccessible to the operating microscope or an ultrasonic observer for obtaining a slice image of the inside of tissue. Further, it may be obtained by means of a diagnostic device such as a so-called nerve monitor device for measuring the potential of nerves of a patient under the operation. To attain this, an operating microscope for the observation of an endoscopic image or the like is described in Jpn. Pat. Appln. KOKAI Publication No. 10-333047, as in Jpn. Pat. Appln. KOKAI Publication No. 62-166310.

A microscope requires visibility adjustment or adjustment of differences in eyesight (refractive force) between observers. A technique for this visibility adjustment is described in Jpn. Pat. Appln. KOKAI Publication No. 7-281103. An operating microscope is also subjected to the visibility adjustment with every surgical operation. On the other hand, a method for measuring the refractive force of an eye is described in Jpn. Pat. Appln. KOKAI Publication No. 3-200914. In this method, however, the refractive force of an eye of a patient, not an observer, is measured by projecting an index on the eyeground and detecting light reflected by the eyeground.

The operating microscope described in Jpn. Pat. Appln. KOKAI Publication No. 10-333047 can perform microscopic observation and endoscopic observation in one and the same field. When an endoscope is moved in an affected region, however, its distal end must be checked for the location on a microscopic image lest it damage tissue as an endoscopic image is observed. It is to be desired, therefore, that the endoscopic image should not intercept the microscopic field or should be displayed small on the microscopic image.

When the endoscopic image is watched as a treatment or the like is carried out, on the other hand, it is expected to be wide enough. Observation based on the microscopic image is also needed to check an instrument for insertion or watch a wide range of the affected region. Thus, it is advisable to display the endoscopic image large on the microscopic image.

In each of the operating microscopes described in Jpn. Pat. Appln. KOKAI Publications Nos. 62-166310 and 10-333047, however, the endoscopic image is displayed in a fixed position and within a fixed range in the microscopic field. Therefore, a surgical operation using the endoscope cannot easily meet the demand for both the movement of the endoscope and the treatment with reference to the endoscopic image, and the endoscopic image may be obstructive or too small for smooth treatment.

Thus, it is hard for an operator to concentrate his or her attention on the surgical operation, so that the operator's fatigue increases, and the operation time extends. An ultrasonic diagnostic apparatus is subject to the same problems when its probe is moved or when ultrasonic observation or treatment under ultrasonic observation is carried out. Since the endoscope used under surgical microscopic observation is designed for the observation of regions corresponding to dead angles of the microscope, moreover, it should be of a squint type for observation in directions different from the direction of its insertion. If the squint-type endoscope is rotated around the direction of insertion, it ceases to be able to identify the direction of view with respect to the microscopic field. Accordingly, the operator must judge the observational direction by a tissue form displayed in the endoscopic image. Thus, it is hard for the operator to be devoted to the surgical operation, so that the operator's fatigue increases, and the operation time extends. Even when the operator is concentrating his or her attention on the observational image of the operating microscope, furthermore, s/he must also pay attention to the state of some other equipment to detect a change in the nerve monitor device, so that his or her fatigue is increased.

On the other hand, the conventional visibility adjustment operation described in Jpn. Pat. Appln. KOKAI Publication No. 7-281103 is troublesome and lengthens the setup time before the start of operation of the operating microscope. If the operator changes during a surgical operation, moreover, the visibility must be readjusted. Usually, it is difficult to adjust the visibility with a drape for sterilization on the microscope. If the microscope is used with wrong visibility, the surgical operation is performed with the right or left eye of the operator out of focus, so that the operator is fatigued much. Further, a TV camera or 35-mm camera that is connected to the operating microscope may fail to be in focus. In this case, the refractive index of the operator's eye may be able to be measured automatically to correct the visibility by the method described in Jpn. Pat. Appln. KOKAI Publication No. 3-200914. According to this method, however, an optical system must be provided with an index projection optical system for detection and its mating light receiving optical system, so that a large-sized apparatus is required, constituting a hindrance to the surgical operation. Even if projected light has a wavelength in an invisible zone, its influence upon the observational performance of the microscope cannot be removed thoroughly, so that the efficiency of the surgical operation is lowered, and the operator is fatigued inevitably.

A rigid scope may be used for the observation of regions corresponding to dead angles of the operating microscope in microsurgery. In this case, the observation of the dead-angle regions requires use of a so-called squint-type rigid scope for oblique observation at a fixed angle (e.g., 30°, 70° or 110°) to the observational optical axis of its eyepiece. In this rigid scope, a TV camera (image-pickup device) is connected to the eyepiece to display its observational image on a monitor screen. The rigid scope is also connected with a light guide, which is connected to a light source unit to guide illumination light to an affected region. In order to observe a region corresponding to a dead angle of the operating microscope, the rigid scope of this type is used in a very narrow space (normally about 300 mm) between the body of the microscope and the observational region. To change its squint angle, moreover, the rigid scope can be rotated throughout the angular range of 360° with respect to the direction of its insertion during a surgical operation. Thus, the operator can observe his or her desired position.

In a rigid scope described in Jpn. UM Appln. KOKAI Publication No. 5-78201, a TV camera is connected optically to the imaging point of its eyepiece. A light guide that constitutes an illumination optical system in the rigid scope and a light guide one end of which is connected to a light source unit are connected optically to each other in a position near the eyepiece. Since the TV camera itself projects in the direction of insertion of the rigid scope, however, it may possibly interfere with the operating microscope body, depending on the direction of insertion of the scope into the body cavity, so that the operator's desired observational position is restricted inevitably. Further, the light guide that is connected to the light source unit projects substantially at right angles to the direction of insertion into the body cavity. If the operator rotates the rigid scope around the direction of insertion to change the observational direction, therefore, the light guide may get deep into the field of the microscope depending on its direction, thereby hindering the microscopic observation.

In a rigid scope described in U.S. Pat. No. 5,168,863, moreover, cables of a TV camera that is connected to an eyepiece are guided in a direction at about 45° to its longitudinal direction (direction of insertion into the body cavity). In this case, the TV camera can somewhat be prevented from interfering with the body of an operating microscope. Nevertheless, the TV camera itself still causes interference, and the light guide extensively intercepts the microscopic field as the rigid scope rotates.

In a rigid scope described in Jpn. UM Appln. KOKAI Publication No. 56-176703, furthermore, a reflective member for bending the observational optical axis is disposed on an observational optical system therein so that the optical axis of an eyepiece is inclined at a fixed angle to the longitudinal direction of the scope (direction of insertion into the body cavity). Since the a part of the eyepiece portion of this rigid scope is inclined at the fixed angle to the direction of insertion of the scope, a TV camera can avoid interfering with the body of an operating microscope. Since the direction of projection of a light guide is coincident with the direction of insertion into the body cavity, however, the light guide and the microscope body inevitably interfere with each other.

A rigid scope described in Jpn. Pat. Appln. KOKAI Publication No. 11-155798, like the one described in Jpn. UM Appln. KOKAI Publication No. 56-176703, is designed so that the observational optical axis of an eyepiece is inclined at a fixed angle to its longitudinal direction (direction of insertion into the body cavity), and a light guide, which is connected to a light source unit, is connectable near the eyepiece. In either of the rigid scopes described in Jpn. UM Appln. KOKAI Publication No. 56-176703 and Jpn. Pat. Appln. KOKAI Publication No. 11-155798, however, the eyepiece and the TV cam attached thereto project long within a plane at about 90° to the direction of insertion of the rigid scope into the body cavity (i.e., region for the operator's surgical operation), so that they inevitably intercept the space for the surgical operation, thereby hindering the operation. When the operator rotates the rigid scope around the direction of insertion into the body cavity to change the observational direction, in particular, the scope moves in an arc of a circle having a radius that is equal to the sum of the respective overall lengths of the eyepiece, TV camera, cables, etc., thus constituting a great hindrance to the operation. Depending on the observational direction, moreover, the TV camera and the light guide may interfere with the operator's hand or body, so that they may possibly lower the efficiency of the surgical operation.

BRIEF SUMMARY OF THE INVENTION

The present invention has been contrived in consideration of these circumstances.

An object of the present invention is to improve the efficiency of a surgical operation by simultaneously displaying a plurality of pieces of information required by an operator in the field of a microscope during microsurgery so that the operator can be fed with necessary information as required.

Another object of the invention is to display a real-time observational image of second observational means effectively in association with an observational image of first observational means in the field of the first observational means in a microscope body.

Still another object of the invention is to provide a surgical microscopic system designed so that an operator can easily grasp the progress of an surgical operation during the operation, whereby the operation can be carried out more securely and safely.

A further object of the invention is to provide a surgical microscopic system designed so that necessary in-field information can be appropriately offered to an operator or his or her mate, and that a required microscopic field can be easily secured during a surgical operation.

An additional object of the invention is to provide a surgical microscopic system designed so that an operator can be devoted to a surgical operation, his or her fatigue can be eased, and the operation time can be shortened.

Furthermore, the invention is intended to improve a rigid scope that can be inserted into the body cavity under surgical microscopic observation, thereby enabling observation at a fixed angle to the direction of insertion, to prevent the rigid scope and a TV camera or light guides connected thereto from hindering the microscopic observation or surgical treatment, and to enable an operator to observe a desired position with ease.

In order to achieve the above objects, according to an aspect of the invention, there is provided an operating microscope apparatus comprising: at least one microscope body defining an observational field for observing an affected region; first image display means for displaying a first image in the observational field; second image display means for displaying a second image in the observational field; and image display control means for displaying independent images on the first and second image display means, individually.

The microscope body may include an optical image displayed in the observational field. In this case, the operating microscope apparatus may comprise second observational means different from an operating microscope and selected from a group including an endoscope and an ultrasonic probe. Further, the second image display means may include an image superposition optical system for superposing an image on the optical image in the observational field. Preferably, the image display control means includes means for independently switching on and off the first and second image display means.

In the case where the operating microscope apparatus comprises second observational means different from an operating microscope and selected from a group including an endoscope and an ultrasonic probe, the first and second images preferably include (i) a combination of an observational image obtained by means of the second observational means and an image (navigation image) indicative of the observational position or direction of the second observational means or (ii) a combination of a tumor position display marker image and a preoperative/mid-operative diagnostic image selected from a group including image-processed fluorescent observational images and the image (navigation image) indicative of the observational position or direction of the second observational means.

According to another aspect of the invention, there is provided a surgical observational system including first observational means for observing an affected region and second observational means different from the first observational means at least in the observational direction or observational method. This system comprises detecting means for detecting the respective observational positions and directions of the first and second observational means relative to the position of the affected region; and display means for displaying an observational image of the second observational means in a given part of an observational image of the first observational means in visual correlation based on the relative positions detected by means of the detecting means. According to this surgical observational system, the image of the second observational means is correlatively displayed in a part of the observational image of the first observational means. Thus, the respective observational positions of the first and second observational means are detected on the basis of the affected region by means of an optical position detector, for example. The observational image of a corresponding portion of the second observational means can be cut out into a given position of the observational image of the first observational means to adjust the image size for display.

Alternatively, the surgical observational system may comprise detecting means for previously storing a preoperative diagnostic image and detecting the observational position of the second observational means relative to the preoperative diagnostic image; and display means for simultaneously displaying the preoperative diagnostic image concurrent with the observational position of the second observational means and the observational image of the second observational means in the field of the first observational means in accordance with the relative positions detected by means of the detecting means. In this case, the observational position of the second observational means is detected on the basis of the affected region by means of an optical position detector, for example. The observational image of the second observational means is displayed in the field of the observational image of the first observational means, and at the same time, a part of the preoperative diagnostic image corresponding to the observational position of the second observational means is displayed in the observational field of the first observational means.

According to this surgical observational system, at least a part of the observational image of the second observational means is displayed in the observational field of the first observational means for the observation of the affected region in a manner such that its position, size, etc. are associated with those of the observational field of the first observational means. Accordingly, the states of dead angle portions and the inside of tissue that cannot be observed by means of the first observational means can be recognized easily and securely, so that the reliability and efficiency of the surgical operation can be improved considerably.

On the other hand, the surgical observational system may comprise detecting means for detecting the respective observational positions and directions of the first and second observational means relative to the position of the affected region; an indicator indicative of an optional position in the observational field of the first observational means; and display means capable of following the indicator and displaying an observational image for a given range in the observational field of the first observational means by superposition. According to this surgical observational system, as in the case of the system described above, the image of the second observational means can be correlatively displayed in a part of the observational image of the first observational means. An operator can operate the indicator to set an optional position in the observational field of the first observational means. The observational image of the second observational means is displayed in a given range of the indicator after is cut out and subjected to size adjustment. Thus, the affected region in the peripheral portion and the observational image of the second observational means can be correlated with ease, and treatment can be carried out smoothly, so that the efficiency of the surgical operation can be improved.

According to still another aspect of the invention, there is provided an operating microscope apparatus for subjecting an affected region to a surgical operation, comprising: a microscope body including a stereoscopic optical system and used to observe a desired region; position computing means for detecting the position of the observational region observed through the stereoscopic optical system and computing the positional relation between the observational region and a diagnostic image of the affected region; fluorescent shooting means for shooting fluorescent images of the observational region, thereby obtaining fluorescent observational images; and display means for displaying, by superposition, the diagnostic image corresponding to the position of the observational region detected by means of the position computing means and the fluorescent observational images obtained by means of the fluorescent shooting means.

This operating microscope apparatus may comprise storage means for storing the fluorescent observational images. In this case, the display means displays the diagnostic image corresponding to the observational position detected by means of the position computing means and the fluorescent observational images stored in the storage means, by superposition on the observational image of the affected region. Further, the operating microscope apparatus may comprise display mode setting means capable of setting an optional display mode. In this case, the display means displays the diagnostic image corresponding to the observational position detected by means of the position computing means and the fluorescent observational images stored in the storage means, by superposition on the observational image of the affected region, in accordance with the setup state of the display mode setting means.

According to this operating microscope apparatus, the fluorescent observational images shot by means of the fluorescent shooting means and the diagnostic image selected according to the observational position detected by means of the position computing means are displayed by superposition, so that the operator can accurately recognize the conditions of a tumor to be extracted. Thus, the operator can carry out extraction more accurately and be devoted to the extracting operation. Further, only the tumor portion can be extracted securely, so that the object for minimally invasive surgery can be achieved.

According to the present invention, moreover, there is provided an operating microscope apparatus for subjecting an affected region to a surgical operation, comprising: a microscope body including a stereoscopic optical system and used to observe a desired region; position computing means for detecting the position of the observational region observed through the stereoscopic optical system and computing the positional relation between the observational region and a diagnostic image of the affected region; fluorescent shooting means for stereoscopically shooting fluorescent images of the observational region, thereby obtaining fluorescent observational images; storage means for storing the fluorescent observational images; image dividing means for dividing the diagnostic image corresponding to the observational position detected by means of the position computing means into two image signals having a lateral parallax; and display means for displaying the individual stored fluorescent observational images and the laterally divided diagnostic images by superposition on the observational image of the affected region.

Likewise, there is provided an operating microscope apparatus for subjecting an affected region to a surgical operation, comprising: a microscope body including a stereoscopic optical system and used to observe a desired region; position computing means for detecting the position of the observational region observed through the stereoscopic optical system and computing the positional relation between the observational region and a diagnostic image of the affected region; fluorescent shooting means for stereoscopically shooting fluorescent images of the microscopic observational region, thereby obtaining fluorescent observational images; storage means for storing the fluorescent observational images; display mode setting means capable of setting an optional display mode; image dividing means for dividing the diagnostic image corresponding to the observational position detected by means of the position computing means into two image signals having a lateral parallax; superposing means for superposing the individual stored fluorescent observational images and the laterally divided diagnostic images on the observational image of the affected region in accordance with the setup state of the display mode setting means; and a lens tube portion having a monitor portion for displaying the individual images.

The fluorescent shooting means may be designed for stereoscopic shooting of the fluorescent images of the observational region. In this case, the operating microscope apparatus comprises image dividing means for dividing the diagnostic image corresponding to the observational position detected by means of the position computing means into two image signals having a lateral parallax. The display means can display the individual stored fluorescent observational images and the laterally divided diagnostic images by superposition on the observational image of the affected region.

Further, the operating microscope apparatus may comprise a lens tube portion having a monitor portion for displaying the individual images.

Furthermore, the display means may be designed to display, by superposition, the slice image corresponding to the observational position detected by means of the position computing means and the fluorescent observational images obtained by means of the fluorescent shooting means. This operating microscope apparatus may comprise display mode setting means capable of setting an optional display mode. In this case, the display means displays the slice image corresponding to the observational position detected by means of the position computing means and the fluorescent observational images stored in the storage means, by superposition on the observational image of the affected region, in accordance with the setup state of the display mode setting means.

According to a further aspect of the invention, there is provided an operating microscope apparatus including a plurality of eyepiece units capable of relative movement and individually having fields capable of displaying one and the same region as a main image and in-field monitors provided individually for the eyepiece units and each adapted to project an index and/or a sub-image different from the main image on a part of the field, comprising: input means for applying observation conditions to one of the eyepiece units; and observational state changing means for changing the observational state of the other eyepiece unit according to the conditions. Thus, necessary in-field information can be appropriately offered to the operator or his or her mate, and a target microscopic field can be easily secured during a surgical operation. Preferably, the observational state changing means includes detecting means for detecting the position of the one eyepiece unit relative to the other eyepiece unit, an in-field display control means for controlling the display position of the in-field monitor of at least the one eyepiece unit to change the observational region in accordance with the result of detection by the detecting means, shielding means for selectively intercepting the optical image of the eyepiece units, and image rotating means for rotating the image of the in-field monitor in response to the output of the position detecting means. In this case, an optimum image display method can be provided even for a fixed-direction image, such as a preoperative image, and overlay display of the index by means of a position information detector and the operation of the detector can be carried out with ease. Further, the display method can secure a satisfactory degree of freedom for the operator and the mate.

The sub-image may be a diagnostic image. Preferably, in this case, the operating microscope apparatus comprises index manipulating means for changing the in-field index position on the diagnostic image and a position information computing unit for computing the three-dimensional position of an actual affected region relative to the position of the index displayed by means of the index manipulating means, and the position information computing unit and the in-field display control means drive the observational region of the operating microscope to the three-dimensional position.

Preferably, the operating microscope apparatus further comprises an image processing unit for image map conversion, adapted synchronously to rotate the image of the in-field monitor and the shielding means formed of the liquid crystal device in response to the output of the relative position detecting means.

According to an additional aspect of the invention, there is provided an operating microscope comprising: a first observational optical system for optically enlarging an affected region; a second observational optical system for observing optional image information from an external apparatus; and an eyepiece optical system for simultaneously observing observational images of the first and second observational optical systems, the second optical system including display state changing means capable of changing the display state of the image information from the external apparatus in accordance with operation information from the external apparatus. The first and second observational optical systems are different from each other.

According to this operating microscope, if the operating state of the external apparatus is changed when the observational images of the first and second observational optical systems are simultaneously displayed, the image observed by means of the second observational means is automatically changed into a suitable state for a surgical operation. A small endoscopic image is displayed when an endoscope is moved in the affected region, for example. The displayed endoscopic image is large enough when it is watched as treatment or the like is carried out. Thus, according to this operating microscope, the display state of the display image in the microscopic field can be automatically changed in accordance with the operating state of the external apparatus, so that the operator can be devoted to the surgical operation, his or her fatigue can be eased, and the operation time can be shortened. This microscope is particularly serviceable if it is used with an ultrasonic observer for obtaining a slice image of the inside of tissue or a so-called nerve monitor device for measuring the potential of nerves of a patient under the operation, as well as the endoscope for observing regions that are inaccessible to the operating microscope.

Further, there is provided an operating microscope comprising: a first observational optical system for enlarged-scale optical observation of an affected region; a second observational optical system for observing optional image information from an external apparatus, the second observational optical system being different from the first observational optical system, and an eyepiece optical system for simultaneously observing observational images of the first and second observational optical systems. The second optical system includes fixed-view image display means for an observer's close observation, an index projection optical system for the eyeground, and an image receiving optical system for receiving reflected light from the eyeground. The operating microscope further comprises detecting means for computing refractive force in accordance with information from the image receiving optical system and visibility adjustment drive control means for driving a visibility adjustment mechanism in accordance with information from the detecting means. According to this operating microscope, the sight or refractive force of an observing eye is measured through the second observational optical system. Based on this refractive force, the visibility adjustment drive control means automatically carries out visibility adjustment. Thus, the operating microscope can be reduced in size without lowering its observational performance, and the operator can concentrate his or her attention on the operation without fatigue.

The display state changing means may include operation input portion for inputting the operation information from the external apparatus, optical changing means capable of optically changing the display state of the image information of the second observational optical system compared to the observational image of the first observational optical system, and control means for actuating the optical changing means in accordance with input information from the operation input portion. Preferably, the optical changing means includes magnification changing means capable of changing the magnification of the second observational optical system. According to this operating microscope, the size of each endoscopic image in the microscopic field can be changed in accordance with the movement and observational state of the endoscope. Thus, when the endoscope is moved, a small endoscopic image is displayed such that the distal end of the endoscope can be satisfactorily observed through the microscope. During endoscopic observation, on the other hand, a large image is displayed to facilitate treatment. If a squint-type endoscope for observation in directions different from the direction of insertion is used and rotated around the direction of insertion to observe regions corresponding to dead angles of the microscope, therefore, the observational direction of the endoscope compared to the microscopic field can be identified with ease.

Preferably, the optical changing means includes magnification changing means capable of changing the magnification of the second observational optical system or display position changing means capable of changing the position of the second observational optical system relative to the first observational optical system. The magnification changing means may be lens moving means for moving a variable-magnification optical system constituting the second observational optical system. Thus, there is provided an operating microscope in which the observational direction of an endoscope compared to the microscopic image can be recognized with ease.

The display position changing means may include rotating means for rotating the second observational means around the optical axis of the first observational means. Even when the operator is concentrating his or her attention on the observational image of the operating microscope, in this case, s/he can readily notice a change in the nerve monitor device. Thus, the operator can be devoted to the surgical operation, and his or her fatigue can be eased.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 6A and 6B are views individually showing images observed by an operator, in which FIG. 6A shows only an optical image obtained when the whole surface of the first liquid crystal shutter is transmittable, and FIG. 6B shows a state in which an image obtained by means of an ultrasonic probe is displayed in a microscopic field;

FIG. 7A is a view showing an image obtained by means of the ultrasonic probe and displayed on a monitor;

FIG. 7B is a view showing a state in which the image obtained by means of the ultrasonic probe is reduced to a given size;

FIGS. 10A to 10C are views individually showing various states of an image in the microscopic field observed by the operator, in which FIG. 10A shows an ultrasonic image obtained by means of the ultrasonic probe, FIG. 10B shows a preoperative diagnostic image, and FIG. 10C shows the preoperative diagnostic image and the ultrasonic diagnostic image in association with an actual affected region;

FIGS. 11A and 11B are views individually showing observational images according to the second embodiment, in which FIG. 11A shows the ultrasonic probe having its central portion extracted by means of a mixer, and FIG. 11B shows an image actually observed by the operator;

FIGS. 14A to 14F illustrate the respective operations of first and second liquid crystal shutters according to the third embodiment, in which FIGS. 14A and 14B are views showing the relation between a shading portion and a transparent portion, FIG. 14C is a view showing a state of display on a monitor, and FIGS. 14D to 14F are views similar to FIGS. 14A to 14C, showing the shading portion and the transparent portion shifted in position;

FIG. 21 is a view for illustrating the way of synthesizing a fluorescent observational image and a two-dimensional preoperative slice image;

DETAILED DESCRIPTION OF THE INVENTION

First Embodiment

A first embodiment of the present invention will now be described in detail with reference to the accompanying drawings.

Figure 1:
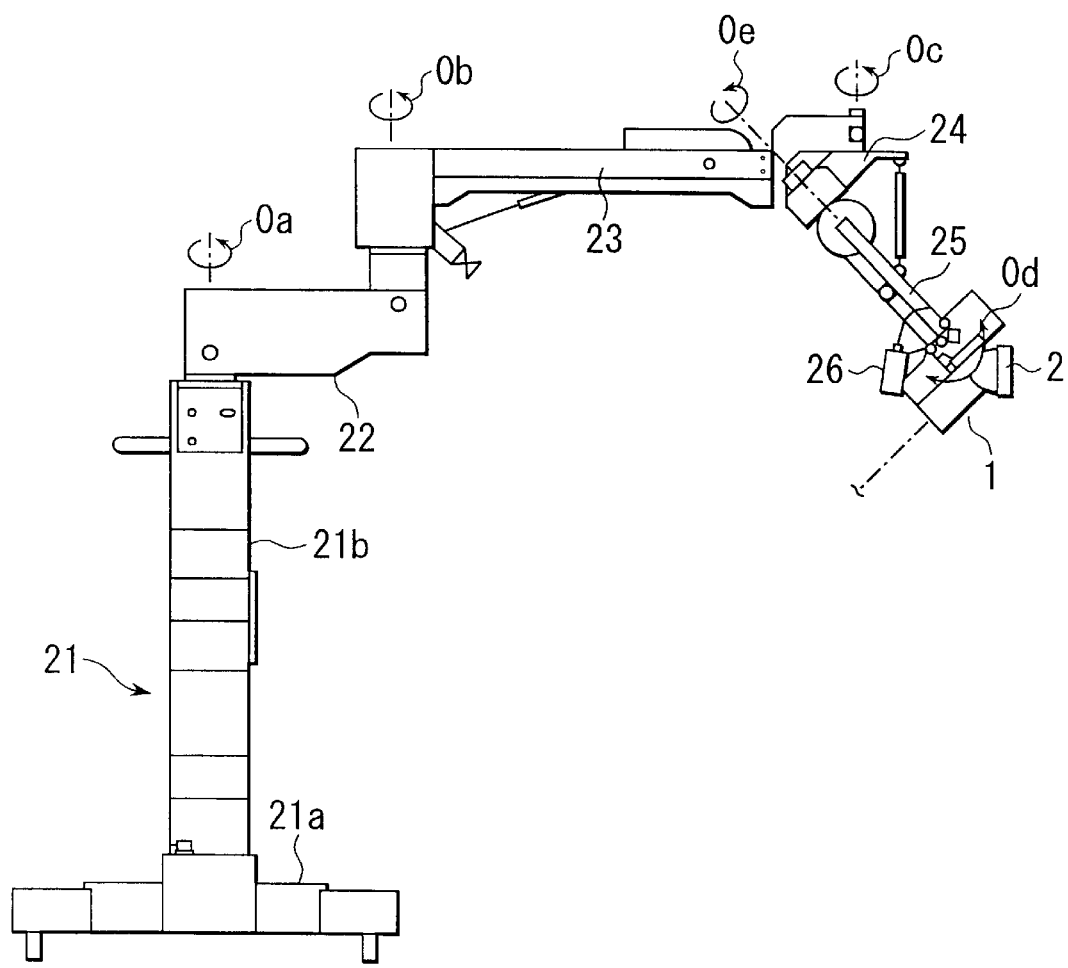
FIG. 1 is a view showing an outline of an operating microscope for use as first observational means of a surgical observational system according to a first embodiment.
Figure 2:
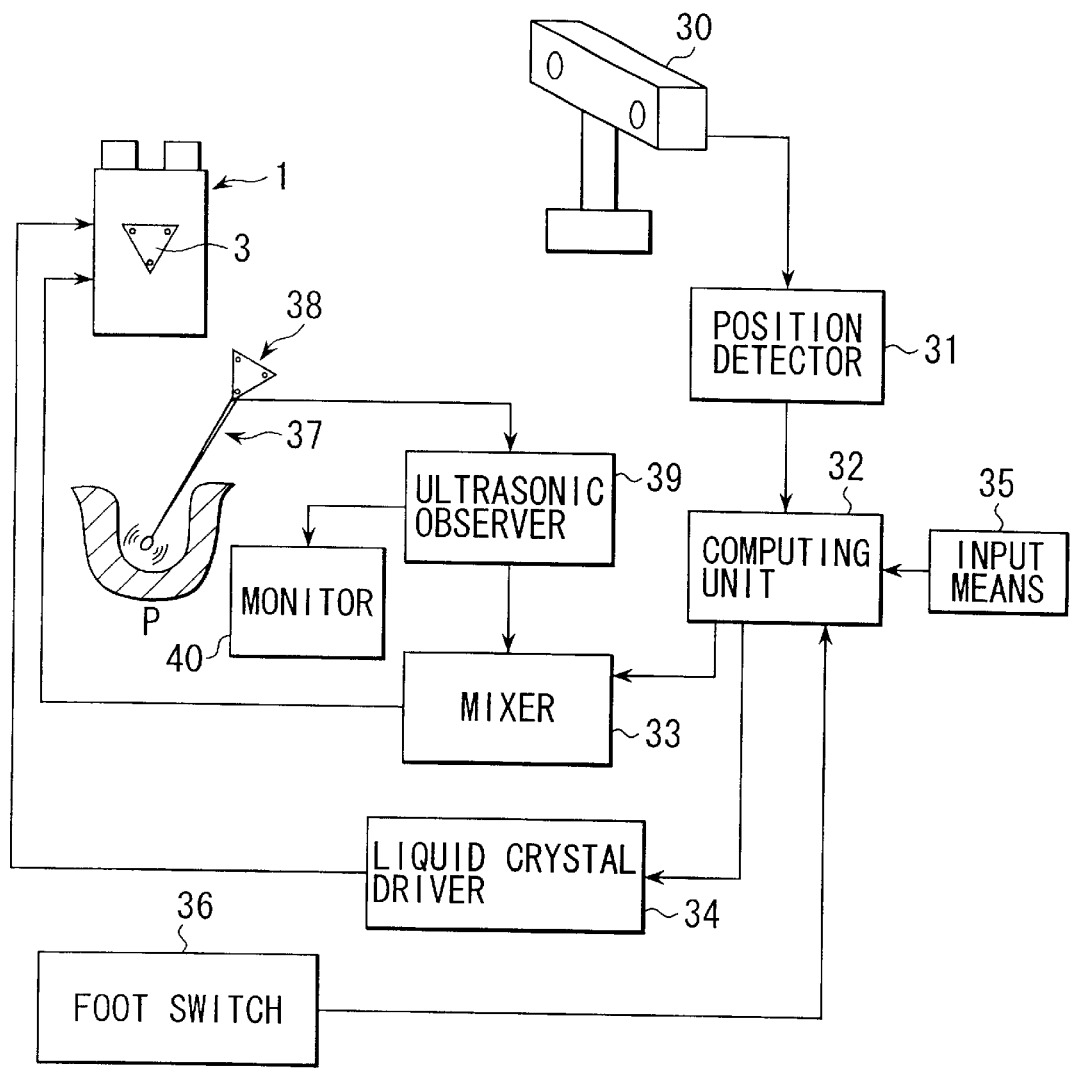
FIG. 2 is a block diagram of the surgical observational system according to the first embodiment.
Figure 3:
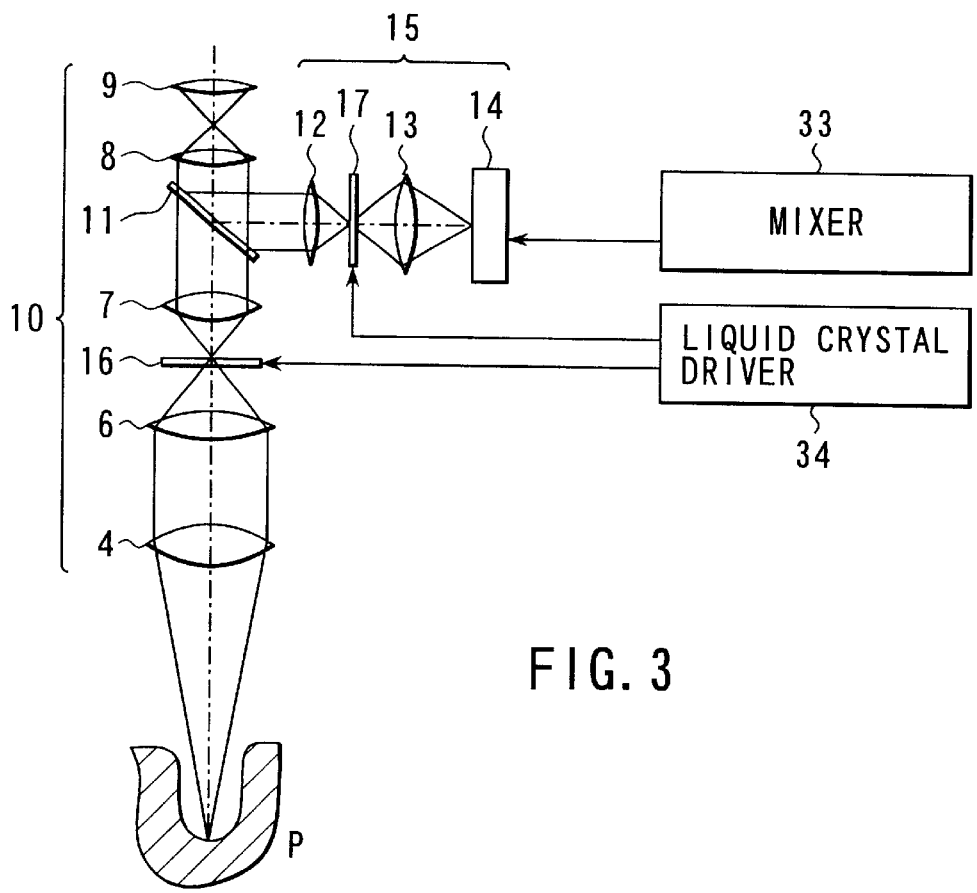
FIG. 3 is a detailed view for illustrating a microscope body portion of the operating microscope.

FIG. 1 shows an outline of an operating microscope for use as first observational means of a surgical observational system according to the present embodiment. FIG. 2 is a block diagram according to the present embodiment, and FIG. 3 shows a microscope body portion of the operating microscope in detail. Further, FIGS. 4A, 4B, 5A and 5B show the respective operations of first and second liquid crystal shutters, and FIGS. 6A and 6B individually show images observed by an operator. FIGS. 7A and 7B show an example of a display image on monitors 40 and 14.

The surgical observational system according to the first embodiment will be described first.

The operating microscope of the surgical observational system according to the present embodiment is provided with a stand 21, which includes a base 21a movable on a floor surface and a support post 21b set up on the base 21a. One end of a first arm 22, which has a light source for illumination (not shown) therein, is mounted on the upper end portion of the post 21b so as to be rotatable around an axis Oa.

One end of a second arm 23 is attached to the other end of the first arm 22, which is distant from the support post 21b, so as to be rotatable around an axis Ob. The second arm 23 is a pantograph arm that is formed of a link mechanism and a balancing gas spring. The other end of the arm 23 that is off the first arm 22 can be moved vertically. A third arm 24 is attached to the other end of the second arm 23 so as to be rotatable around an axis Oc. Further, the third arm 24 is provided with a swing arm 25 that enables a microscope body 1 to swing in the anteroposterior direction along the direction of the operator's observation around an axis Od and swing in the lateral direction of the operator's body around an axis Oe. The microscope body 1, an observational portion 2, and a handle 26 are mounted on the distal end portion of the arm 25.

In order to allow the microscope body 1 to be freely positioned in a three-dimensional space, moreover, each of the individual rocking portions that are rotatable around the axes Oa to Oe is provided with a electromagnetic brake. Each rocking portion can be locked and unlocked by means of a switch (not shown) that is provided on the handle 26. Preferably, a power source unit for the electromagnetic brakes should be incorporated in the support post 21b.

As shown in FIG. 2, the microscope body 1 is situated over an affected region P which is a portion or an area to be operated, and an index 3 for optical position detection is attached to a predetermined face of the microscope body 1. The index 3 is fitted with a plurality of infrared LED's of the time-sharing emission type, which will not be described in detail.

Although the microscope body 1 has therein two observational optical systems for supplying luminous fluxes individually to the two eyes of the operator, only one of them will be described for simplicity.

As shown in FIG. 3, an observational optical system 10 is composed of an objective lens 4, first imaging lens 6, lens 7, second imaging lens 8, and eyepiece 9, which are arranged successively from the side of the affected region P. A half-mirror 11 is interposed between the lenses 7 and 8 of the optical system 10. The half-mirror 11 is oriented so that it can reflect a luminous flux from a direction perpendicular to the optical axis of the observational optical system 10 toward the eyepiece 9. A projection optical system 15 is composed of a lens 12, third imaging lens 13, and monitor 14, which are arranged successively on an optical axis that extends at right angles to the optical axis of the optical system 10.

Further, a first liquid crystal shutter 16 is located on the imaging point of the first imaging lens 6 of the observational optical system 10, and a second liquid crystal shutter 17 on the imaging point of the third imaging lens 13 of the projection optical system 15.

As previously described with reference to FIG. 2, the microscope body 1 is fitted with the index 3 for optical position detection. An optical position detecting member 30 (hereinafter referred to as digitizer 30) is provided in a required position in an operating room where it can shoot the index 3.

The digitizer 30 includes a plurality of infrared cameras, which are mounted at given spaces. The digitizer 30 is connected to a position detector 31. The detector 31 is connected to a computing unit 32, which is connected with a mixer 33 and a liquid crystal driver 34. Further, the unit 32 is connected with input means 35 and a footswitch 36. The switch 36 is provided with an image on-off switch (not shown).

As shown in FIG. 3, the liquid crystal driver 34 is connected to the first and second liquid crystal shutters 16 and 17 in the microscope body 1. The mixer 33 is connected to the monitor 14 in the microscope body 1.

In FIG. 2, numeral 37 denotes an ultrasonic probe that is inserted in the affected region P. The probe 37 is fitted with an index 38 that resembles the one on the microscope body 1. The index 38 is also fitted with a plurality of infrared LED's of the time-sharing emission type, which will not be described in detail. However, the time-sharing emission patterns of the infrared LED's that are attached to the index 38 are different from those of the ones attached to the index 3. The position detector 31 can detect the respective positions of the patterns separately.

The ultrasonic probe 37 is connected to an ultrasonic observer 39. A video output (not shown) from the observer 39 is connected to the monitor 40 and the mixer 33.

Referring now to FIGS. 1 to 7B, there will be described the operation of the surgical observational system according to the first embodiment.

Figure 4A:
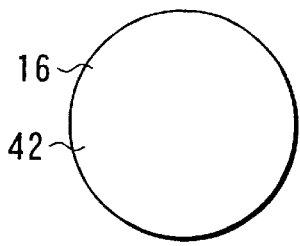
FIGS. 4A and 4B are views showing a state in which the whole surface of a first liquid crystal shutter is transmittable and a state in which a partial shading portion is provided in the shutter, respectively.

A luminous flux emitted from the light source (not shown) in the first arm 22 is applied to the affected region P of a patient's body through an optical fiber (not shown) and an illumination optical system (not shown). As shown in FIG. 3, the luminous flux reflected by the affected region P lands on the objective lens 4 of the microscope body 1, is focused through the first imaging lens 6, first liquid crystal shutter 16, lens 7, half-mirror 11, and second imaging lens 8, and is subjected to enlarged-scale observation through the eyepiece 9 by the operator. In this state, the whole surface of the first liquid crystal shutter 16 is transmittable, as shown in FIG. 4A. FIG. 6A shows the image that is observed by the operator in this state. This process will be mentioned later.

On the other hand, the ultrasonic probe 37 to be inserted into the affected region P may be formed of a conventional ultrasonic probe that emits an ultrasound from a rotating portion (not shown) on its distal end. The ultrasound reflected by the affected region P is received by a sensor (not shown), and a signal from the sensor is transmitted to the ultrasonic observer 39. The observer 39 analyzes the signal from the ultrasonic probe 37 and generates an image-processed video signal that is indicative of the internal structure of the tissue in accordance with the attenuation or phase of the ultrasound based on the rotational angle of the rotating portion (not shown). Then, the video signal is delivered to the monitor 40 to be displayed thereon. FIG. 7A shows the image then displayed on the monitor 40. The same video signal that is delivered to the monitor 40 is also delivered to the mixer 33.

Further, the index 3 that is attached to the microscope body 1 causes the infrared LED's (not shown) to glow in a given time-sharing pattern. Likewise, the index 38 that is attached to the ultrasonic probe 37 causes the infrared LED's (not shown) to glow in a time-sharing pattern different from the pattern for the index 3.

The respective states of light emission of the indexes 3 and 38 are shot by means of the infrared cameras (not shown) of the digitizer 30. The information obtained by means of the digitizer 30 is analyzed by means of the position detector 31, whereupon the respective positions and attitudes of the microscope body 1 and the ultrasonic probe 37 in the three-dimensional space are detected. A conventional suitable technique can be used for this optical position detection system.

Since the affected region P is also positioned in the three-dimensional space, moreover, the position detector 31 can detect the relative positions of the affected region P, microscope body 1 (observational position of the operating microscope), and ultrasonic probe 37 (plane for ultrasonic observation).

As shown in FIG. 2, the position information detected by means of the position detector 31 is delivered to the computing unit 32.

Figure 5A:
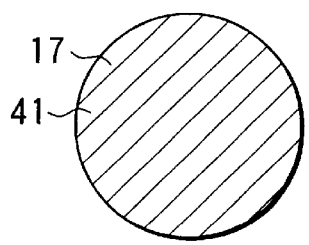
FIGS. 5A and 5B are views showing a state in which the whole surface of a second liquid crystal shutter is interceptive and a state in which a partial transparent portion is provided in the shutter, respectively.
Figure 5B:
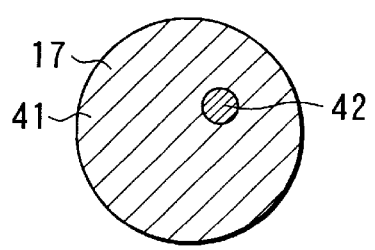

If the image on-off switch (not shown) of the footswitch 36 is then off, the computing unit 32 delivers an image-off signal to the mixer 33 and the liquid crystal driver 34. The mixer 33 outputs no image when it receives the image-off signal from the computing unit 32. Therefore, no image is displayed on the monitor 14 that is connected to the mixer 33. On receiving the image-off signal from the computing unit 32, moreover, the liquid crystal driver 34 delivers given outputs to the first and second liquid crystal shutters 16 and 17. Thereupon, the whole surface of the first liquid crystal shutter 16 becomes transmittable, as shown in FIG. 4A. Further, the second liquid crystal shutter 17 is rendered entirely interceptive, as shown in FIG. 5A. Thus, the operator can obtain no image from the monitor 1, only observing the optical image of the affected region P. FIG. 6A shows this state of observation.

If the operator then turns on the image on-off switch of the footswitch 36, an image-on signal is delivered to the computing unit 32. In this state, the computing unit 32 computes the position of the distal end of the ultrasonic probe 37 in the field of observation of the operating microscope on the basis of the detected information from the position detector 31. Further, the respective positions of the monitor 14 and the first and second liquid crystal shutters 16 and 17 corresponding to the distal end position are computed.

Then, the computing unit 32 calculates a signal from the input means 35 and settles the size of an image in the microscopic field. The operator can freely change the image size by operating the input means 35.

Based on the result of the aforesaid computation and the signal from the input means 35, the computing unit 32 delivers a control signal to the mixer 33. The mixer 33 converts the output image of the ultrasonic observer 39 into an image that has its center in a position corresponding to the distal end position of the ultrasonic probe 37 of the monitor 14, and further generates an image signal of a reduced size set by means of the input means 35. FIG. 7B shows this image signal.

Figure 4B:
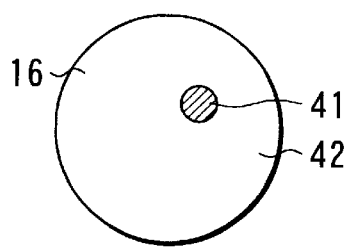

Then, the computing unit 32 delivers a control signal to the liquid crystal driver 34. The driver 34 generates, on the first and second liquid crystal shutters 16 and 17, a shielding portion 41 (first liquid crystal shutter 16) and a transparent portion 42 (second liquid crystal shutter 17) that have positions and sizes corresponding to the range of the reduced image that is generated by means of the mixer 33. This state is shown in FIG. 4B (for the first liquid crystal shutter 16) and FIG. 5B (for the second liquid crystal shutter 17).

In this arrangement, only that portion of the optical observational image from the objective lens 4 which corresponds to the shielding portion 41 is intercepted by means of the first liquid crystal shutter 16, and only the reduced image portion of the monitor 14 is transmitted to the side of the half-mirror 11 through the transparent portion 42 of the second liquid crystal shutter 17.

Thus, the operator can observe superposed ultrasonic images on the monitor 14 in a predetermined range centering around the distal end of the ultrasonic probe 37, among other microscopic images. If the operator moves the probe 37 within the microscopic field, the ultrasonic images also move correspondingly in the field. FIG. 6B shows this state of observation.

If the operator operates again the image on-off switch (not shown) of the footswitch 36, the ultrasonic images disappear in a moment, and the state of observation shown in FIG. 6A is restored.

Thus, the surgical observational system according to the first embodiment can produce the following effects.

According to the first embodiment, the operator can observe the optical observational image and ultrasonic diagnostic images in a superposed manner, and the optical observational image is superposed only partially. Therefore, the diagnostic images and the affected region can be easily correlated, and transfer to each treatment can be effected smoothly. Since the images follow the ultrasonic probe, moreover, the operator can observe a desired region without delay. In consequence, the operation time can be shortened, and the operator's fatigue can be eased.

Second Embodiment

A second embodiment of the present invention will now be described with reference to FIGS. 8 to 10C.

In these drawings, like reference numerals refer to the same portions of the first embodiment, and a description of those portions is omitted.

Figure 8:
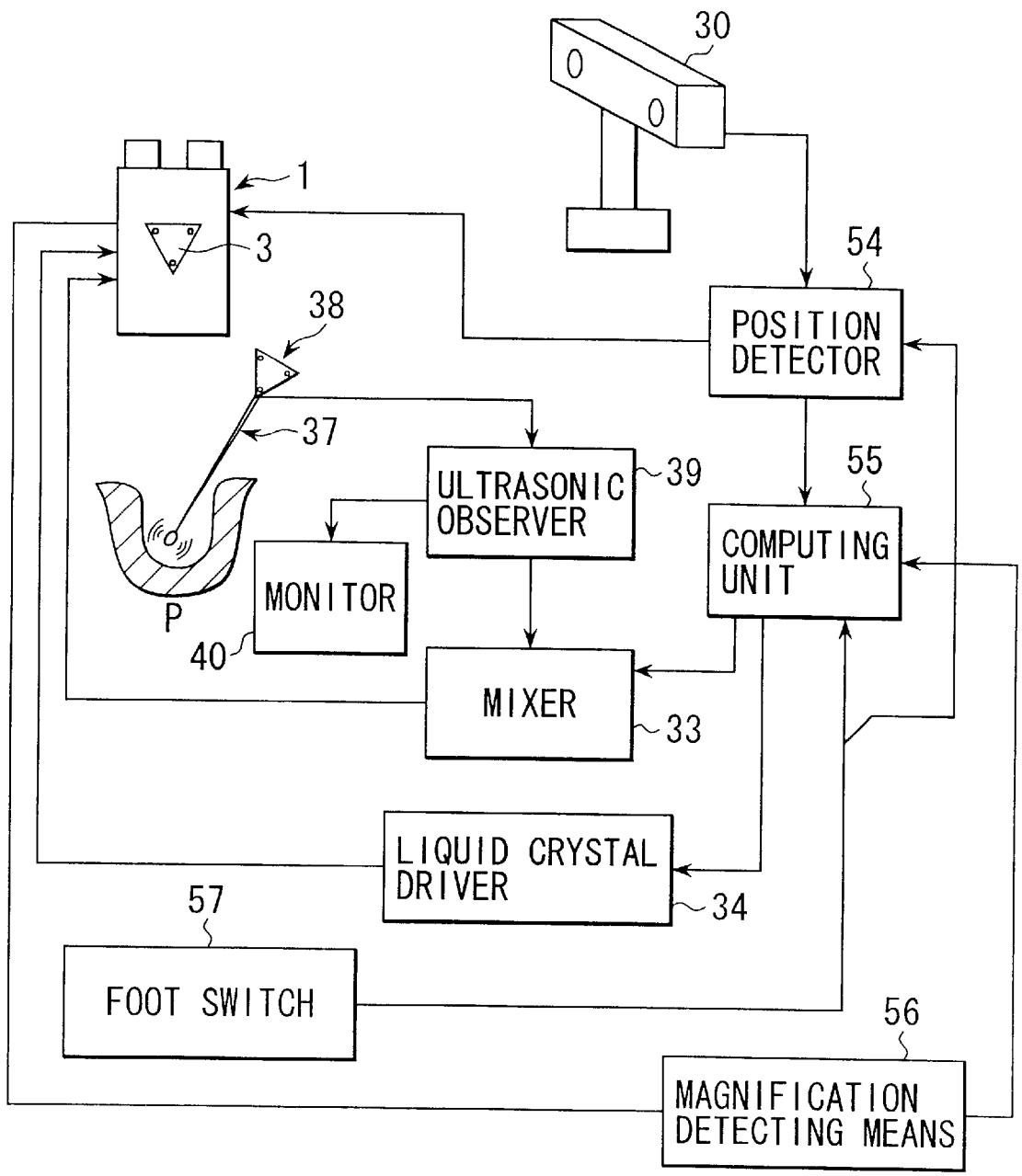
FIG. 8 is a block diagram of a surgical observational system according to a second embodiment.
Figure 9:
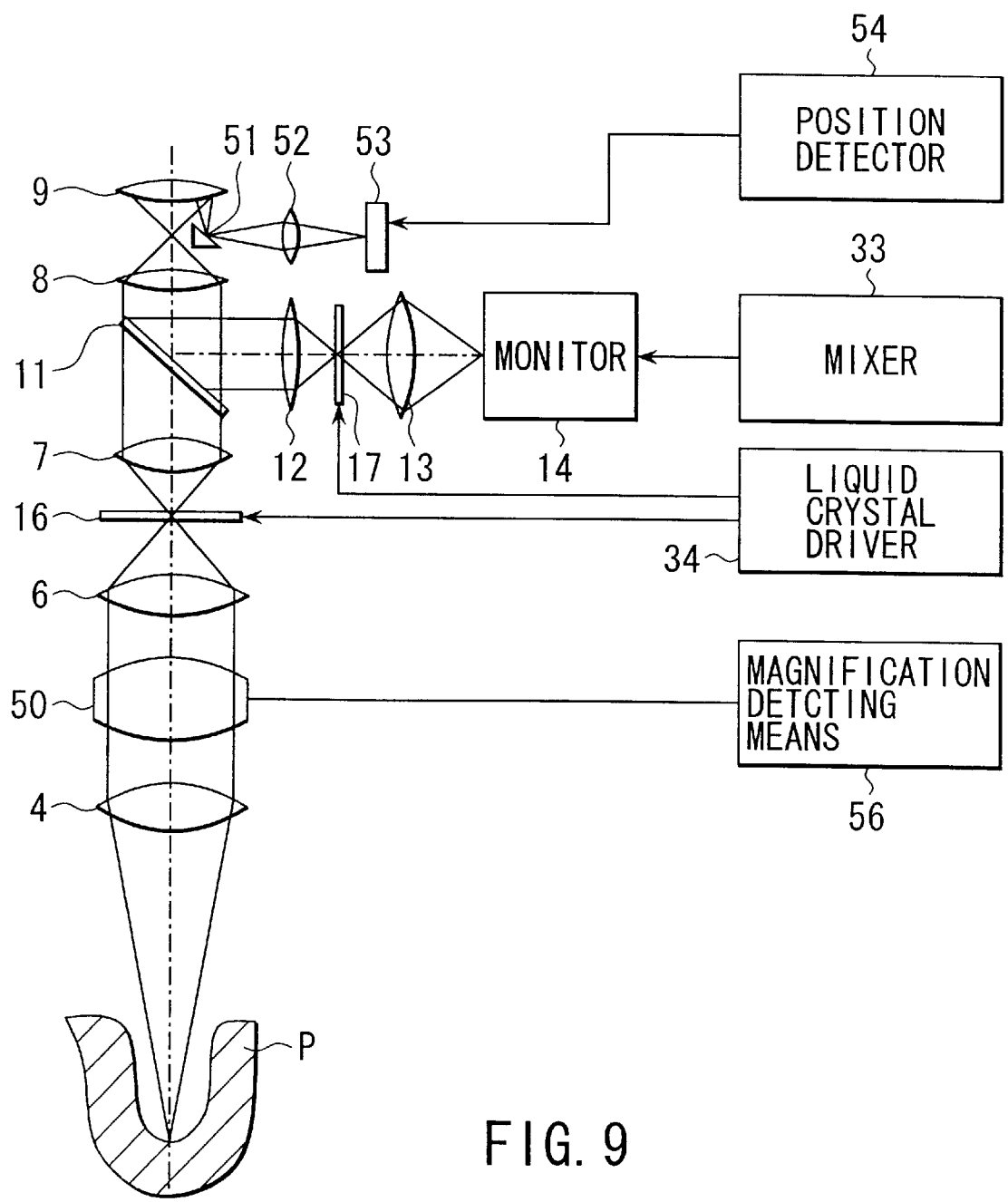
FIG. 9 is a detailed view for illustrating a microscope body portion of an operating microscope.
Figure 10A:
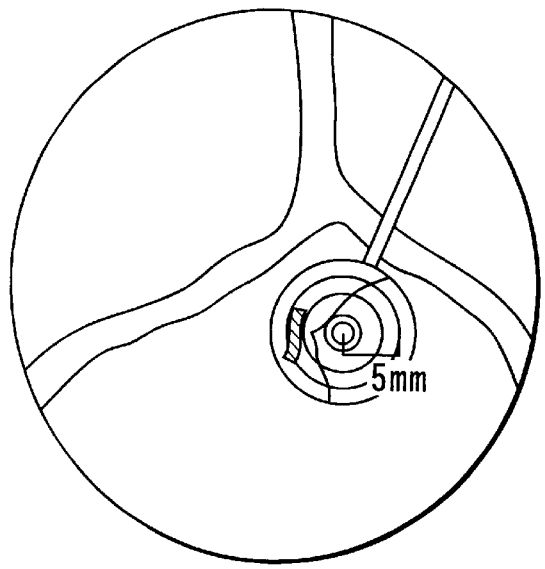
Figure 10B:
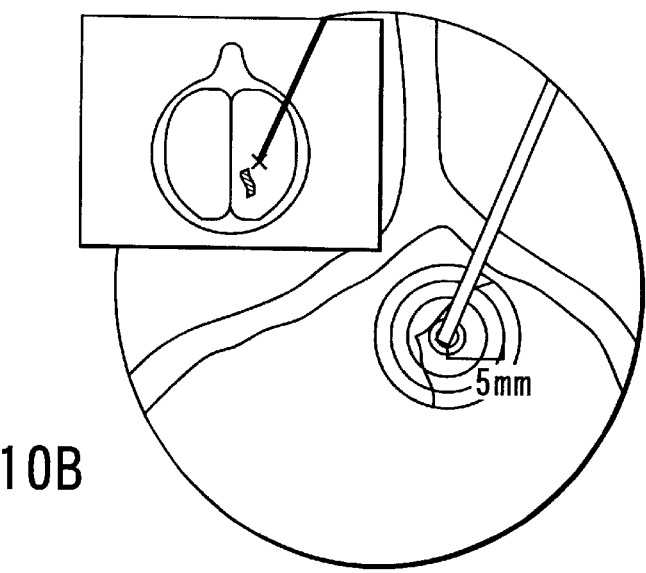
Figure 10C:
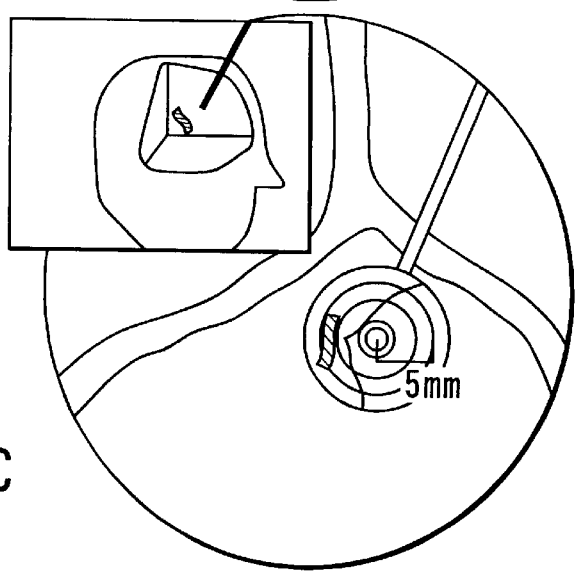

FIG. 8 is a block diagram according to the present embodiment, FIG. 9 shows the body of the operating microscope in detail, and FIGS. 10A to 10C individually show varied states of images the operator observes.

A surgical observational system according to the second embodiment will be described first.

In the second embodiment, as shown in FIG. 9, a variable-scale optical system 50 is interposed between an objective lens 4 and a first imaging lens 6 of a microscope body 1. A lens drive section (not shown) of the optical system 50 is provided with a sensor (not shown), which is connected to magnification detecting means 56. As shown in FIG. 8, the detecting means 56 is connected to a computing unit 55.

A changeover switch (not shown) of a footswitch 57, which is connected to the computing unit 55, is connected to a position detector 54. As in the case of the first embodiment, the output of a digitizer 30 is connected to the position detector 54. The position detector 54 includes an image forming section (not shown), the image output of which is connected to a monitor 53 in the microscope body 1. A fourth imaging lens 52 and a mirror 51 are arranged successively on the emission side of the monitor 53. The imaging position of the fourth imaging lens 52 is substantially aligned with the reflective surface of the mirror 51 and the imaging plane of a second imaging lens 8. Accordingly, the operator can simultaneously observe, through an eyepiece 9, a microscopic optical image formed by means of the first imaging lens 6 and an image on the monitor 53 formed by means of the fourth imaging lens 52.

The following is a description of the operation of the surgical observational system according to the second embodiment.

As in the case of the first embodiment, the position detector 54 can detect the respective positions of the point of microscope observation and the distal end of an ultrasonic probe 37 relative to the affected region P. Further, the detector 54 stores preoperative diagnostic images (e.g., slice images of an X-ray CT apparatus; normally, slice images in a given direction and a three-dimensional CG image constructed by joining the slice images) in its storage section (not shown). In starting observation of the ultrasonic images in the microscopic field, the operator turns on an image on-off switch (not shown) of the footswitch 57. As this is done, a signal from the sensor (not shown) of the variable-scale optical system 50 is transmitted to the magnification detecting means 56. The detecting means 56 calculates the observation magnification of the microscope and delivers it to the computing unit 55.

Based on data from the magnification detecting means 56, the computing unit 55 sets the display size of an ultrasonic image to be projected in the microscopic field. FIG. 10A shows the state of the image the operator then observes.

If the operator operates the changeover switch (not shown) of the footswitch 57 in this state, moreover, the position detector 54 reads a preoperative diagnostic slice image corresponding to the position of the distal end portion of the ultrasonic probe 37 from the storage section (not shown). Then, the detector 54 superposes a marker on a region where the ultrasonic probe 37 is situated, and delivers the resulting image to the monitor 53. AS this is done, the mirror 51 moves from an evacuation position (not shown) to an observational position shown in FIG. 9, whereupon the operator can observe the image on the monitor 53 along with a microscopic image through the mirror 51.

When the operator depresses the changeover switch (not shown) once, a preoperative diagnostic slice image, such as the one shown in FIG. 10B, is displayed. In this state, the operator can observe the actual affected region and the ultrasonic diagnostic image in association with the preoperative diagnostic slice image (with the display of the ultrasonic probe position).

If the operator depresses the changeover switch once again, the position detector 54 reads the three-dimensional image of the affected region P from the storage section (not shown), and carries out rotation processing (image processing) of the three-dimensional image so that the image is aligned with the direction of actual insertion of the ultrasonic probe 37 into the affected region. Then, the detector 54 superposes the marker on the region and along the direction in which the probe 37 is situated, and delivers the resulting image to the monitor 53. FIG. 10C shows the image the operator then observes. In this state, the operator can observe the actual affected region and the ultrasonic diagnostic image in association with the three-dimensional preoperative diagnostic image (with the display of the ultrasonic probe position and direction).

If the operator depresses the changeover switch once again, the mirror 51 moves to the aforesaid evacuation position (not shown), whereupon the operator can observes the image shown in FIG. 10A.

The surgical observational system according to the second embodiment can produce the following effects.

According to the second embodiment, which enjoys the same effects of the first embodiment, the display size of the ultrasonic image can be set automatically according to the observation magnification of the operating microscope. Therefore, the operator can be saved the trouble of setting the image size, so that the efficiency of surgical operations can be improved. Further, the operator can observe the preoperative diagnostic image simultaneously with the optical observational image and ultrasonic diagnostic image. Accordingly, the approximate position of the whole patient's body in the position for ultrasonic observation can be recognized with ease. Besides, the deviation between the actual affected region and the preoperative diagnostic image, which is attributable to change of the intracranial pressure after craniotomy or exclusion of tissue, can be recognized easily. Thus, accurate surgical operations can be carried out, and the results of operations can be improved.

Although the ultrasonic diagnostic image is displayed substantially in a circular form on the monitor 14 according to the second embodiment, its shape may be changed in the following manner.

Figure 11A:
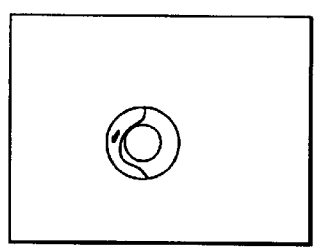
Figure 11B:
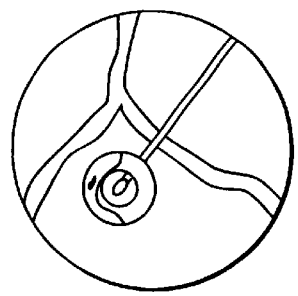

In the case of an ultrasonic probe of the same radial-scan type (in which the periphery of the probe is scanned in a circle) as in the foregoing embodiment, as shown in FIG. 11A, the central portion of the ultrasonic probe 37 may be extracted by means of the mixer 33 as it is displayed. The range of extraction is restricted to a radius that ranges from the distal end of the ultrasonic probe to the inner wall of the tissue of the affected region that is located closest to the probe. This range can be settled by analyzing the ultrasonic image or by means of an optical position detector. FIG. 11B shows an actual image then observed by the operator.

According to this arrangement, a microscopic optical image is displayed in a range without any object of diagnosis, extending from the ultrasonic probe to the inner wall of the tissue of the affected region, and the region to be diagnosed can be displayed securely. Accordingly, the diagnosis can be carried out in the same manner as in the second embodiment, and the distal end of the ultrasonic probe never fails to be recognized on the optical observational image. Thus, the operator can move the ultrasonic probe without switching off the display of the ultrasonic image, so that the efficiency of surgical operations can be improved.

Third Embodiment

A third embodiment of the present invention will now be described with reference to FIGS. 12 to 15D. In these drawings, like reference numerals refer to the same portions of the first and second embodiments, and a description of those portions is omitted.

Figure 12:
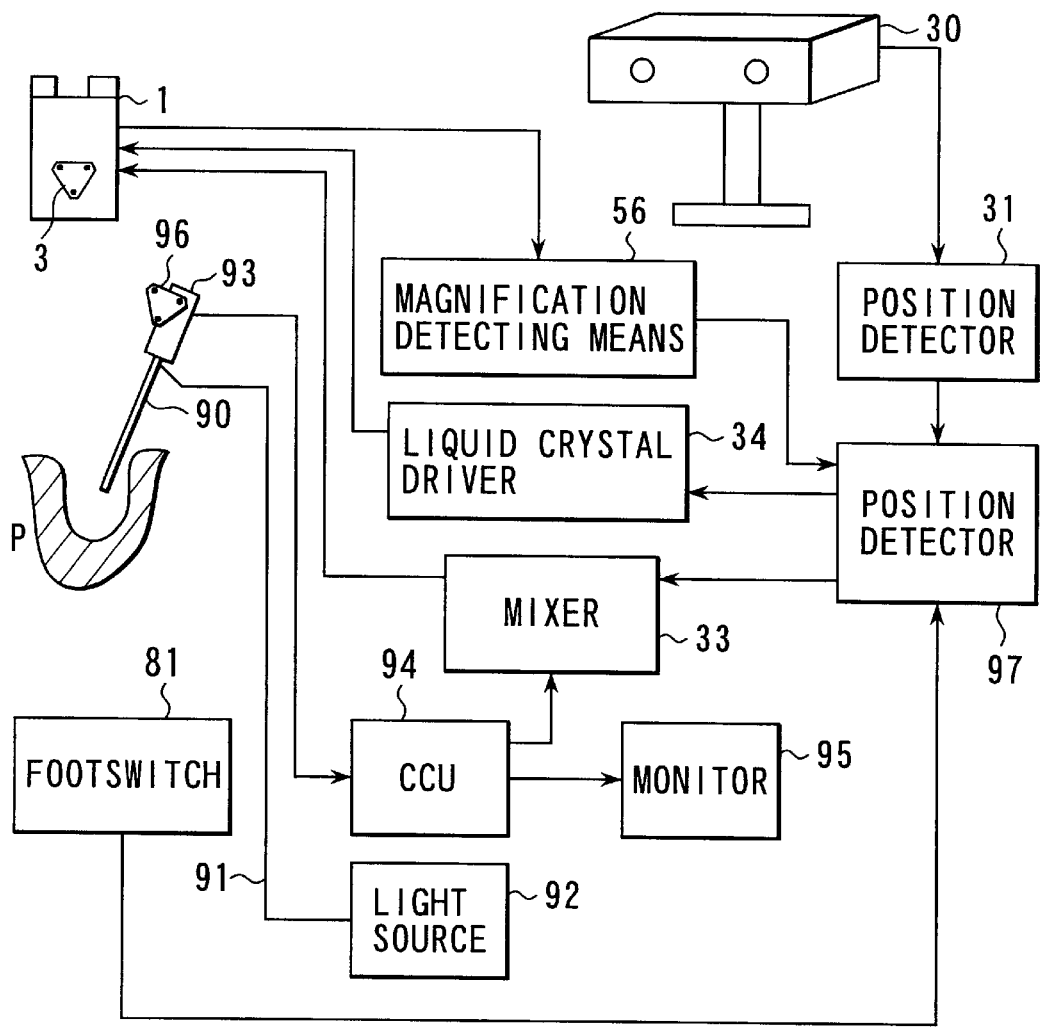
FIG. 12 is a general block diagram of a surgical observational system according to a third embodiment.
Figure 13:
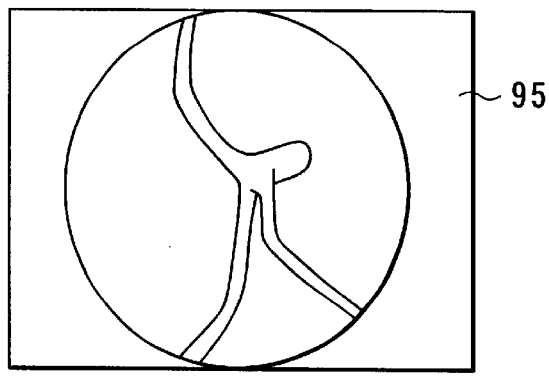
FIG. 13 is a view showing the way an observational image of a rigid scope for use as second observational means according to the third embodiment is displayed on a monitor.

FIG. 12 is a general block diagram illustrating the present embodiment, and FIG. 13 shows an observational image of a rigid scope for use as second observational means according to the present embodiment. FIGS. 14A to 14F illustrate the respective operations of first and second liquid crystal shutters according to the present embodiment, and FIGS. 15A to 15D show images observed by the operator according to the present embodiment.

A surgical observational system according to the third embodiment will be described first.

Numeral 1 denotes a body of an operating microscope that resembles the one according to the first embodiment. The microscope body 1, like the one according to the first embodiment, is fitted with an index 3. AS in the case of the second embodiment, a variable-scale optical system (not shown) of the microscope body 1 is provided with a sensor (not shown), which is connected to magnification detecting means 56. As in the cases of the first and second embodiments, moreover, the microscope body 1 is provided with first and second liquid crystal shutters (not shown), which are connected to a liquid crystal driver 34. The microscope body 1 is provided with a monitor (not shown) that resembles the one according to the first embodiment. The monitor is connected to a mixer 33. Thus, the optical system in the microscope body 1 of the present embodiment is constructed substantially in the same manner as the one according to the first embodiment.

Numeral 90 denotes a 90°-squint rigid scope for use as second observational means according to the present embodiment. The rigid scope 90 is connected with one end of a light guide 91, the other end of which is connected to a light source 92. The rigid scope 90 is fitted with a camera head 93 for picking up its observational image. The camera head 93 is connected to a camera control unit 94 (hereinafter referred to simply as CCU 94). A first video output section (not shown) of the CCU 94 is connected to a monitor 95. A second video output section (not shown) of the CCU 94 is connected to the mixer 33. Further, an index 96 for position detection is attached to given position on the camera head 93.

A digitizer 30 is located in a position such that it can shoot both the indexes 3 and 96 that are attached to the microscope body 1 and the camera head 93, respectively. The digitizer 30 is connected to a position detector 31. The detector 31 is connected to a computing unit 97. Further, the magnification detecting means 56 and a footswitch 81 are connected to the computing unit 97.

Furthermore, the computing unit 97 is connected to the mixer 33 and the liquid crystal driver 34.

The following is a description of the operation of the third embodiment.

As in the case of the first embodiment, the operator subjects the affected region P to enlarged-scale stereoscopic optical observation by using the microscope body 1. Further, the operator uses the rigid scope 90 to observe outside portions as viewed through the microscope body 1 for the optical observation. More specifically, a luminous flux for observation emitted from the light source 92 is landed on the light guide 91. The light guide 91 transmits the incident luminous flux to the rigid scope 90 that is connected to the other end thereof. This luminous flux is applied to the affected region P through an illumination optical system (not shown) in the rigid scope 90. The luminous flux reflected by the affected region P is landed on an objective lens (not shown) of the rigid scope 90 and focused on an image-pickup device (not shown) of the camera head 93 that is connected to the rear end of the scope 90. The camera head 93 converts the luminous flux, focused on the image-pickup device, into an electrical signal, and delivers it to the CCU 94. The CCU 94 converts the electrical signal into a standardized video signal, and delivers it through its first and second video output sections (not shown).

Thus, the image shot by means of the rigid scope 90 is displayed on the monitor 95 that is connected to the first video output section of the CCU 94, as shown in FIG. 13. The same video signal is delivered from the second video output section of the CCU 94 to the mixer 33 in like manner.

Infrared cameras (not shown) of the digitizer 30 are used to shoot infrared LED's (not shown) of the indexes 3 and 96 that are attached to the microscope body 1 and the camera head 93 of the rigid scope 90, respectively. As in the case of the first embodiment, the information obtained by means of the digitizer 30 is analyzed by means of the position detector 31, whereupon the respective positions and attitudes of the microscope body 1 and the rigid scope 90 in the three-dimensional space are detected. Since the affected region P is also positioned in the three-dimensional space, moreover, the position detector 31 can detect the position of the affected region P relatively to the respective observational positions and directions of the microscope body 1 and the rigid scope 90.

The position information detected by means of the position detector 31 is delivered to the computing unit 97.

Figure 15A:
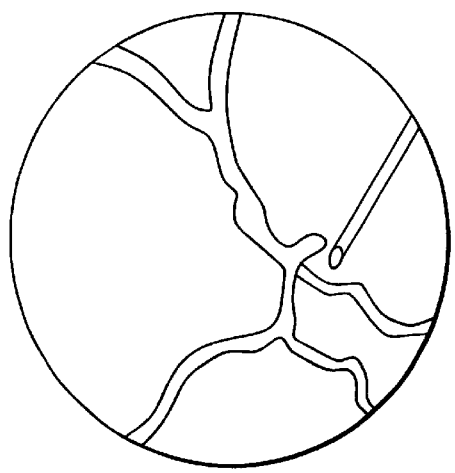
FIGS. 15A to 15D show images observed by the operator according to the third embodiment and illustrate various positional relations between the image obtained by means of the rigid scope and an optical image obtained by means of the microscope.

FIG. 15A shows an image then observed by the operator. The operator observes only an optical image that is obtained by means of the body 1 of the operating microscope. In this state, the first liquid crystal shutter (not shown) in the microscope body 1 is fully transmittable, while the second liquid crystal shutter (not shown) is entirely interceptive. An image then obtained by means of the rigid scope 90 is displayed on the monitor 95.

Figure 15B:
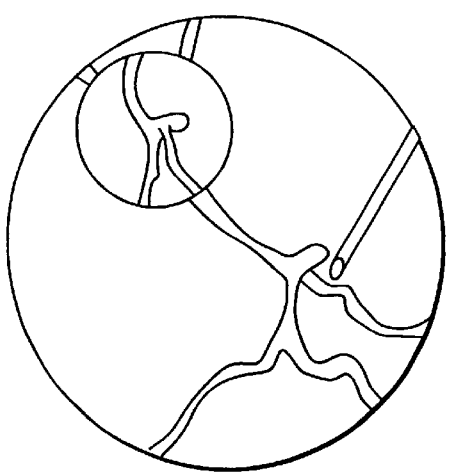
Figure 15C:
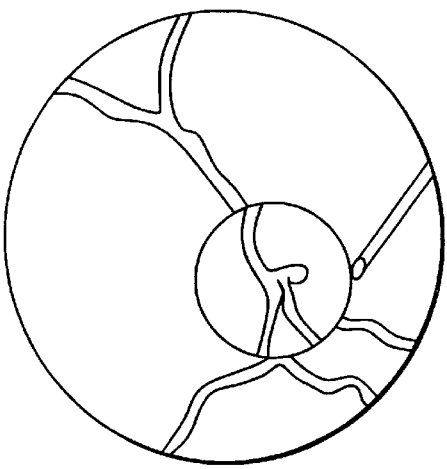
Figure 15D:
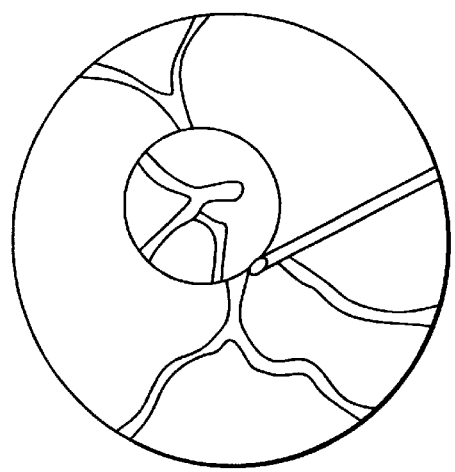

In starting observation of the image obtained by means of the rigid scope 90 in the microscopic field, the operator turns on an image on-off switch (not shown) of the footswitch 81. The resulting signal is transmitted to the computing unit 97. On receiving an image-on signal from the footswitch 81, the computing unit 97 first carries out computation to display the image in a given position in the microscopic field (upper left portion of the microscopic field according to the present embodiment) and delivers command signals to the liquid crystal driver 34 and the mixer 33. More specifically, a signal is delivered to the liquid crystal driver 34 such that it controls the first and second liquid crystal shutters for the states shown in FIG. 14A and 14B, respectively. Further, a signal is delivered to the mixer 33 such that the video signal from the CCU 94 is reduced at a suitable scale factor computed on the basis of a signal from the magnification detecting means 56 and that the image is moved to a region corresponding to a shielding portion of the second liquid crystal shutter and displayed on the monitor (not shown) in the microscope body 1 in the manner shown in FIG. 14C. FIG. 15B shows the state of the image then observed by the operator. In this state, the operator roughly positions the rigid scope 90 while comparing the distal end of the rigid scope 90 and the affected region.

Then, in displaying the microscopic field and the field of the rigid scope 90 in association with each other, the operator turns on an image shift switch (not shown) of the footswitch 81. The resulting signal is applied to the computing unit 97. On receiving this signal, the computing unit 97 computes the position of display of the image of the rigid scope 90 in the microscopic field in accordance with position information from the position detector 31 and magnification information on the microscope body 1 from the magnification detecting means 56. Thus, the range of the microscopic field is calculated from the position and magnification of the body 1 of the microscope, while the distal end position and observational direction of the rigid scope 90 in the microscopic field is calculated from the position information of the scope 90. Based on the results of these calculations, the computing unit 97 delivers a command signal to display the image of the rigid scope 90 in a circular range that has its center on the observational-direction side of the rigid scope 90 with its distal end on a point on the diameter of the circle. More specifically, the first and second liquid crystal shutters are set for the states shown in FIGS. 14D and 14E, respectively, and the monitor (not shown) in the microscope body 1 displays the image shown in FIG. 14F. Thus, the operator can obtain the field shown in FIG. 15B in the microscopic field. Since the rigid scope 90 is 90°-squint, moreover, the observational direction changes if it is rotated for 90° in its axial direction, for example. In this state also, the image of the rigid scope 90 is displayed in a circular range that has its center on the observational-direction side of the rigid scope 90 with its distal end on a point on the diameter of the circle, so that the field shown in FIG. 15D can be obtained.

According to this third embodiment, the second observational means, e.g., the rigid scope or an ultrasonic observation apparatus of the front-scan type, can be effectively used in particular when an object is observed in a given direction from the distal end of the probe, and the observational image is displayed in the observational direction of the probe. Accordingly, the observational direction and position of the second observational means can be grasped with ease, and besides, the optical image of the actual affected region and the image obtained by means of the second observational means are positioned in association with each other as they are displayed. Thus, the state of the affected region can be grasped quickly and accurately.

Although the second observational means has been described as means for observing a narrower range than the operating microscope or first observational means does, in connection with the second and third embodiments, the present invention is not limited to this arrangement. If an image of a wide range that includes the affected region is obtained by means of an X-ray CT apparatus or the like, for example, a part of the image may be cut out and projected in the microscopic field in like manner provided that the positional relations between the image, the actual affected region, and the position of the body of the microscope can be grasped. According to each of the foregoing embodiments, the image is displayed following the distal end of each probe. In the case of a wide-range image such as the aforesaid X-ray CT image, however, a cursor may be displayed in the microscopic field so that the operator can move it by means of the footswitch or the like, thereby causing the cut image to follow the cursor. Thus, the operator can observe only a desired portion of the X-ray CT image to be referred to, in association with the affected region, so that the effects of the present invention can be accomplished.

Although the operating microscope is used as the first observational means and the image of the second observational means is superposed on the microscopic optical image according to the first to third embodiments, the present invention is not limited to this arrangement. It is to be understood that quite the same effects can be produced if the display image of the first observational means is a TV monitor.

Fourth Embodiment

A fourth embodiment of the present invention will now be described. The following is a description of a configuration of a fluorescent image observation apparatus of an operating microscope with position detecting means that can detect the position of an affected region.

Figure 16:
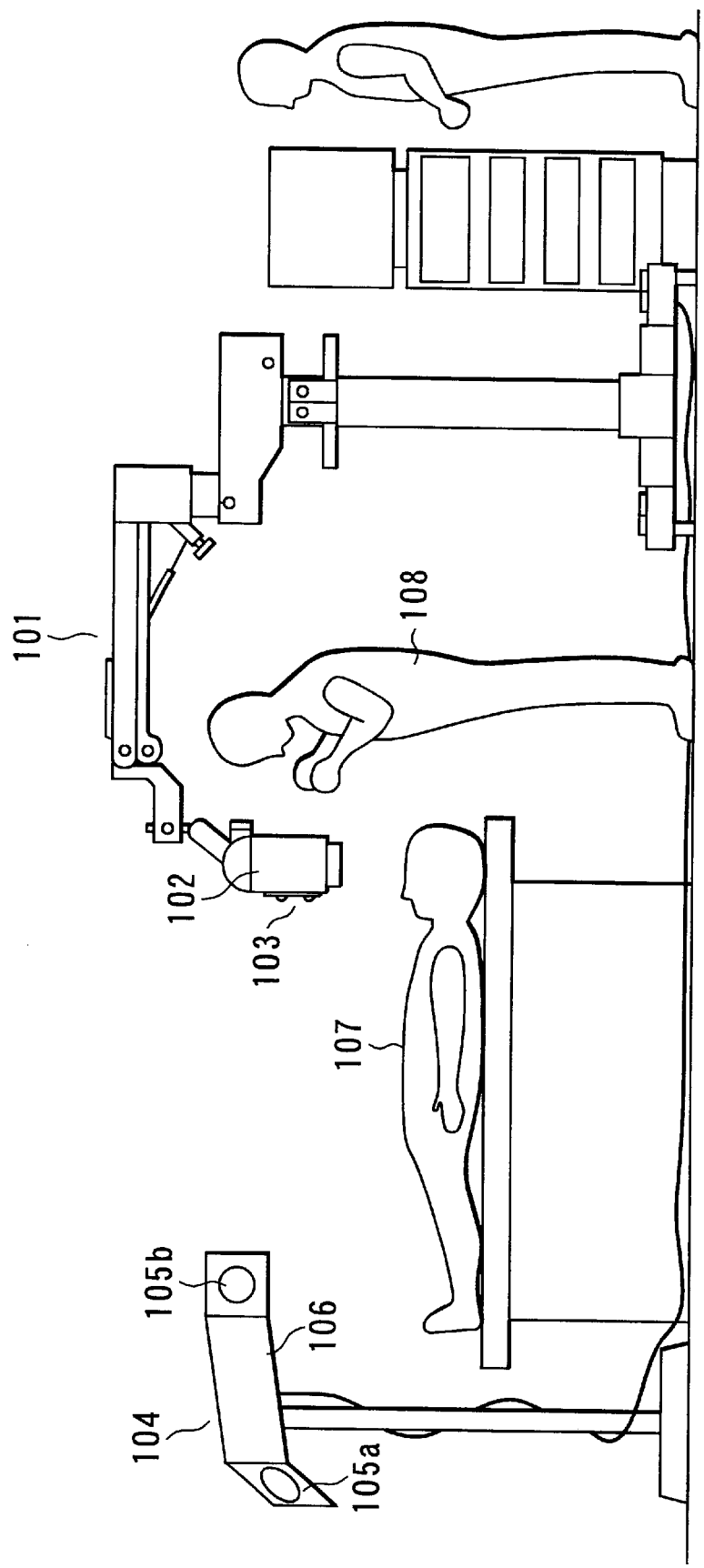
FIG. 16 is a view showing a configuration of an operating microscope according to a fourth embodiment of the invention.

FIG. 16 shows a configuration of the operating microscope with the position detecting means that can detect the affected region position. This configuration will be briefly described herein, since it is described in Jpn. Pat. Appln. No. 10-319190 filed by the assignee of the present invention. Numeral 101 denotes the operating microscope, which comprises a microscope body 102 that constitutes an observational optical system through which an operator 108 can observe an affected region of a patient 107. The microscope body 102 is provided with an emissive index 103.

Numeral 104 denotes a digitizer 104, which includes two CCD cameras 105a and 105b for use as receivers and a camera support member 106 for supporting these cameras. The digitizer 104 serves as optical position detecting means that uses the CCD cameras 105a and 105b to detect the emissive index 103 of the microscope body 102, thereby detecting the observational position of the microscope.

Figure 17:
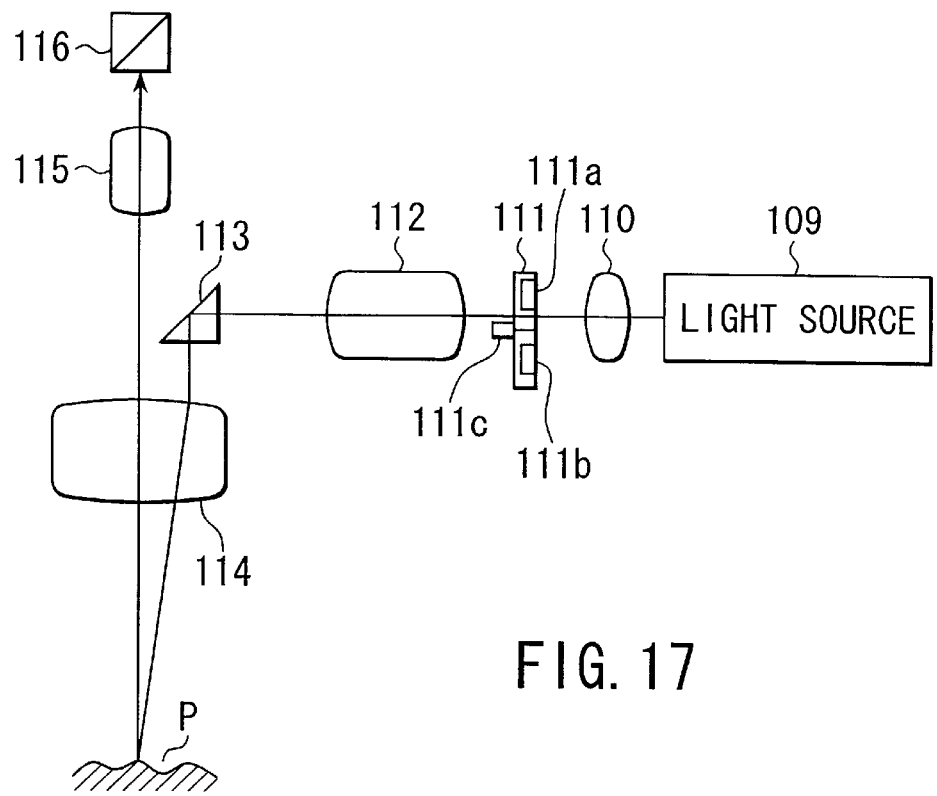
FIG. 17 is a view showing a configuration of an illumination system of the operating microscope.
Figure 18:
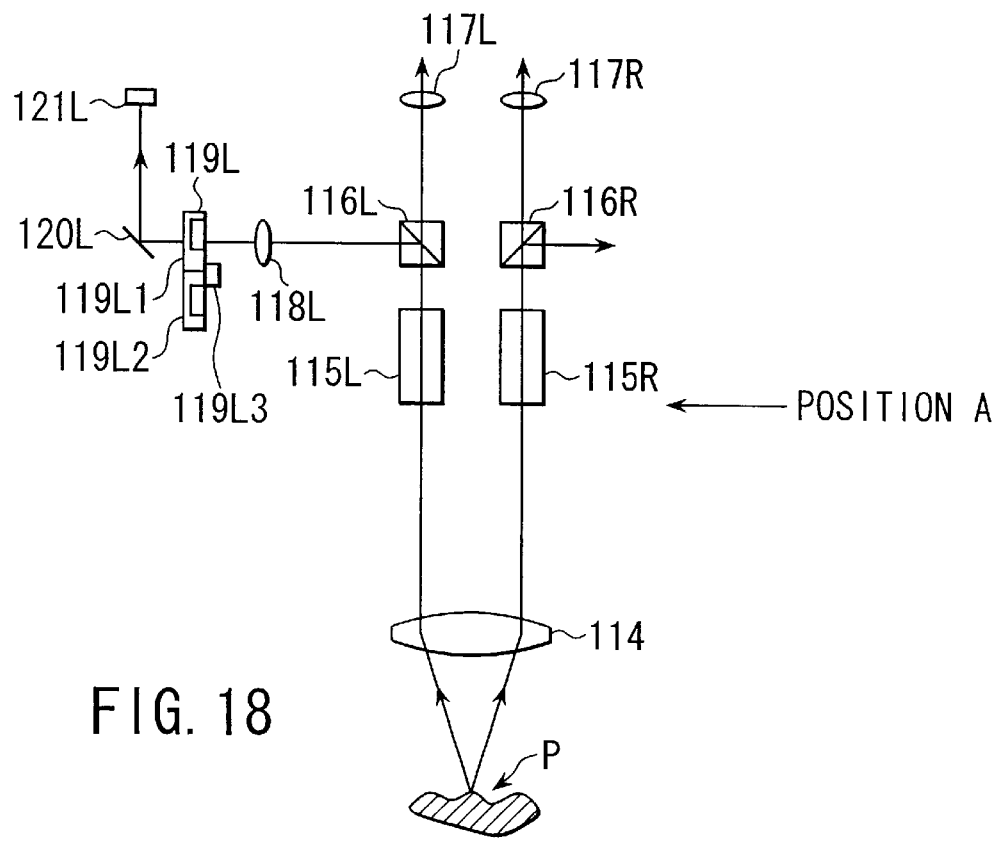
FIG. 18 is a view showing a configuration of an observational optical system of the operating microscope.

FIG. 17 shows a configuration of an illumination system of the operating microscope 101, and FIG. 18 shows a configuration of the observational optical system of the microscope 101. FIG. 17 is a diagram as viewed from a position A of FIG. 18.

The illumination system shown in FIG. 17 comprises a light source 109, condensing lens 110, illumination lens 112, and beam splitter 113. The members 110, 112 and 113 serve to guide illumination light emitted from the light source 109 to the affected region P of the patient 107.

An illumination light switching filter 111 includes an illumination light transmitting filter 111a for transmitting illumination light for the affected region P, an excitation light transmitting filter 111b for transmitting only excitation light that is inductive to fluorescence, and a drive motor 111c for use as a switching mechanism for changing these two filters. Thus, the filter 111 serves as illumination light switching means for the affected region P. Further, an objective lens 114, zoom optical systems 115L and 115R, and beam splitters 116L and 116R are provided for the observation of light reflected by the affected region P.

The observational optical system shown in FIG. 18 comprises the beam splitters 116L and 116R and eyepieces 117L and 117R, as well as the zoom optical systems 115L and 115R. An image from the affected region P is transmitted through the beam splitter 116L to a lens 118L, a mirror 120L, and an image-pickup device 121L, which constitute a shooting system.

An observational light switching filter 119L includes an illumination light transmitting filter 119L1 for transmitting the illumination light for the affected region P, a cutoff filter 119L2 for cutting off the excitation light and illumination light, and a drive motor 119L3 for use as a switching mechanism for changing these two filters. Thus, the filter 119L serves as observational light switching means for the affected region P.

Figure 19:
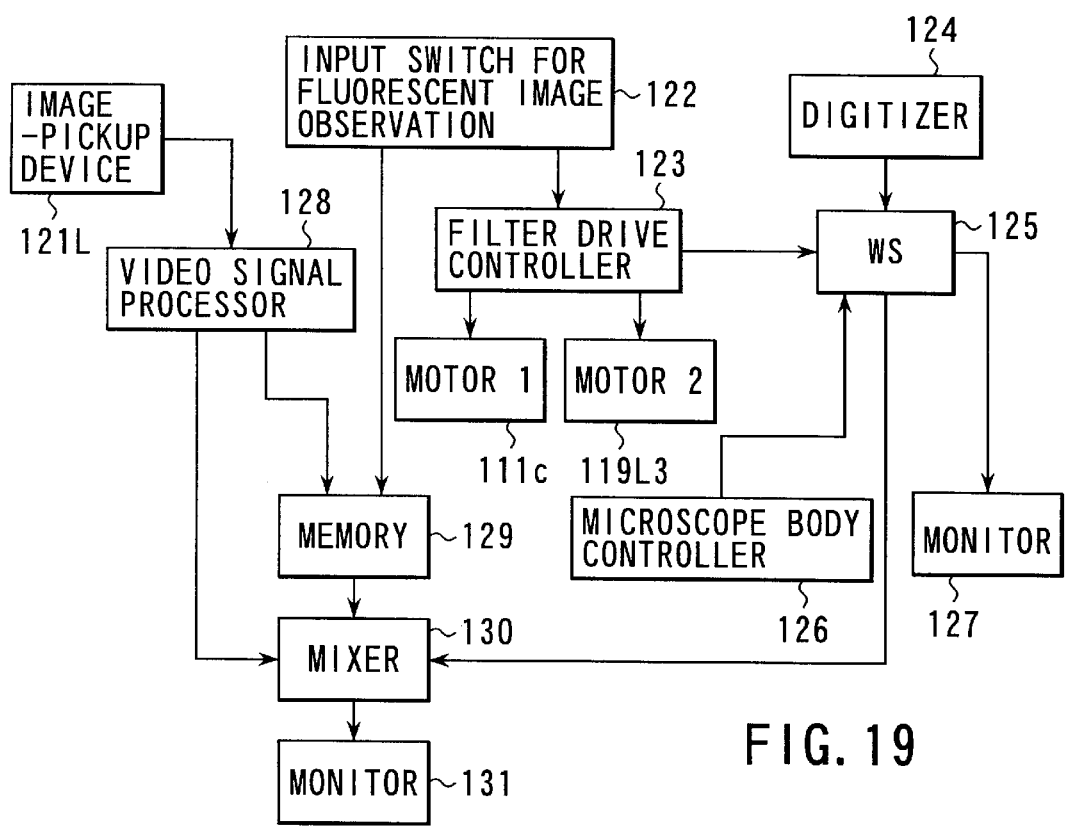
FIG. 19 is a general functional block diagram of the operating microscope.

FIG. 19 is a general functional block diagram of the operating microscope 101. In FIG. 19, the motors 111c and 119L3 are connected to a filter drive controller 123, which can control these motors simultaneously, in response to a signal from an input switch (display mode setting means) 122 for fluorescent image observation. The filter drive controller 123 serves to control the motors 111c and 119L3 so that the illumination light transmitting filter 111a of the illumination light switching filter 111 and the illumination light transmitting filter 119L1 of the observational light switching filter 119L are simultaneously situated on the optical axis. The controller 123 also serves to control the motors 111c and 119L3 so that the excitation light transmitting filter 111b of the illumination light switching filter 111 and the cutoff filter 119L2 of the observational light switching filter 119L are simultaneously situated on the optical axis. Under this control, the operation mode can be changed from a fixed-time fluorescent observation mode to a normal (visible zone) observation mode by means of a timer circuit (not shown).

Further, the image-pickup device 121L is connected to a video signal processor 128. The device 121L is composed of a drive processor circuit (not shown) and a video signal generator circuit (not shown). A memory (storage means) 129, which can operate in response to a signal from the input switch 122, is composed of an image memory and a binary coder circuit (not shown) for binary-coding a video signal delivered from the video signal processor 128.

Furthermore, a workstation (hereinafter referred to as WS) 125 is connected with a microscope body controller 126, digitizer 124, monitor 127, and mixer 130. The controller 126 can detect and transmit information data such as the magnification, focal length, etc. of the operating microscope 101 that is provided with the emissive index 103. The digitizer 124 can detect the position of the affected region P by detecting the index 103. If the magnification and focus information data are changed, they are transmitted from the controller 126 to the WS 125. Thereupon, the WS 125 selects a preoperative image corresponding to the operating position in consideration of the transmitted data and position information from the digitizer 124. The digitizer 124 and the WS 125 constitute position computing means.

The mixer 130, which is connected to the WS 125, video signal processor 128, and memory 129, serves to superpose video signals that are transmitted individually from the WS 125, processor 128, and memory 129, and can display the superposed video signals on a monitor 131 outside the microscope body. The mixer 130 and the monitor 131 constitute display means.

In the arrangement described above, the observational position of the operating microscope is detected by detecting the emissive index 103 on the microscope by means of the digitizer 124 and computing the positional relation between the microscope and the detected index 103 by means of the WS 125. By doing this, the correlation with a two-dimensional preoperative tomographic image as a diagnostic image of the patient's body stored in the WS 125 can be obtained (the apparatus of this type is called a navigation apparatus).

Figure 20:
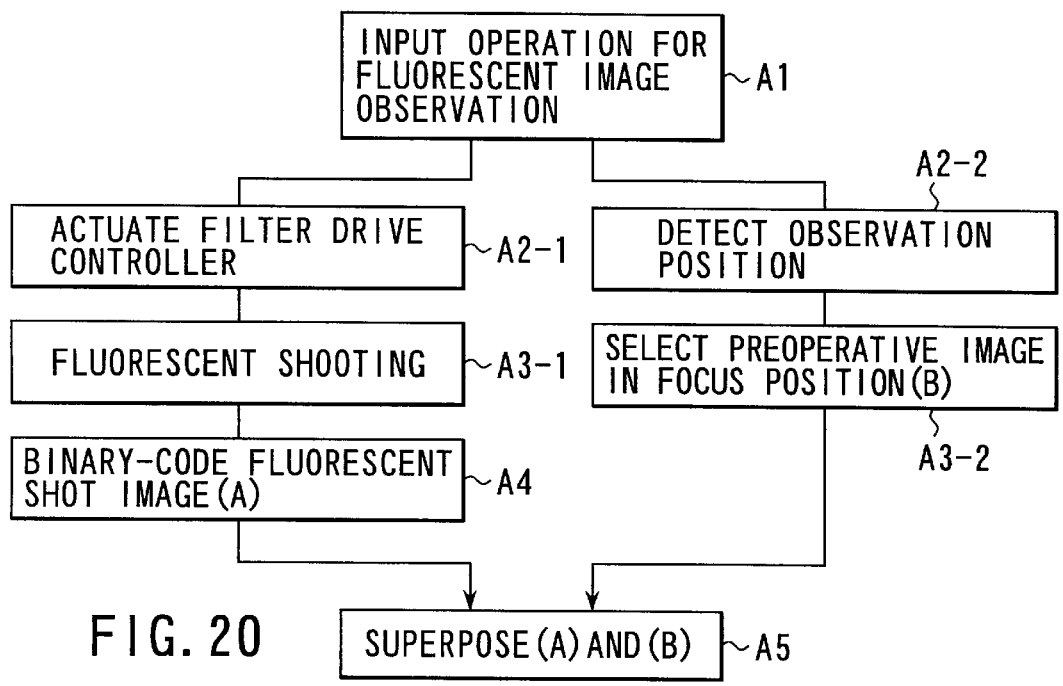
FIG. 20 is a chart for illustrating the operation of the invention.

FIG. 20 is a flowchart for illustrating the operation of the present invention. Since a method for simultaneously shooting the image based on the illumination light and the fluorescent image is described in detail in Jpn. Pat. Appln. KOKAI Publication No. 9-24052, only features of the present invention will be described in the following.

If the input switch 122 for fluorescent image observation is turned on (A1), the filter drive controller 123 controls the motors 111c and 119L3 (A2-1) to locate the excitation light transmitting filter 111b of the illumination light switching filter 111 and the cutoff filter 119L2 of the observational light switching filter 119L simultaneously on the optical axis.

Fluorescent shooting (A3-1) is carried out in this state. Light transmitted through the excitation light transmitting filter 111b of the illumination light switching filter 111 is applied to the affected region P, thereby inducing fluorescence. The illumination light and the excitation light is cut off by means of the cutoff filter 119L2 of the observational light switching filter 119L, and only the detected fluorescent image induced by the affected region P is reflected by the mirror 120L and landed on the image-pickup device 121L.

The detected fluorescent image incident upon the image-pickup device 121L is converted into a video signal by means of the video signal processor 128 and applied to the memory 129 and the mixer 130. The video signal that is applied to the memory 129 is binary-coded (A4). Thereafter, it is applied to the mixer 130 and displayed as a fluorescent observational image on the monitor 131.

If the motors 111c and 119L3 are controlled by means of the filter drive controller 123 so that the illumination light transmitting filter 111a of the illumination light switching filter 111 and the illumination light transmitting filter 119L1 of the observational light switching filter 119L are located simultaneously on the optical axis, the illumination light is applied to the affected region P, and an image of the affected region is landed on the image-pickup device 121L. This illumination light is processed by means of the video signal processor 128 and applied to the mixer 130.

AS this is done, a two-dimensional preoperative image that matches the observational position information (A2-2) on the affected region P obtained according to the emissive index 103, which is detected by means of the digitizer 124, and the magnification and focus information data on the operating microscope 101, which are transmitted from the microscope body controller 126 to the WS 125, is selected from ones that are previously recorded in the WS 125 (A3-2) and applied to the mixer 130.

The mixer 130 synthesizes (superposes) the video image based on the illumination light form the video signal processor 128, the fluorescent image binary-coded by means of the memory 129, and the preoperative image selected and inputted by means of the WS 125 (A5).

In these circumstances, the filter drive controller 123 selects the illumination light transmitting filter 111a and the illumination light transmitting filter 119L1 on illumination and shooting light paths, respectively. The image-pickup device 121L shoots an image in a normal or visible zone. A tumor position obtained by the aforesaid fluorescent observation and a tumor position based on the two-dimensional preoperative tomographic image selected by means of the WS 125 are superposed on the image of the affected region presently obtained by the operator and are displayed on the monitor 131.

FIG. 21 is a diagram for illustrating the way of synthesizing the fluorescent observational image and the two-dimensional preoperative tomographic image.

In an entire tumor image 142 as an affected region in an entire head image 141 of FIG. 21, a plane image (fluorescent observational image) 145a, based on a fluorescent image obtained from a certain curved surface in a surgical treatment position (exposed tumor portion 144), and a two-dimensional preoperative tomographic image 145b, selected as a microscopic observational position by the WS 125, can be synthesized and displayed on the monitor 131.

If the operator then moves the focal center position from B to C by focusing operation, the center of observation (center of the depth of focus) can be detected by means of the digitizer 124 and the WS 125 so that a corresponding tomographic image can be selected and synthesized with the aforesaid fluorescent observational image. In terminating the fluorescent observation, the operator is expected to turn off the input switch 122, thereby switching off the superposed display.

The fourth embodiment described above enjoys the following effects. Since an actual affected region has no flat surface, display of only a tomographic image as a diagnostic image in the microscopic observational position can hardly cover the state of the affected region. With use of the arrangement of the present embodiment, however, tomographic images based on the focusing operation for the present treatment position are superposed on the fluorescent observational image as they are displayed, so that the progress of a surgical operation and the conditions of a tumor can be recognized visually.

Further, the fluorescent observational image is superposed on the two-dimensional preoperative tomographic image as it is displayed. If the surgical operation is advanced according to the preoperative tomographic image, therefore, the operator can recognize supplementary correction of the position according to the fluorescent observational image during the operation. Thus, the correction is easy.

Since the mode for the superposed observation can be set by the input switch operation, moreover, the superposed observation can be selectively carried out as required. If only the external shape of the tumor portion is expected to be emphasized in the tomographic image from the WS, the operator can easily discriminate it by making its display color different from that of the fluorescent observational image.

Fifth Embodiment

Figure 22:
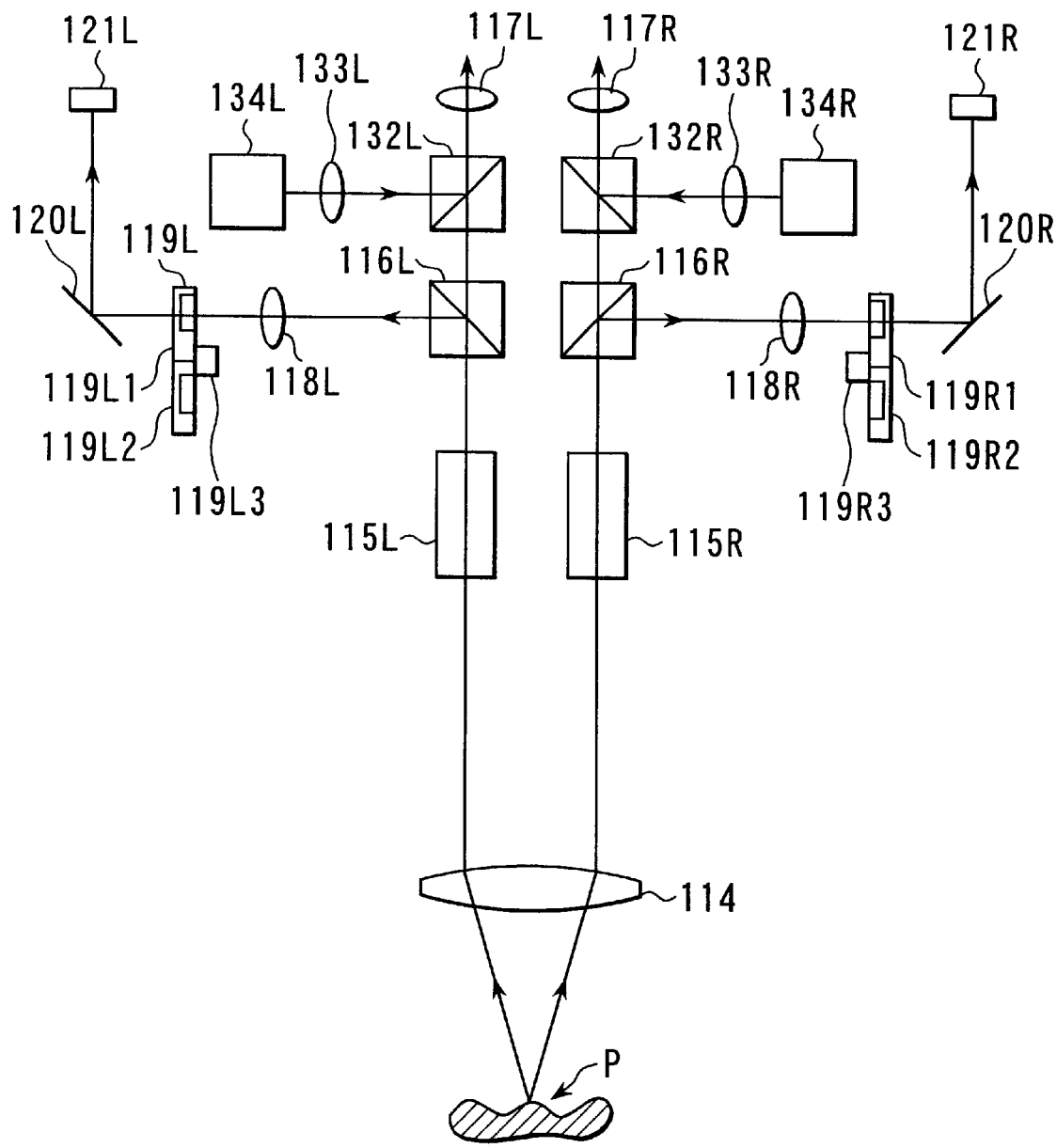
FIG. 22 is a view showing a configuration of an observational optical system according to a fifth embodiment of the invention.
Figure 23:
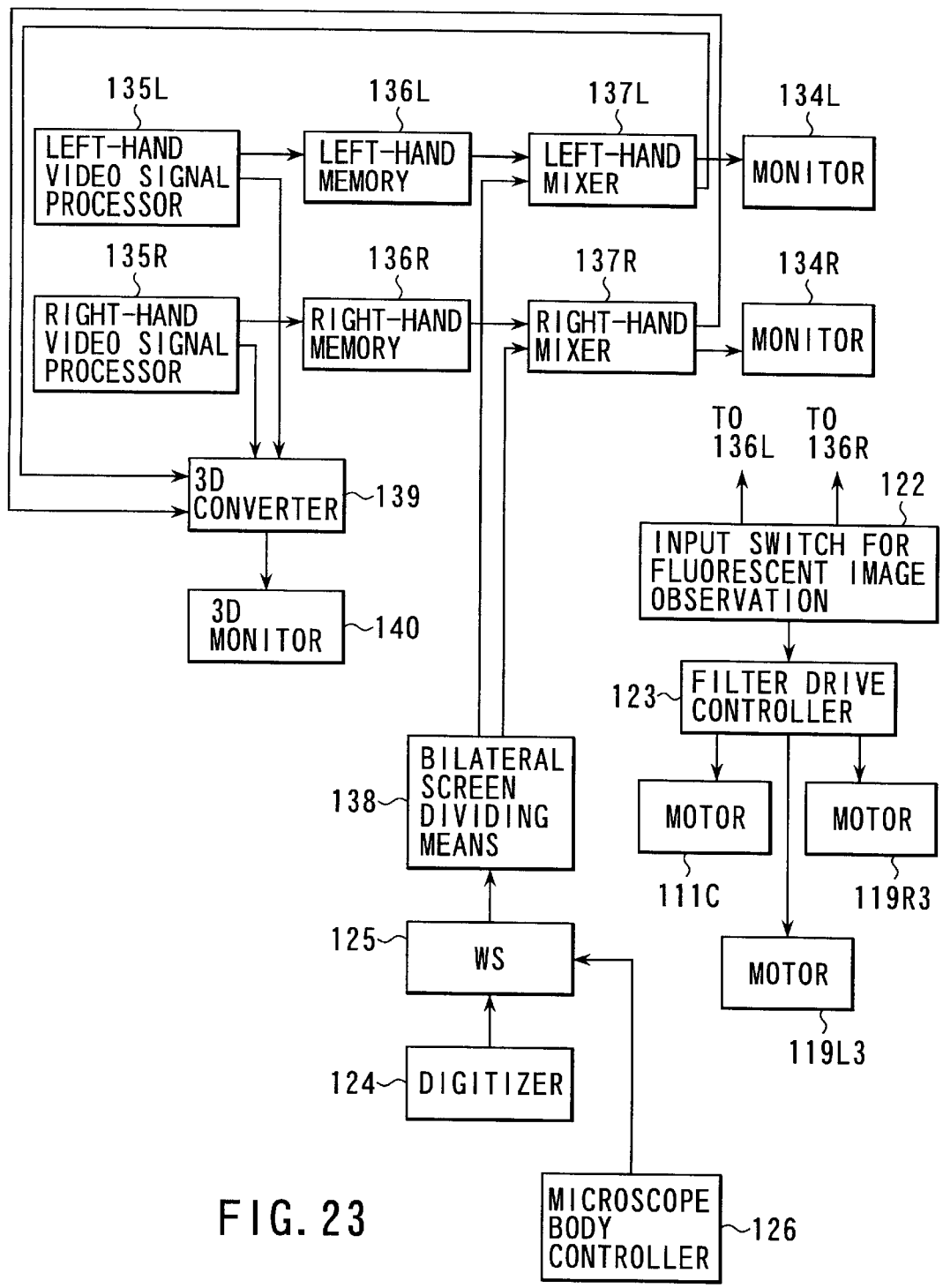
FIG. 23 is a general functional block diagram of an operating microscope.

FIGS. 22 and 23 show a configuration according to a fifth embodiment. Since left- and right-hand observational images of an affected region are processed in the same manner, the way of processing the left-hand observational image will now be described representatively.

AS in the case of the fourth embodiment, illumination or excitation light is applied to the affected region, and an image of the affected region is obtained by means of an image-pickup device 121L. The device 121L is connected to a video signal processor 135L for converting an image into a video signal. An output signal from the processor 135L is applied to a left-hand memory 136L. The memory 136L serves to binary-code the image, and its signal is applied to a left-hand mixer 137L that can superpose a plurality of video images. Output signals from the left-hand mixer 137L and a right-hand mixer 137R are applied to a 3D converter 139 to be converted into a three-dimensional video image thereby, whereupon the video image can be displayed on a 3D monitor 140.

Further, output signals from the left-hand video signal processor 135L and a right-hand video signal processor 135R are applied to the 3D converter 139 to be converted into a three-dimensional video image thereby, and the image can be displayed on the 3D monitor 140.

The WS 125 can apply the three-dimensional video image to bilateral screen dividing means 138, which can divide the three-dimensional video image into images with a lateral parallax. A left-hand video image is generated and applied to the left-hand mixer 137L. The mixer 137L is connected to a left-hand monitor 134L. Further, a lens 133L and a beam splitter 132L are arranged in order to guide the video image on the monitor 134L to the eyepiece 117L (see FIG. 22).

With the arrangement described above, fluorescence is excited, and the resulting fluorescent image is delivered to left- and right-hand image-pickup devices 121L and 121R, as in the case of the fourth embodiment. Since video images applied to the image-pickup devices 121L and 121R are processed in the same manner, only the processing on the left-hand side will now be described. The fluorescent image obtained by means of the image-pickup device 121L is applied to the left-hand video signal processor 135L to be converted into a video signal thereby, and applied to the left-hand memory 136L and the 3D converter 139.

In order to divide stereoscopic image information, based on the preoperative tomographic image information recorded in the WS 125, into images with a lateral parallax, moreover, the preoperative tomographic image is applied to the bilateral screen dividing means 138. In the left-hand mixer 137L, a left-hand image produced by the dividing means 138 is superposed on the signal from the left-hand memory 136L that binary-codes the signal from the left-hand video signal processor 135L.

A synthetic image delivered from the left-hand mixer 137L is applied to the 3D converter 139 and the left-hand monitor 134L. The converter 139 can convert the video image from the left- and right-hand mixers 137L and 137R into a three-dimensional image and display the image on the 3D monitor 140.

The light applied to the left-hand monitor 134L is guided to the eyepiece 117L via the lens 133L and the beam splitter 132L.

Figure 25:
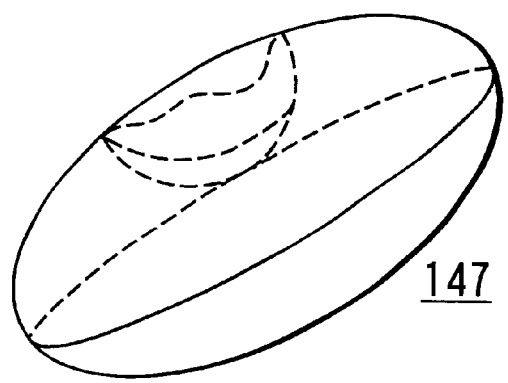
FIG. 25 is a three-dimensional exterior view of a tumor.

In this manner, the observational image of the affected region P based on the illumination light, the fluorescent observational image based on the application of the excitation light to the affected region, and the three-dimensional image based on the preoperative image can be simultaneously cast into the operator's field of vision and displayed on the 3D monitor 140. In this case, the present treated section information based on the fluorescent observational image is superposed three-dimensionally on a three-dimensional exterior view of a tumor (three-dimensional tumor image 147), such as the one shown in FIG. 25, so that the present progress of operation for the whole tumor can be recognized. In FIG. 25, the outline is formed by a position detecting function, and broken lines represent a stereoscopic affected region image based on the fluorescent observational image.

According to the fifth embodiment described above, the optical observational images obtained by microscopic observation are superposed, so that the present treatment position and progress of the affected region P in the whole tumor can be grasped three-dimensionally, and the direction of the treatment to be advanced thereafter can be recognized accurately. Dislocation of the preoperative tomographic image from the entire external shape can be also recognized, and it can be minutely corrected by stereoscopic observation. Thus, an environment can be provided for high-safety surgical operations.

Sixth Embodiment

Figure 24:
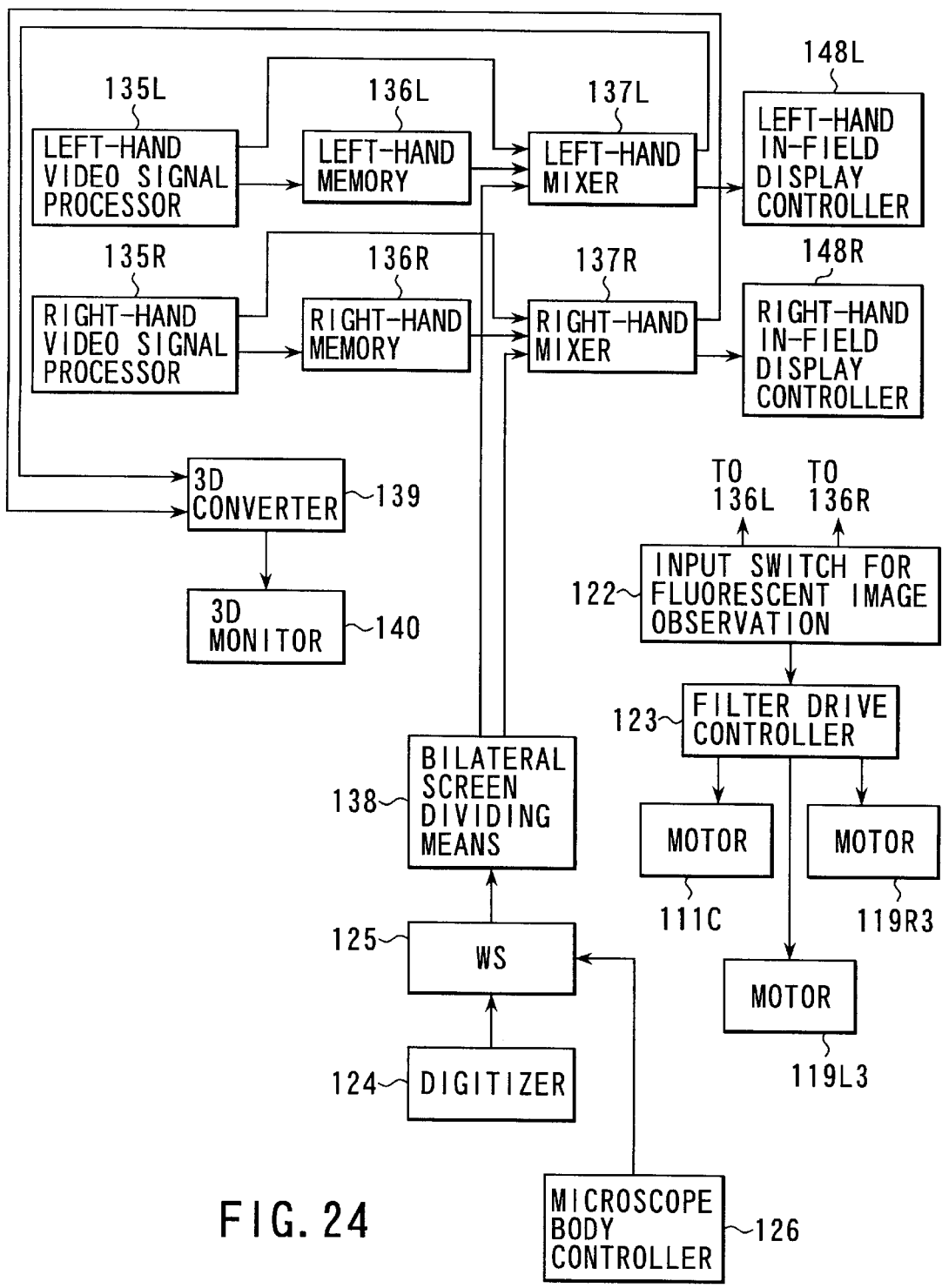
FIG. 24 is a general functional block diagram of an operating microscope according to a sixth embodiment of the invention.

The following is a description of only differences of a sixth embodiment of the present invention from the fifth embodiment. FIG. 24 is a diagram showing a configuration of the sixth embodiment. An image signal based on illumination light incident upon a left-hand video signal processor 135L is applied to a left-hand mixer 137L. In the sixth embodiment, the mixer 137L is connected to a left-hand in-field display controller 148L. The controller 148L is constructed in the same manner as an in-field display controller that constitutes an in-field display device (in-field display controller and lens tube portion) described with reference to FIG. 1 in Jpn. Pat. Appln. No. 10-248672. According to the sixth embodiment, the display according to the fifth embodiment is indicated and observed as an image display separate from the microscopic field.

In the arrangement described above, the image signal based on the illumination light incident upon the left-hand video signal processor 135L is applied to the left-hand mixer 137L. In the mixer 137L, a microscopic image based on the illumination light, a fluorescent image based on excitation light, and a preoperative image selected according to the outer peripheral surface of an affected region are synthesized and applied to the left-hand in-field display controller 148L. The video image applied to the controller 148L is displayed as an in-field display image by means of the in-field display device, and only an image based on the illumination light is visible as the microscopic image.

Figure 26:
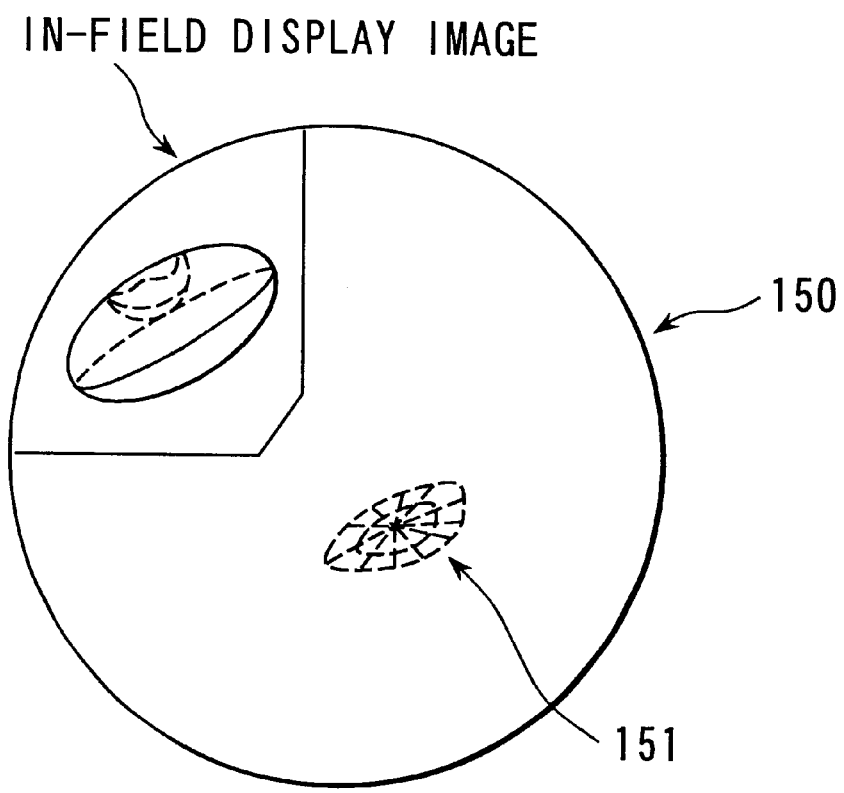
FIG. 26 is a view for illustrating the effect of the sixth embodiment of the invention.

The sixth embodiment described above has the following effects as well as the effects of the fifth embodiments. In the microscopic image based on the illumination light, as shown in FIG. 26, an exposed tumor portion 151 that cannot be recognized by the operator can be identified by being compared with the superposed in-field display image. Further, the three-dimensional shape of a tumor and the position of an affected region in the whole tumor can be grasped without screening a microscopic image 150 with the preoperative image and the fluorescent observational image.

Seventh Embodiment

Figure 27:
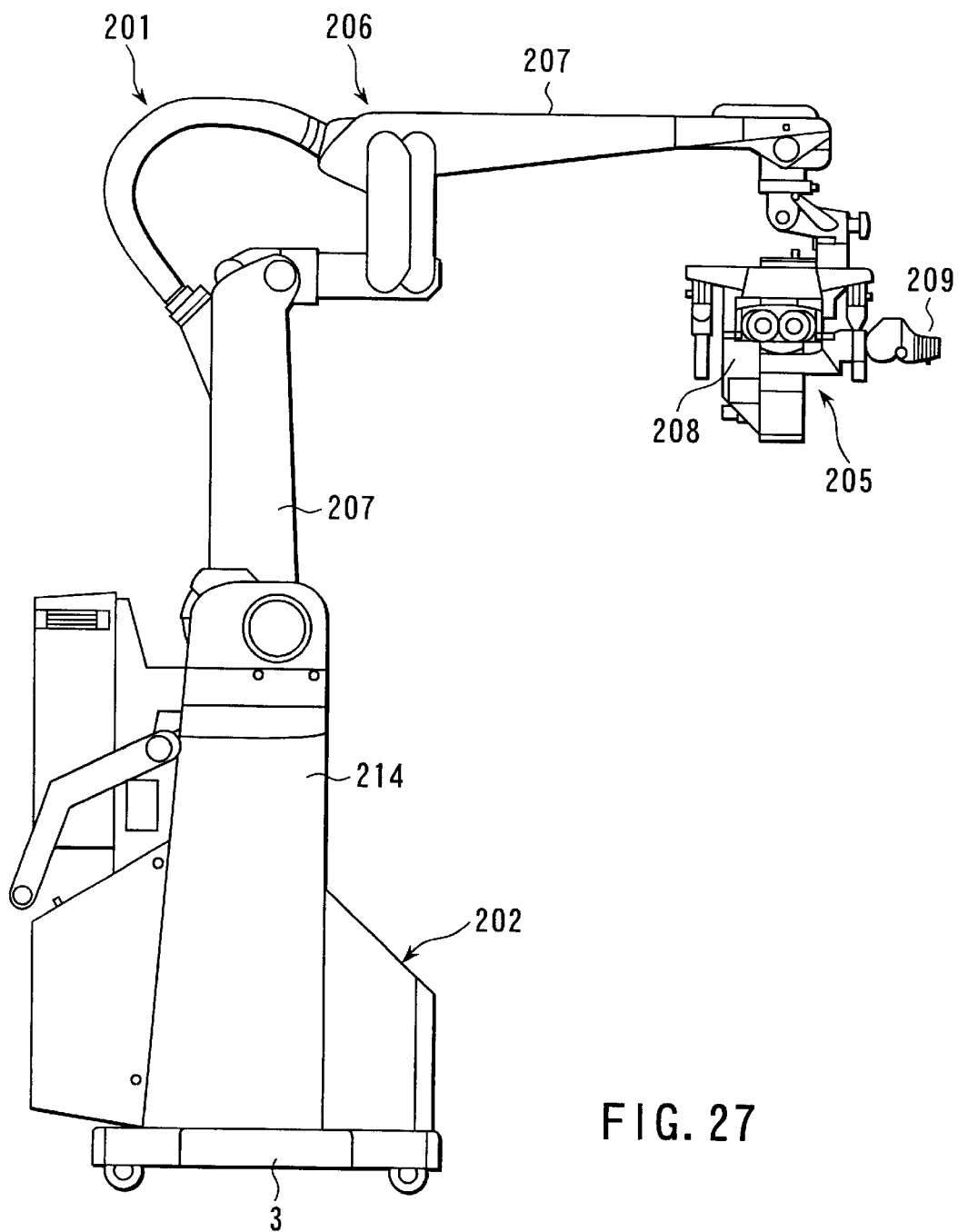
FIG. 27 is a side view showing the general external appearance of an operating microscope apparatus according to a seventh embodiment of the invention.

A seventh embodiment of the present invention will now be described with reference to FIGS. 27 to 35B. FIG. 27 shows the general external appearance of an operating microscope 201 of an operating microscope apparatus according to the present embodiment. A stand 202 of the operating microscope 201 of the present embodiment is provided with a base 203 movable on a floor surface and a support post 204 set up on the base 203.

Further, the support post 204 is provided, on its top portion, with a body 205 of the operating microscope 201, including an optical system for observing an affected region, and a support mechanism 206 for supporting the body 205 for movement in any desired direction. The mechanism 206 is a combination of a plurality of moving arms 207 for locating the microscope body 205 in a desired position.

Figure 28:
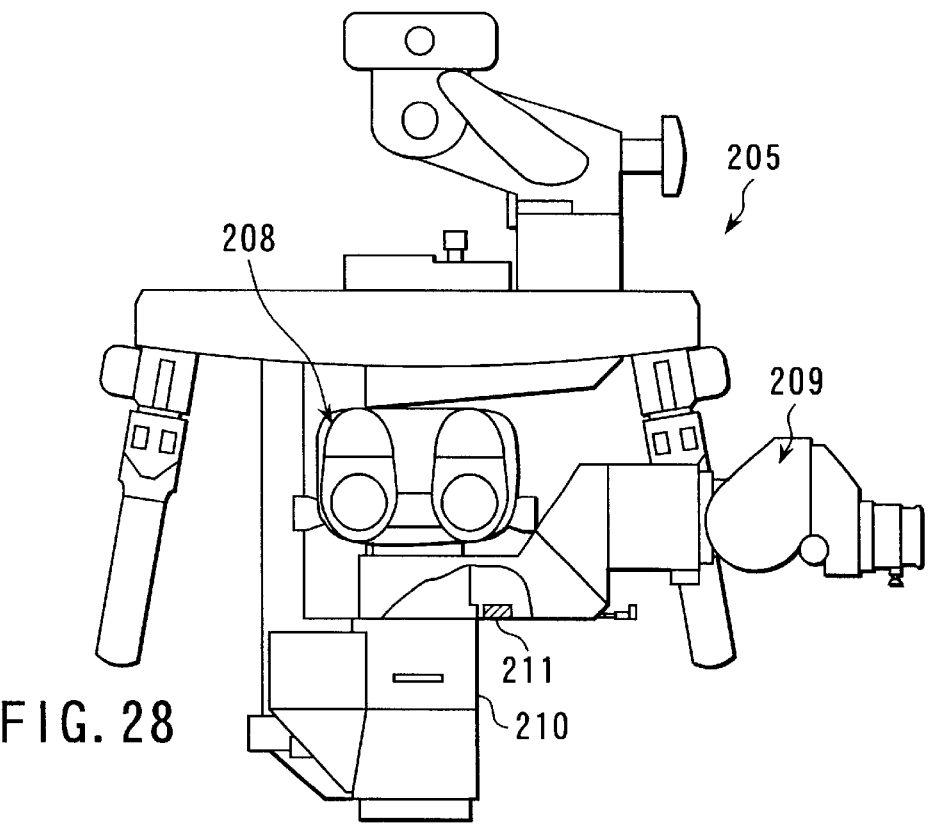
FIG. 28 is a side view showing a configuration of a microscope body of the operating microscope apparatus according to the seventh embodiment.

As shown in FIG. 28, moreover, the body 205 of the operating microscope 201 of the present embodiment is provided with an operator eyepiece unit 208 and a mate eyepiece unit 209. The body 205 is also provided with a barrel 210 for rotatably holding the mate eyepiece unit 209. The eyepiece unit 209 can be rotated with respect to the operator eyepiece unit 208 by means of the barrel 210.

Located near the barrel 210, moreover, is a position detecting encoder 211 that detects the rotational angle of the mate eyepiece unit 209 with respect to the operator eyepiece unit 208 and outputs it as an electrical signal.

Figure 29:
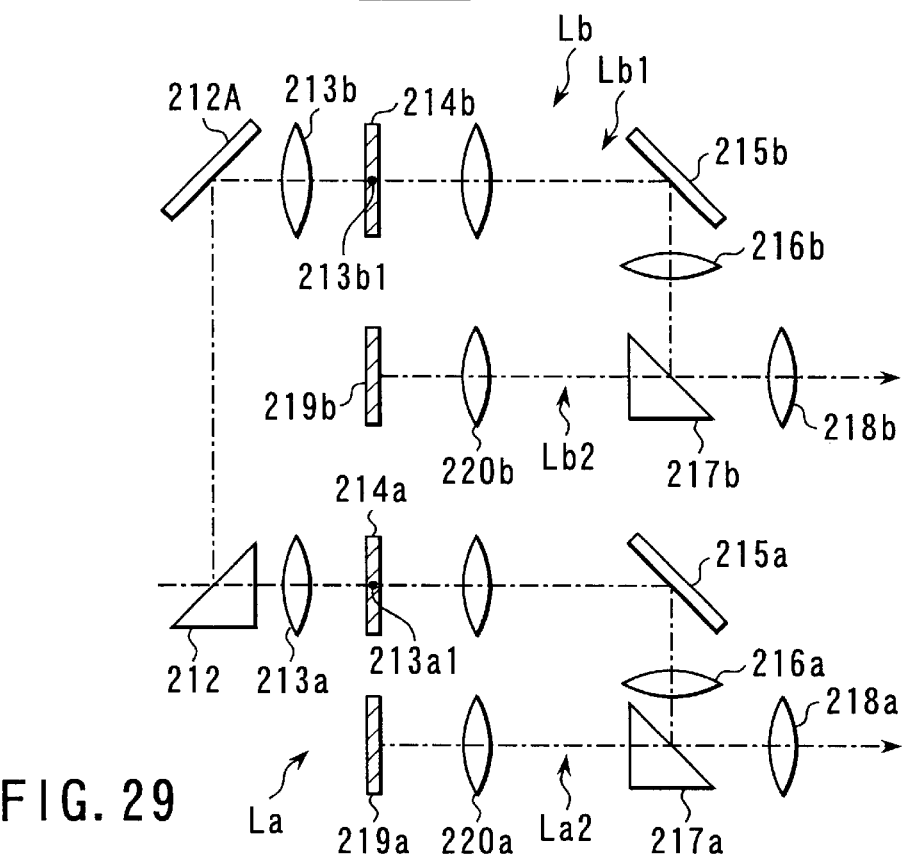
FIG. 29 is a schematic view of an optical system of the operating microscope apparatus according to the seventh embodiment.
Figure 30:
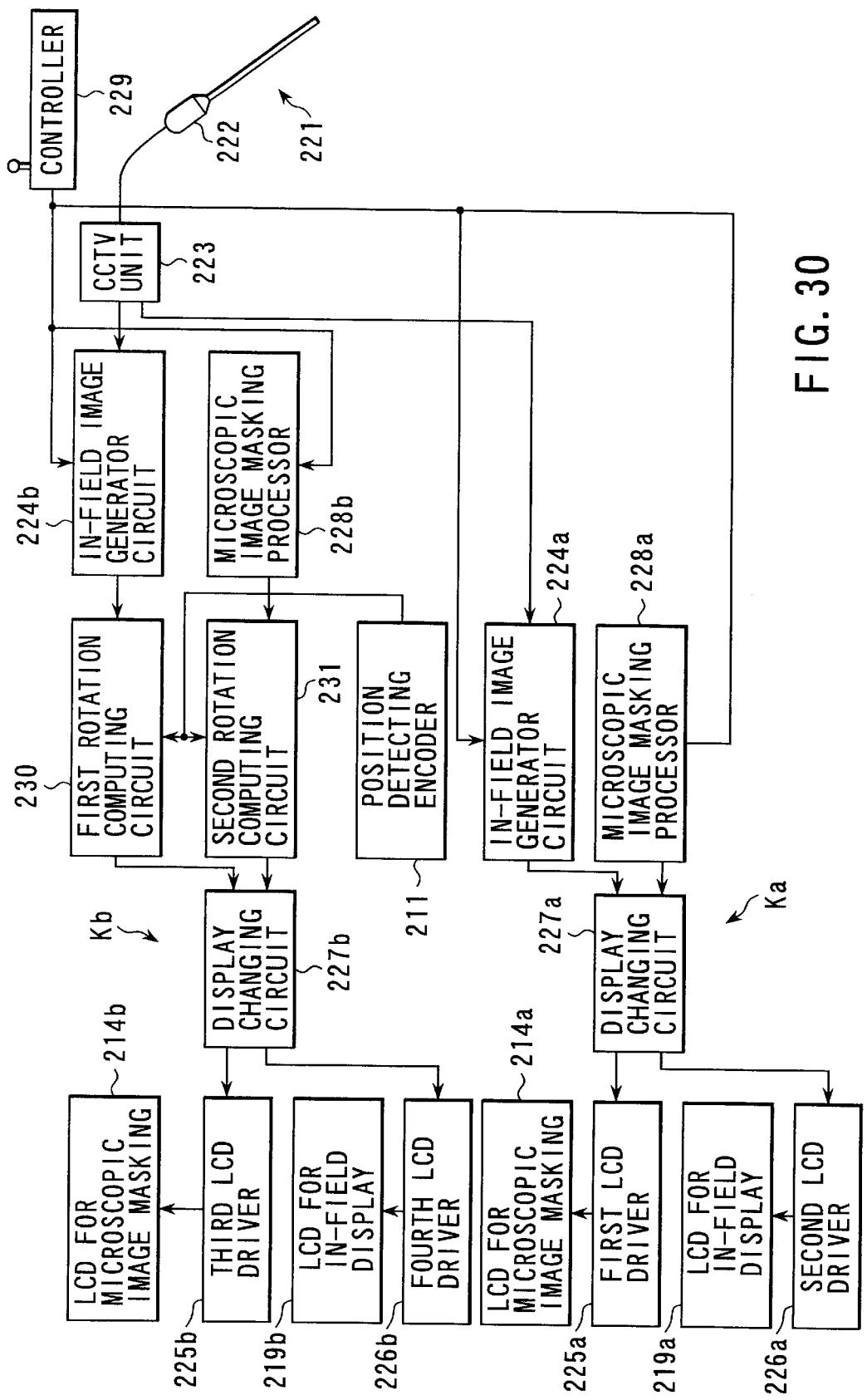
FIG. 30 is a block diagram of an electric circuit of the operating microscope apparatus according to the seventh embodiment.

FIG. 29 is a schematic view of an optical system of the body 205 of the operating microscope 201, and FIG. 30 is a block diagram of an electric circuit of the microscope 201. As shown in FIG. 29, the optical system of the body 205 of the operating microscope 201 according to the present embodiment is provided with a beam splitter 212 for dividing a microscopic image (incident light) into two parts for an operator-side optical system La and a mate-side optical system Lb. The light incident upon the beam splitter 212 is divided into two light beams, transmitted and reflected. The transmitted and reflected light beams, divided from the microscopic image by means of the beam splitter 212, are landed on the operator- and mate-side optical systems La and Lb, respectively.

Further, the operator-side optical system La includes a main image display optical system La1 for displaying a main microscopic image and an in-field display optical system La2 for projecting an index and a sub-image, which is different from the main image, on a part of the microscopic field. The main image display optical system La1 is provided with an objective lens 213a, LCD 214a for microscopic image masking, total-reflection mirror 215a, imaging lens 216a, prism 217a, and eyepiece 218a. The LCD 214a is located on a first imaging point 213a1 of the objective lens 213a.

The in-field display optical system La2 is provided with an LCD (in-field monitor) 219a for in-field display, imaging lens 220a, prism 217a, and eyepiece 218a. The prism 217a and the eyepiece 218a are used in common in the main image display optical system La1 and the in-field display optical system La2. The microscopic image from the main image display optical system La1 and an in-field display image from the in-field display optical system La2 are superposed and landed on the side of the eyepiece 218a by means of the prism 217a.

Likewise, the mate-side optical system Lb includes a main image display optical system Lb1 for displaying a main microscopic image and an in-field display optical system Lb2 for projecting an index and a sub-image, which is different from the main image, on a part of the microscopic field. The main image display optical system Lb1 is provided with an objective lens 213b, LCD 214b for microscopic image masking, total-reflection mirror 215b, imaging lens 216b, prism 217b, and eyepiece 218b. The LCD 214b is located on a first imaging point 213b1 of the objective lens 213b.

The in-field display optical system Lb2 is provided with an LCD (in-field monitor) 219b for in-field display, imaging lens 220b, prism 217b, and eyepiece 218b. The prism 217b and the eyepiece 218b are used in common in the main image display optical system Lb1 and the in-field display optical system Lb2. The microscopic image from the main image display optical system Lb1 and an in-field display image from the in-field display optical system Lb2 are superposed and landed on the side of the eyepiece 218b by means of the prism 217b.

In the operating microscope 201 according to the present embodiment, an endoscopic image from an endoscope 221 shown in FIG. 30 is displayed on the respective LCD's 219a and 219b for in-field display of the operator- and mate-side optical systems La and Lb. A TV camera head 222 is coupled to the endoscope 221. A CCTV unit 223 is connected to the camera head 222. The endoscopic image of the endoscope 221 is picked up by means of the camera head 222, and the resulting optical video image is photoelectrically converted by means of an image-pickup device (not shown) in the camera head 222. Thereafter, the image is applied as an electrical signal to the CCTV unit 223 and processed, whereupon a TV signal is outputted.

As shown in FIG. 30, moreover, an electric circuit block of the operating microscope 201 according to the present embodiment is provided with an operator-side processing system Ka and a mate-side processing system Kb. The CCTV unit 223 is connected with an in-field image generator circuit 224a of the operator-side processing system Ka and an in-field image generator circuit 224b of the mate-side processing system Kb.

The operator-side processing system Ka is provided with a first LCD driver 225a for driving the LCD 214a for microscopic image masking, a second LCD driver 226a for driving the LCD 219a for in-field display, a display changing circuit 227a, the in-field image generator circuit 224a, and a microscopic image masking processor 228a. Further, the in-field image generator circuit 224a and the microscopic image masking processor 228a are connected with an in-field display controller (input means) 229 for inputting observation conditions in which the size, position, etc. of images to be displayed on the LCD's 219a and 219b for in-field display are changed.

Furthermore, the in-field image generator circuit 224a and the microscopic image masking processor 228a are connected to the input side of the display changing circuit 227a. The first and second LCD drivers 225a and 226a are connected to the output side of the circuit 227a.

The output of the CCTV unit 223 is applied to the in-field image generator circuit 224a of the operator-side processing system Ka, the output of which is applied to the display changing circuit 227a. An output signal from the microscopic image masking processor 228a is also applied to the circuit 227a, the output of which is applied to the LCD drivers 225a and 226a. Further, output signals from the LCD drivers 225a and 226a are applied to the LCD 214a for microscopic image masking and the LCD 219a for in-field display, respectively.

The mate-side processing system Kb is provided with a third LCD driver 225b for driving the LCD 214b for microscopic image masking, a fourth LCD driver 226b for driving the LCD 219b for in-field display, a display changing circuit 227b, the in-field image generator circuit 224b, and a microscopic image masking processor 228a. Further, the in-field image generator circuit 224b and the microscopic image masking processor 228b are connected with the in-field display controller 229.

In the mate-side processing system Kb according to the present embodiment, moreover, a first rotation computing circuit (observational state changing means) 230 is interposed between the in-field image generator circuit 224b and the display changing circuit 227b, while a second rotation computing circuit (observational state changing means) 231 is interposed between the microscopic image masking processor 228b and the display changing circuit 227b.

The first and second rotation computing circuits 230 and 231 are connected to the input side of the display changing circuit 227b. Further, the third and fourth LCD drivers 225b and 226b are connected to the output side of the circuit 227b.

On the side of the mate-side processing system Kb, the output of the CCTV unit 223 is applied to the in-field image generator circuit 224b of the mate-side processing system Kb, the output of which is applied to the display changing circuit 227b via the first rotation computing circuit 230. A signal from the microscopic image masking processor 228b is also applied to the display changing circuit 227b via the second rotation computing circuit 231. The output of the circuit 227b is applied to the LCD drivers 225b and 226b. Further, output signals from the drivers 225b and 226b are applied to the LCD 214b for microscopic image masking and the LCD 219b for in-field display, respectively.

The position detecting encoder 211 is connected to the first and second rotation computing circuits 230 and 231. An output signal from the encoder 211 is applied to the circuits 230 and 231, while the control output of the in-field display controller 229 is applied to the in-field image generator circuits 224a and 224b and the microscopic image masking processors 228a and 228b.

Figure 31A:
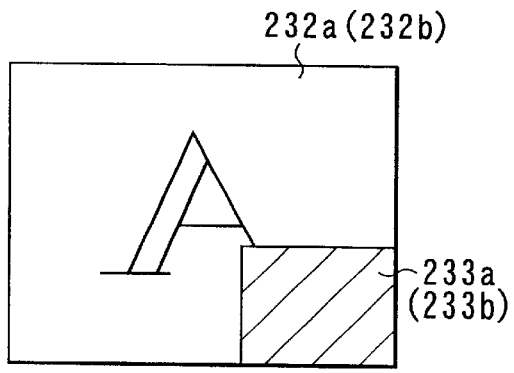
FIG. 31A is a plan view showing a state in which a mask portion is inserted in a microscopic image of an operator-side optical system of the operating microscope apparatus according to the seventh embodiment.
Figure 74:
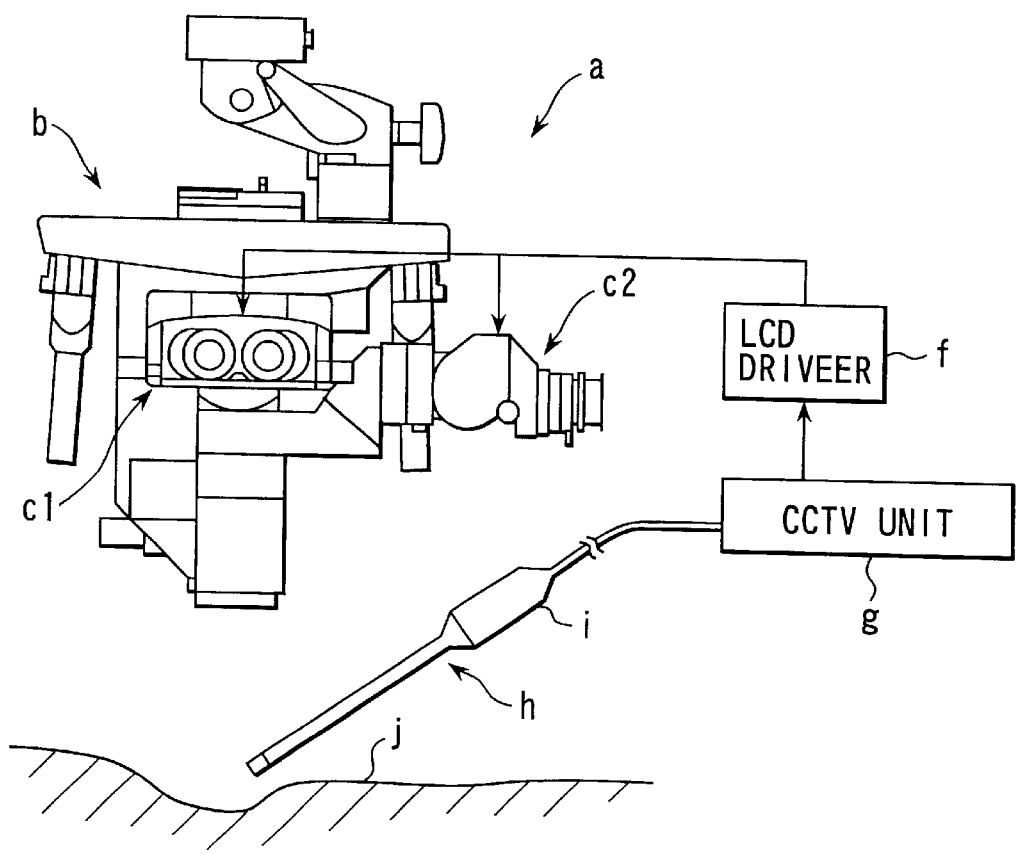
FIG. 74 is a schematic view showing a configuration of the principal part of a conventional operating microscope apparatus.
Figure 75A:
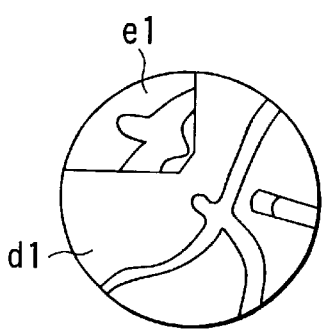
FIGS. 75A and 75B are plan views individually showing in-field images displayed in operator and mate eyepiece units, respectively, of an operating microscope of the conventional operating microscope apparatus.
Figure 75B:
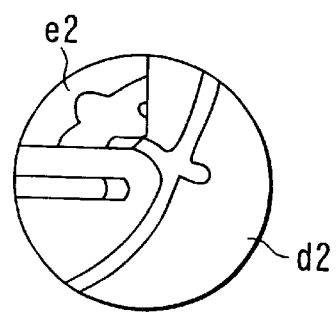

The following is a description of the function of the operating microscope 201. In starting the operation of the operating microscope 201 of the present embodiment, a microscopic image of an affected region in an operative field j (see FIG. 74) as an object of surgical operation is divided into two parts for the operator- and mate-side optical systems La and Lb by means of the beam splitter 212. The divided image for the operator-side optical system La is focused on the first imaging point 213a1 of the objective lens 213a, whereupon a microscopic image 232a for the optical system La is formed, as shown in FIG. 31A. Further, the image for the mate-side optical system Lb, divided by means of the beam splitter 212, is focused on the first imaging point 213b1 of the objective lens 213b, whereupon a microscopic image 232b for the optical system Lb is formed, as shown in FIG. 31A.

In FIG. 30, the endoscopic image shot by means of the endoscope 221 is picked up by means of the camera head 222. The resulting optical video image is photoelectrically converted by means of the image-pickup device (not shown) in the camera head 222. Thereafter, the image is applied as an electrical signal to the CCTV unit 223 and processed, whereupon a TV signal is outputted. The TV signal delivered from the CCTV unit 223 is applied to the respective in-field image generator circuits 224a and 224b of the operator- and mate-side processing system Ka and Kb.

The output signal processed in the in-field image generator circuit 224a of the operator-side processing system Ka is applied to the display changing circuit 227a. As this is done, the output signal from the microscopic image masking processor 228a is also applied to the circuit 227a. Further, the output signal from the circuit 227a is applied to the LCD drivers 225a and 226a. The control signals from the LCD drivers 225a and 226a are applied to the LCD 214a for microscopic image masking and the LCD 219a for in-field display, respectively.

Since the LCD 214a for microscopic image masking is located on the first imaging point 213a1 of the objective lens 213a, a mask portion 233a for sub-image is inserted into a part of the microscopic image 232a for the operator-side optical system La by means of the LCD 214a, as shown in FIG. 31A. As this is done, moreover, an endoscopic image 234a is partially displayed on a part of the whole LCD screen of the LCD 219a for in-field display, and the remaining part is left as a shielding portion 235a, as shown in FIG. 31B.

Figure 31B:
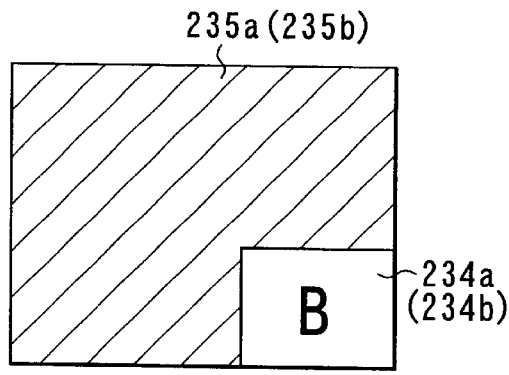
FIG. 31B is a plan view showing plan view showing a state in which an endoscopic image is partially displayed on an in-field image.
Figure 32A:
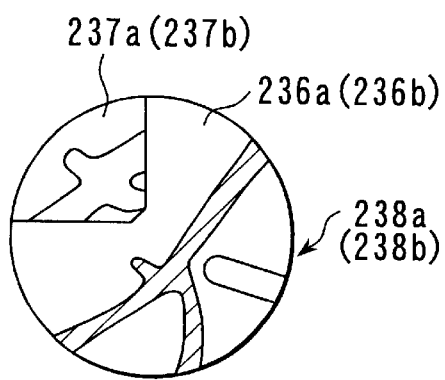
FIGS. 32A and 32B show in-field images in a state such that endoscopic images are inserted individually in operator- and mate-side microscopic images of the operating microscope apparatus according to the seventh embodiment.

The image of FIG. 31A that combines the microscopic image 232a and the mask portion 233a for sub-image inserted therein and the image of FIG. 31B that combines the endoscopic image 234a and the shielding portion 235a are superposed by means of the prism 217a. Thereupon, a composite image 238a is formed having an endoscopic image (sub-image) 237a inserted in a microscopic image (main image) 236a, as shown in FIG. 32A.

The same operation on the operator side is also carried out on the mate side. More specifically, the output signal processed in the in-field image generator circuit 224b of the mate-side processing system Kb is applied to the display changing circuit 227b through the first rotation computing circuit 230. As this is done, the output signal from the microscopic image masking processor 228b is also applied to the circuit 227b through the second rotation computing circuit 231.

Further, the output signal from the circuit 227b is applied to the LCD drivers 225b and 226b. The output signals from the LCD drivers 225b and 226b are applied to the LCD 214a for microscopic image masking and the LCD 219a for in-field display, respectively.

Since the LCD 214b for microscopic image masking is located on the first imaging point 213b1 of the objective lens 213b, a mask portion 233b for sub-image is inserted into a part of the microscopic image 232b for the mate-side optical system Lb by means of the LCD 214b, as shown in FIG. 31A. As this is done, moreover, an endoscopic image 234b is partially displayed on a part of the whole LCD screen of the LCD 219b for in-field display, and the remaining part is left as a shielding portion 235b, as shown in FIG. 31B.

The image of FIG. 31A that combines the microscopic image 232b and the mask portion 233b for sub-image inserted therein and the image of FIG. 31B that combines the endoscopic image 234b and the shielding portion 235b are superposed by means of the prism 217b. Thereupon, a composite image 238b is formed having an endoscopic image (sub-image) 237b inserted in a microscopic image (main image) 236b, as shown in FIG. 32A.

As the in-field display controller 229 is operated, the observation conditions in which the size, position, etc. of the images to be displayed on the LCD's 219a and 219b for in-field display are changed are inputted. Depending on the conditions inputted by means of the controller 229, the in-field image generator circuits 224a and 224b output control signals for changing the size, position, etc. of the images to be displayed on the LCD's 219a and 219b.

In the microscopic image masking processors 228a and 228b, moreover, the mask portions 233a and 233b are formed having the same size and position as the endoscopic images 234a and 234b that are generated by means of the in-field image generator circuits 224a and 224b, as shown in FIG. 31A. Thus, the mask portion 233a of FIG. 31A and the endoscopic image 234a of FIG. 31B are equal in size.

Figure 31C:
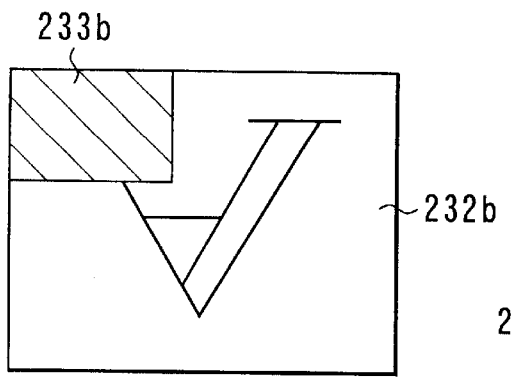
FIGS. 31C and 31D are plan views showing images obtained by rotating the images of FIGS. 31A and 31B, respectively.
Figure 31D:
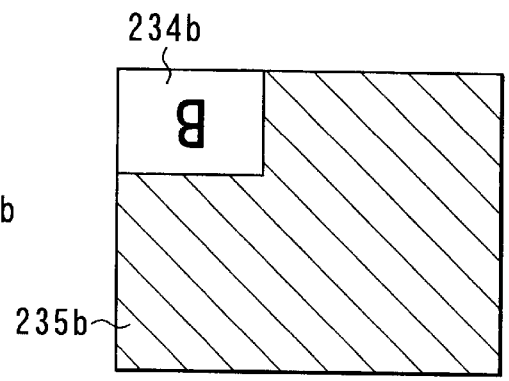

According to the present embodiment, furthermore, two images are alternatively changed by means of the display changing circuit 227a by the operator's processing, and images are displayed individually on the LCD's 214a and 219a by means of the LCD drivers 225a and 226a. In the mate-side processing system, the images of FIGS. 31A and 31B, generated by means of the in-field image generator circuit 224b and the microscopic image masking processor 228b, are subjected to map conversion in the rotation computing circuits 230 and 231 in accordance with the output of the position detecting encoder 211 that detects the rotational angle of the mate eyepiece unit 209, and then rotated in the manner shown in FIGS. 31C and 31D. The images shown in FIGS. 31C and 31D are obtained by rotating the images of FIGS. 31A and 31B, respectively, for 1800.

Figure 32B:
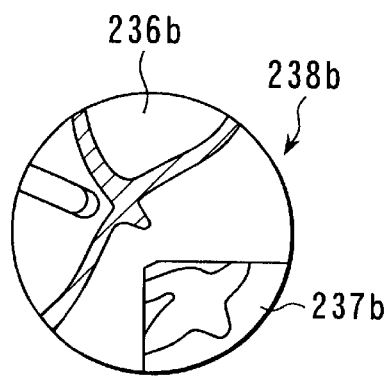

The mate-side image processed in this manner forms the composite image 238b of FIG. 32B, which is an image obtained by rotating the composite image 238a of FIG. 32A without changing the relative positions of the microscopic images 236a and 2326b and the endoscopic images 237a and 237b therein.

Figure 33A:
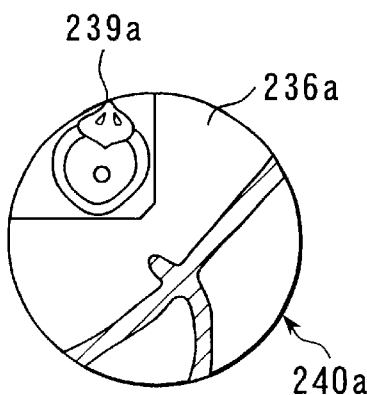
FIGS. 33A and 33B are plan views showing operator- and mate-use microscopic images, respectively, in the operating microscope apparatus according to the seventh embodiment.
Figure 33B:
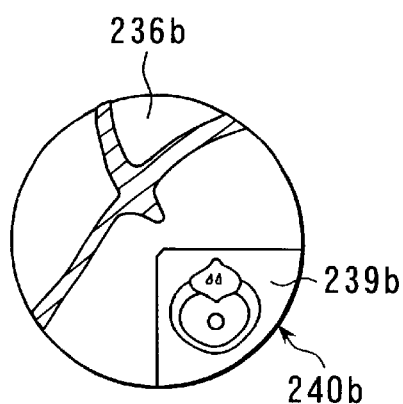

The following is a description of operation for the case where preoperative diagnostic images, such as X-ray CT's, are displayed on the LCD's 219a and 219b for in-field display of the operator- and mate-side optical systems La and Lb. According to the present embodiment, computer images, such as X-ray CT's (not shown), are applied to the in-field image generator circuits 224a and 224b of FIG. 30. In this case, the output of the circuit 224b is applied directly to the display changing circuit 227b without actuating the rotation computing circuits 230 and 231 of the mate-side processing system Kb. In consequence, composite images 240a and 240b are obtained including computer images 239a and 239b inserted in the microscopic images 236a and 2326b, as shown in FIGS. 33A and 33B, respectively. FIGS. 33A and 33B show the operator- and mate-use composite images 240a and 240b, respectively. The computer images 239a and 239b, which serve as in-field images in the microscopic images 236a and 236b, are common to the operator- and mate-use composite images 240a and 240b, and are displayed in like manner in a fixed direction.

Figure 35A:
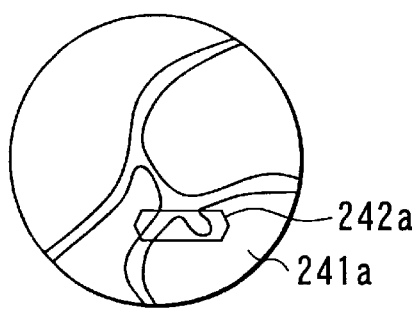
FIGS. 35A and 35B are plan views showing indexes superposed individually on the operator- and mate-use microscopic images, respectively, in the operating microscope apparatus according to the seventh embodiment.
Figure 35B:
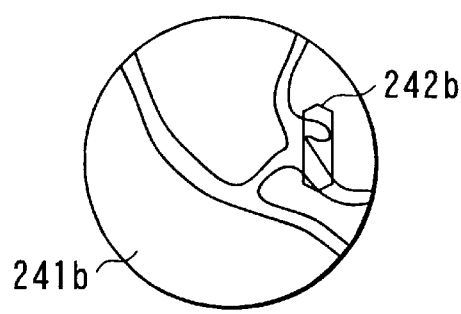

FIGS. 35A and 35B show states in which indexes (markers) 242a and 242b are overlaid on microscopic images 241a and 241b, respectively. The microscopic images 241a and 241b are used on the operator side and on the mate side, respectively.

Figure 34A:
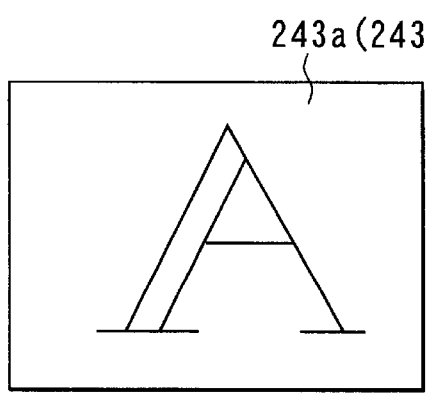
FIGS. 34A and 34B are plan views showing a mask image and a in-field display image, respectively, obtained when an index is overlaid on each microscopic image in the operating microscope apparatus according to the seventh embodiment.
Figure 34B:
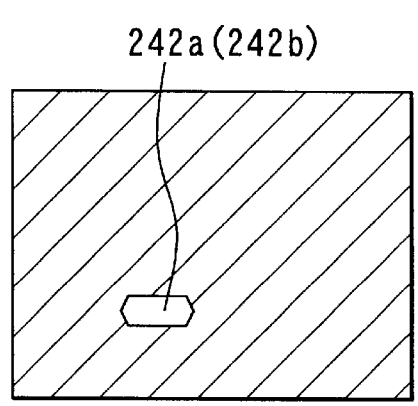

Further, FIG. 34A shows a mask image 243a or 243b overlain by the index 242a or 242b, and FIG. 34B shows an in-field display image. In this case, the mask size for the mask image 243a or 243b is reduced to zero, so that the index 242a or 242b appears as the in-field display image. The microscopic images 241a and 241b obtained in this case have their corresponding indexes 242a and 242b superposed thereon, as shown in FIGS. 35A and 35B, respectively.

If the mask portion 233a or 233b is larger than the endoscopic image 234a or 234b in FIGS. 31A to 31D, the endoscopic image 234a or 234b in the field has a frame (not shown). If the mask portion 233a or 233b is smaller than the endoscopic image 234a or 234b, on the other hand, the periphery of the endoscopic image 234a or 234b in the field is blurred.

In the case where the endoscopic image 234a or 234b in the field of the microscopic image 232a or 232b represents a graphic form, such as a line or circle, the graphic form is replaced with the microscopic image 232a or 232b if the mask portion 233a or 233b has the same shape as the in-field endoscopic image 234a or 234b. Overlay display is made if the mask portion 233a or 233b need not be formed.

The arrangement described above produces the following effects. In the mate-side processing system Kb according to the present embodiment, the first rotation computing circuit 230 is interposed between the in-field image generator circuit 224b and the display changing circuit 227b, while the second rotation computing circuit 231 is interposed between the microscopic image masking processor 228b and the display changing circuit 227b. Further, the position detecting encoder 211 for detecting the rotational angle of the mate eyepiece unit 209 with respect to the operator eyepiece unit 208 is connected to the first and second rotation computing circuits 230 and 231. If the mate eyepiece unit 209 is rotated with respect to the operator eyepiece unit 208 with the in-field image of an auxiliary optical system projected into the microscopic field so that the composite image 238a or 238b is formed including the endoscopic image 237a or 237b inserted in the microscopic 236a or 236b, as shown in FIG. 32A, therefore, the images of FIGS. 31A and 31B that are generated by means of the in-field image generator circuit 224b and the microscopic image masking processor 228b of the mate-side processing system Kb are subjected to map conversion in the rotation computing circuits 230 and 231 in accordance with the output of the position detecting encoder 211 that detects the rotational angle of the mate eyepiece unit 209, and then rotated in the manner shown in FIGS. 31C and 31D. Accordingly, the composite image 238b of FIG. 32B is displayed on the mate eyepiece unit 209 with the composite image 238a of FIG. 32A displayed on the operator eyepiece unit 208. If the mate eyepiece unit 209 is rotated with respect to the operator eyepiece unit 208, therefore, a microscopic field of the same positional relations for the operator can be continuously secured for the mate. Thus, the in-field image of the auxiliary optical system produces no dead angles in the microscopic field.

If necessary, moreover, an image in the same direction as the one on the operator side can be projected on the in-field image of the auxiliary optical system on the mate side by a simple method, or the in-field image can be displayed with a desired size and in a free position. Further, an index such as a marker overlaid on the microscopic image, as well as the in-field image of the auxiliary optical system, can be realized by only the image processing without changing the system configuration, so that a lot of types of display and observation methods can be selected without entailing any troublesome manipulation during the surgical operation. In consequence, necessary in-field information can be properly offered to the operator or his or her mate, and the aimed microscopic field can be easily secured during the operation.

Eighth Embodiment

Figure 36:
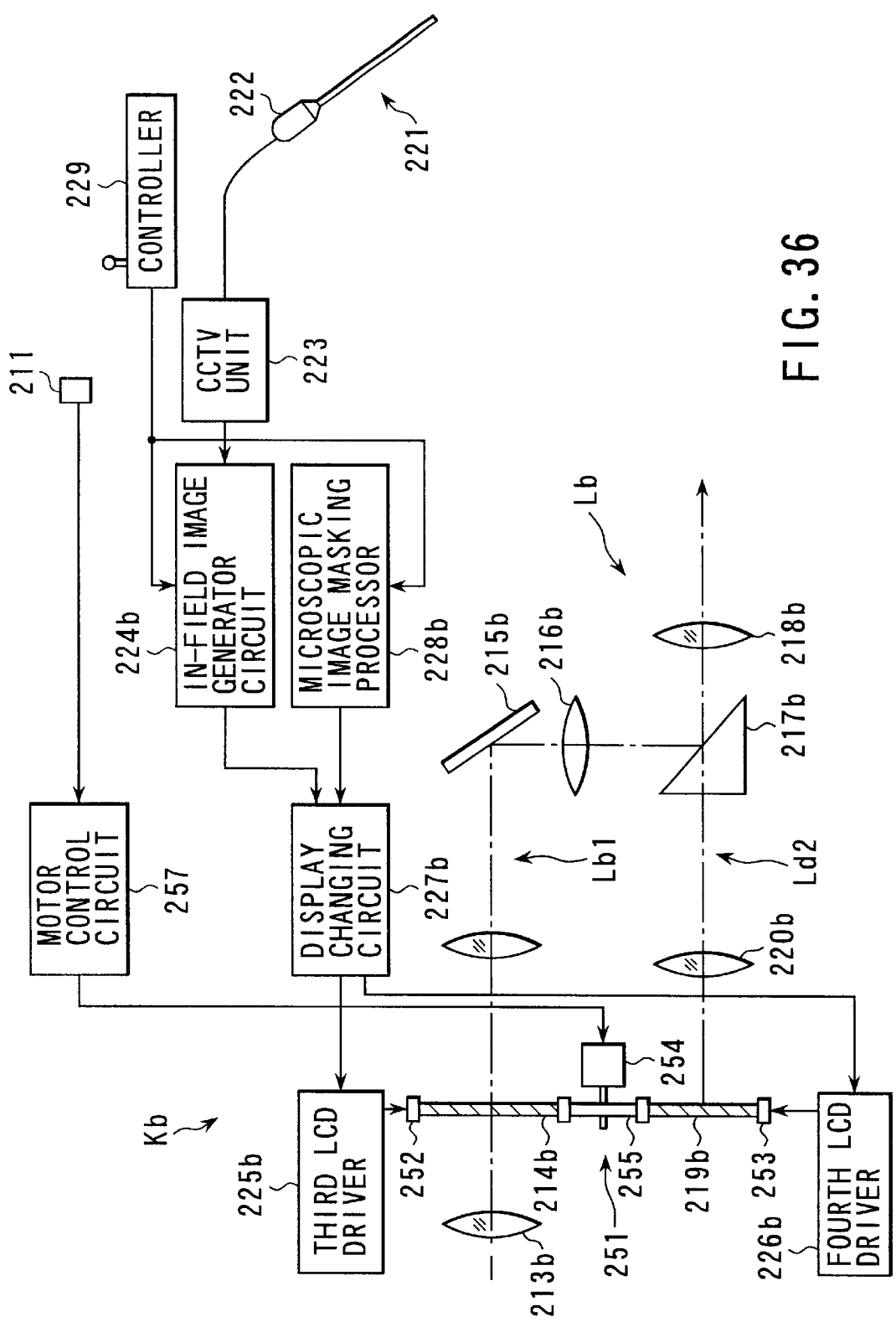
FIG. 36 is a schematic view of a mate-side optical system of an operating microscope apparatus according to an eighth embodiment of the invention.
Figure 37:
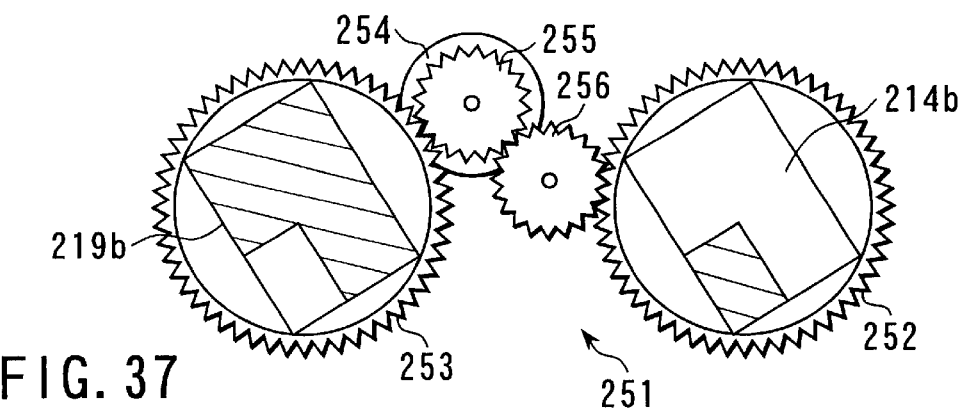
FIG. 37 is a plan view showing an outline of a drive mechanism for a microscopic image mask LCD of the operating microscope apparatus according to the eighth embodiment.

FIGS. 36 and 37 show an eighth embodiment of the present invention. In the present embodiment, the configuration of the mate eyepiece unit 209 of the seventh embodiment is modified in the following manner.

According to the present embodiment, the rotation computing circuits 230 and 231 in the mate-side processing system Kb of the seventh embodiment are omitted or replaced with an LCD rotating mechanism 251 for rotating the LCD 214b for microscopic image masking and the LCD 219b for in-field display in the mate-side optical system Lb.

As shown in FIG. 37, the LCD rotating mechanism 251 of the present embodiment comprises a ring-shaped first LCD driving gear 252, to which the LCD 214b for microscopic image masking is fixed, and a ring-shaped second LCD driving gear 253, to which the LCD 219b for in-field display is fixed. The LCD 214b for microscopic image masking is fixed in the ring of the first LCD driving gear 252. Likewise, the LCD 219b for in-field display is fixed in the ring of the second LCD driving gear 253.

A gear 255 is fixed to the rotating shaft of a drive motor 254 of the LCD rotating mechanism 251. The gear 255 is in mesh with an intermediate gear 256 as well as with the second LCD driving gear 253. Further, the intermediate gear 256 is in mesh with the first LCD driving gear 252. The gear ratio between the gears 255 and 256 is adjusted to 1:1. Thus, the first and second LCD driving gears 252 and 253 can rotate in the same direction and at the same speed as the gear 255 rotates.

A motor control circuit 257 is connected to the drive motor 254. A position detecting encoder 211 is connected to the circuit 257. An output signal from the encoder 211 is applied to the circuit 257, whereby the operation of the motor 254 is controlled.

The following is a description of the operation of the present embodiment arranged in this manner. If a mate eyepiece unit 209 is rotated with respect to an operator eyepiece unit 208, according to the present embodiment, the output signal from the position detecting encoder 211, corresponding to the rotational angle of the mate eyepiece unit 209, is applied to the motor control circuit 257. Thus, the circuit 257 controls the operation of the drive motor 254.

As this is done, the motor 254 causes the gear 255 to rotate according to the rotational angle of the mate eyepiece unit 209. The second LCD driving gear 253 is rotated in association with the rotation of the gear 255, and the first LCD driving gear 252 is rotated through the medium of the intermediate gear 256. Since the gear ratio between the gears 255 and 256 is adjusted to 1:1, the first and second LCD driving gears 252 and 253 rotate in the same direction and at the same speed. Accordingly, the positional relation between the LCD 219b for in-field display and the LCD 214b for microscopic image masking can be kept fixed, and image display equivalent to the one obtained by the image rotation shown in FIGS. 31C and 31D can be realized.

According to the present embodiment, therefore, the output signal from the position detecting encoder 211 that detects the rotational angle of the mate eyepiece unit 209 is applied to the motor control circuit 257, and the operation of the drive motor 254 is controlled by means of the circuit 257. Thus, if the mate eyepiece unit 209 is rotated with respect to the operator eyepiece unit 208, according to the present embodiment, the LCD rotating mechanism 251 is driven according to the rotational angle o the mate eyepiece unit 209 by means of the motor 254, so that the LCD 214b for microscopic image masking and the LCD 219b for in-field display in the mate-side optical system Lb can be rotated individually. According to the present embodiment, therefore, a lot of types of display and observation methods can be selected without entailing any troublesome manipulation during the surgical operation, as in the case of the first embodiment, and besides, the in-field image can be offered without lowering the image quality during image computation for the image rotating process.

Ninth Embodiment

Figure 38A:
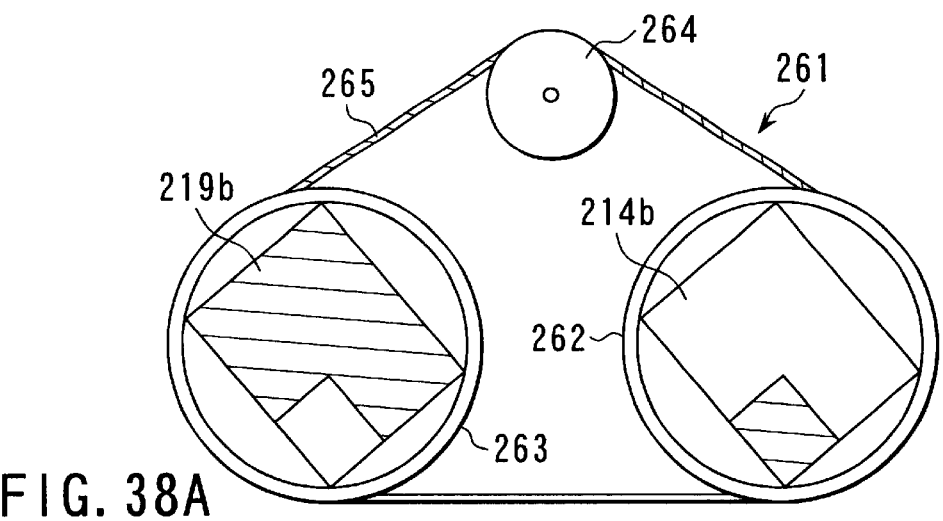
FIG. 38A is a plan view showing an outline of a drive mechanism for a microscopic image mask LCD of an operating microscope apparatus according to a ninth embodiment of the invention.

FIG. 38A shows a ninth embodiment of the present invention. In the present embodiment, the LCD rotating mechanism 251 of the eighth embodiment is modified in the following manner.

The LCD rotating mechanism 251 of the eighth embodiment is designed so that the LCD 214b for microscopic image masking and the LCD 219b for in-field display in the mate-side optical system Lb are rotated individually by means of the gear mechanism. However, the present embodiment is provided with an LCD rotating mechanism 261 that is formed of a belt drive mechanism.

The LCD rotating mechanism 261 of the present embodiment comprises a first LCD driving pulley 262, to which the LCD 214b for microscopic image masking is fixed, and a second LCD driving pulley 263, to which the LCD 219b for in-field display is fixed.

A pulley 264 is fixed to the rotating shaft of a drive motor (not shown) of the LCD rotating mechanism 261. Further, an endless belt 265 is passed around and between the pulley 264 and the first and second LCD driving pulleys 262 and 263. The driving pulleys 262 and 263 are equal in diameter. Thus, the first and second LCD driving pulleys 262 and 263 can rotate in the same direction and at the same speed.

As in the case of the eighth embodiment, moreover, the motor control circuit 257 (see FIG. 36) is connected to the drive motor for the pulley 264. The position detecting encoder 211 is connected to the circuit 257. An output signal from the encoder 211 is applied to the circuit 257, whereby the operation of the drive motor is controlled.

The following is a description of the operation of the present embodiment arranged in this manner. If a mate eyepiece unit 209 is rotated with respect to an operator eyepiece unit 208, according to the present embodiment, the output signal from the position detecting encoder 211, corresponding to the rotational angle of the mate eyepiece unit 209, is applied to the motor control circuit 257. Thus, the circuit 257 controls the operation of the drive motor.

As this is done, the motor causes the pulley 264 to rotate according to the rotational angle of the mate eyepiece unit 209, and the first and second LCD driving pulleys 262 and 263 are rotated in the same direction and at the same speed by means of the belt 265. Accordingly, the positional relation between the LCD 219b for in-field display and the LCD 214b for microscopic image masking can be kept fixed, and image display equivalent to the one obtained by the image rotation shown in FIGS. 31C and 31D can be realized. Thus, the present embodiment can provide the same effects of the second embodiment.

Tenth Embodiment

Figure 38B:
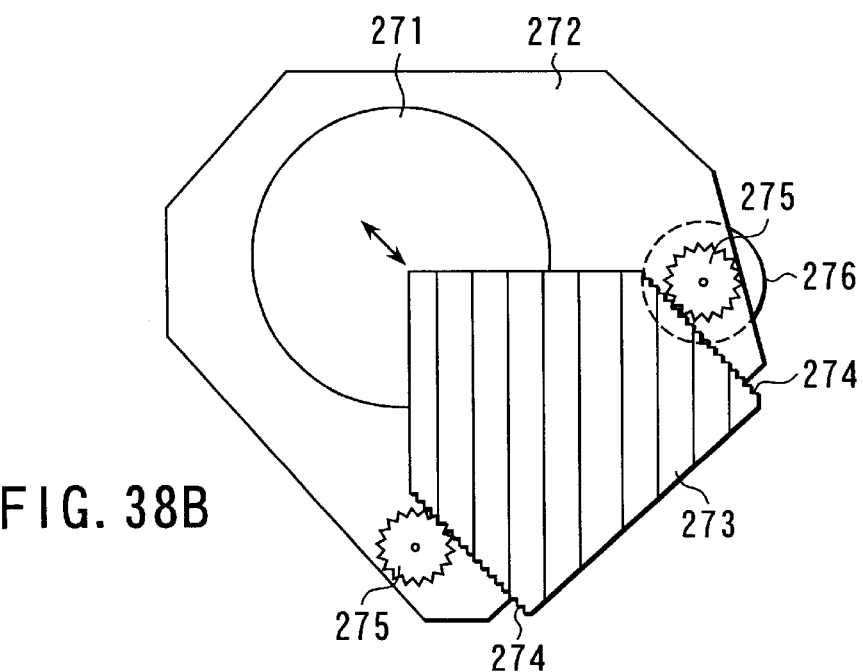
FIG. 38B is a plan view showing an outline of a drive mechanism for a microscopic image mask LCD of an operating microscope apparatus according to a tenth embodiment of the invention.

FIG. 38B shows a tenth embodiment of the present invention. In the present embodiment, the respective configurations of the operator- and mate-side LCD's 214a and 214b for microscopic image masking of the seventh embodiment are modified in the following manner.

As shown in FIG. 38B, the present embodiment is provided with a support frame 272 that has a circular window 271. The window 271 of the frame 272 is located on the first imaging point 213a1 of the objective lens 213a.

A shielding plate 273 is movably supported on the support frame 272 so as to cover a part of the circular window 271. Further, racks 274 are formed individually on the opposite sides of the shielding plate 273. The racks 275 are in mesh with driving gears 275, individually. The gears 275 are fixed to the rotating shaft of a motor 276. As the gears 275 rotate, the shielding plate 273 is advanced or retreated so as to cover a part of the window 271 of the frame 272.

The following is a description of the operation of the present embodiment arranged in this manner. According to the present embodiment, the drive of the motor 276 is controlled by means of a control signal delivered from in-field display range setting means (not shown). As the motor 276 rotates, the gear 275 rotates. In association with the rotation of the gear 275, the shielding plate 273 moves in the direction of the arrow in FIG. 38B, whereupon the area of the part of the circular window 271 that is covered by the support frame 272 is changed. Thus, the microscopic image masking area is changed.

The arrangement described above also fulfills the same functions of the operator- and mate-side LCD's 214a and 214b for microscopic image masking of the seventh embodiment. Thus, the present embodiment can provide the same effects of the seventh embodiment.

Eleventh Embodiment

Figure 39:
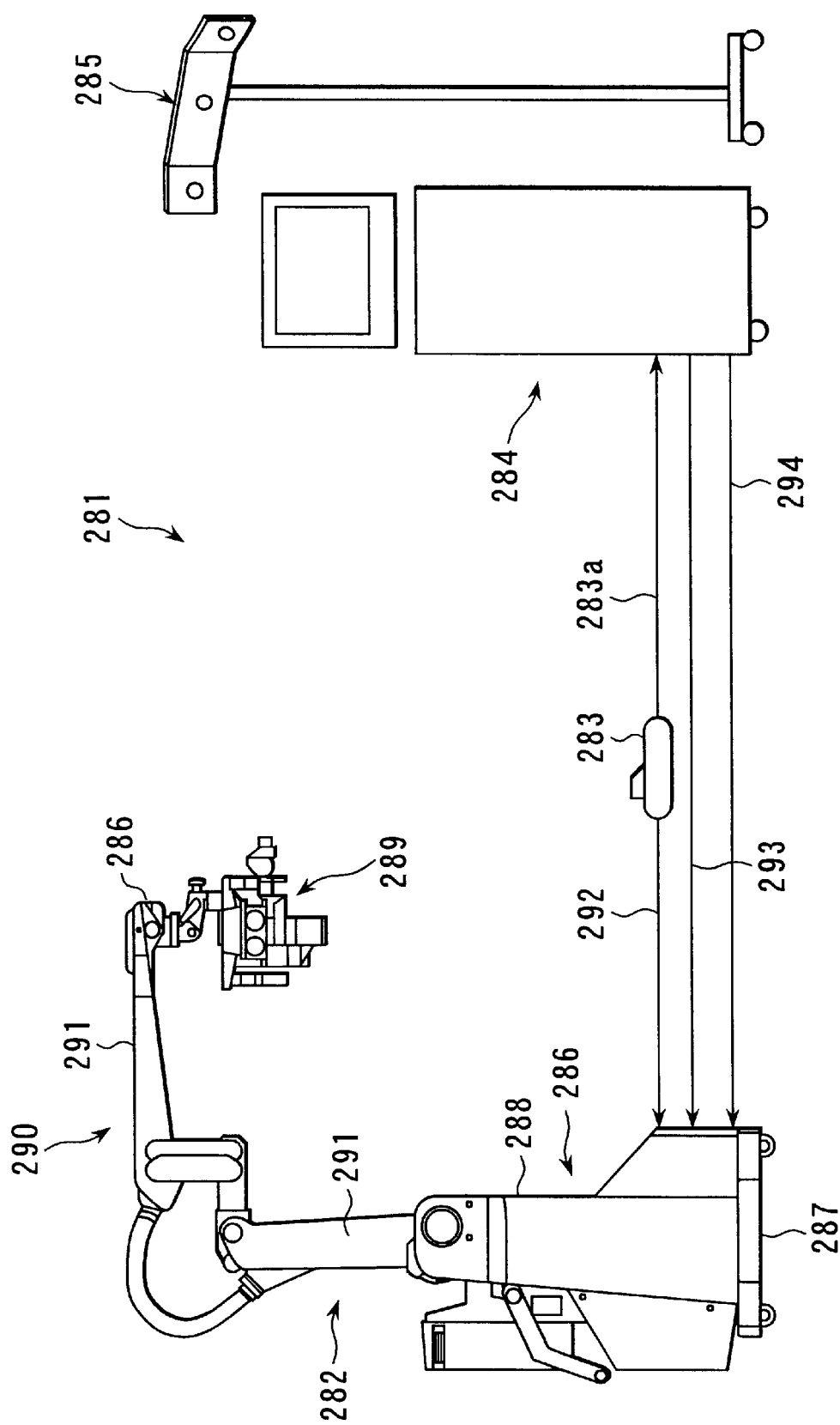
FIG. 39 is a general schematic view of an operating microscope apparatus according to an eleventh embodiment of the invention.

FIGS. 39 to 42B show an eleventh embodiment of the present invention. FIG. 39 shows an outline of the whole system of an operating microscope apparatus 281 according to the present embodiment.

The operating microscope apparatus 281 of the present embodiment comprises an operating microscope 282 constructed substantially in the same manner as the operating microscope 201 of the seventh embodiment, index/in-field display controller 283, position information computing means 284, and position detecting means 285 for detecting the position of the operating microscope 282.

A stand 286 of the operating microscope 282 of the present embodiment is provided with a base 287 movable on a floor surface and a support post 288 set up on the base 287.

Further, the support post 288 is provided, on its top portion, with a body 289 of the operating microscope 282, including an optical system for observing an affected region, and a support mechanism 290 for supporting the body 289 for movement in any desired direction. The mechanism 290 is a combination of a plurality of moving arms 291 for locating the microscope body 289 in a desired position.

Furthermore, the microscope 282 is connected with the index/in-field display controller 283, position information computing means 284, and position detecting means 285. The microscope 282 is supplied with an index/in-field display control signal 292 from the controller 283 and a position information computing means image signal 293 and an arm driving signal 294 from the computing means 284.

Figure 40A:
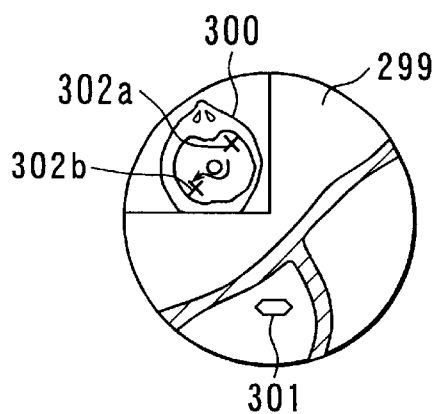
FIG. 40A is a plan view showing a microscopic image in an operating microscope apparatus according to the eleventh embodiment.
Figure 40B:
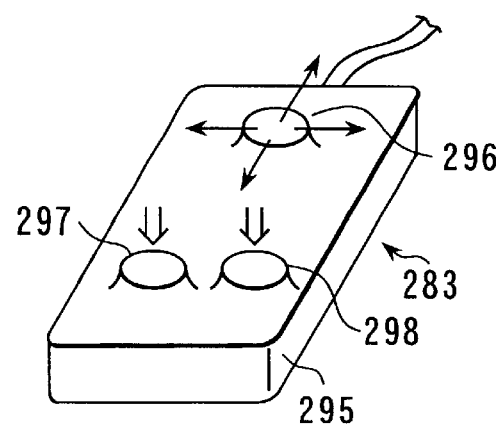
FIG. 40B is a perspective view showing an index/in-field display controller.

FIG. 40B is an exterior view of the index/in-field display controller 283. A body 295 of the controller 283 is provided with a joystick 296 and two switches 297 and 298. An index control signal 283a is delivered from the controller 283 to the position information computing means 284.

FIG. 40A shows a microscopic image 299 of the operating microscope 282. A position information computing means image 300 and a marker 301 are displayed in the field of the microscopic image 299. Two indexes 302a and 302b are displayed in the image 300.

The following is a description of the operation of the present embodiment. According to the present embodiment, the microscope 282 is supplied with the position information computing means image signal 293 from the position information computing means 284. The image signal 293 is displayed as an in-field display image 304 on an LCD 303 for in-field display, as shown in FIG. 41B. A preoperative image, such as an X-ray CT, is displayed in the in-field display image 304. Further, the indexes 302a and 302b are displayed in the image 304, while the marker 301 is displayed on the LCD 303.

Figure 41A:
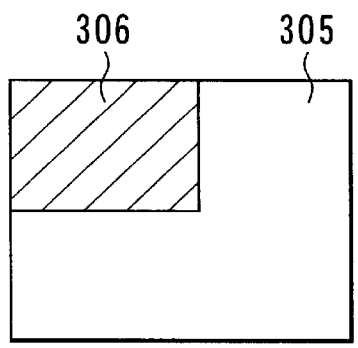
FIG. 41A is a plan view showing a state in which a microscopic image mask as large as an in-field display image is displayed on a microscopic image mask LCD of the operating microscope apparatus according to the eleventh embodiment.
Figure 41B:
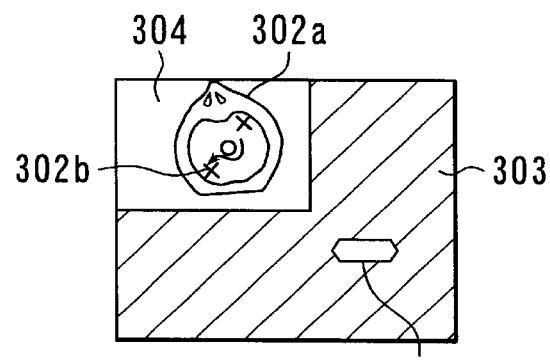
FIG. 41B is a plan view showing a state in which an index and a marker are displayed on the in-field display image.
Figure 42A:
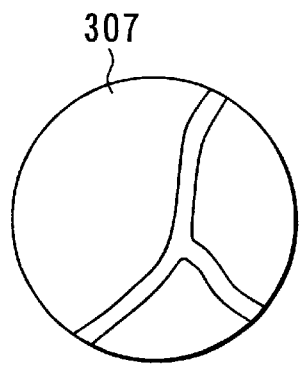
FIG. 42A is a plan view showing a microscopic image in the operating microscope apparatus according to the eleventh embodiment.
Figure 42B:
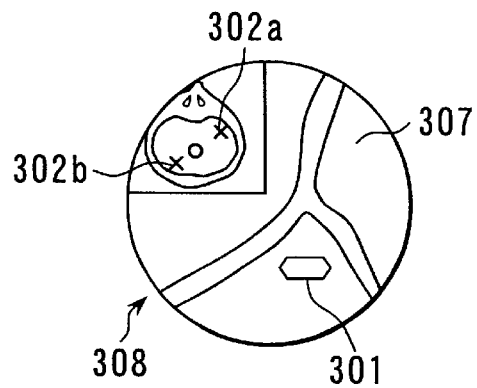
FIG. 42B is a plan view showing a state in which an index and a marker are displayed on the microscopic image by superposition.

A microscopic image mask 306, which is as large as the in-field display image 304, is displayed on an LCD 305 for microscopic image masking shown in FIG. 41A. A microscopic image 308 shown in FIG. 42B is superposed on a microscopic image 307 shown in FIG. 42A.

Referring to FIG. 40A, the index 302a in the position information computing means image 300, an MIR or X-ray CT diagnostic image, and the marker 301 in the field of the microscopic image 299 are pointed in the same direction in the operative field.

The joystick 296 and switches 297 and 298 of the controller 283 of FIG. 40B are operated to transmit the index control signal 283a to the position information computing means 284. Based on this information, the control means 284 transmits the image, moved to the indexes 302a and 302b, as shown in FIG. 40A, to the microscope 282 in response to the position information computing means image signal 293, and displays the image in the in-field display image 304 of the microscope 282.

Further, the position information computing means 284 controls the support mechanism 290 of the microscope 282 in response to the arm driving signal 294, thereby moving the microscope body 289 so that the index 302b and the marker 301 are situated in the same position in the operative field.

According to the present embodiment arranged in this manner, the operator can designate his or her desired view point on a position information computing means image, and the observational position can be automatically moved to the point. Thus, the field of vision can be easily moved to a target region during the surgical operation.

Twelfth Embodiment

FIGS. 43 to 47 show a twelfth embodiment of the present invention.

Figure 43:
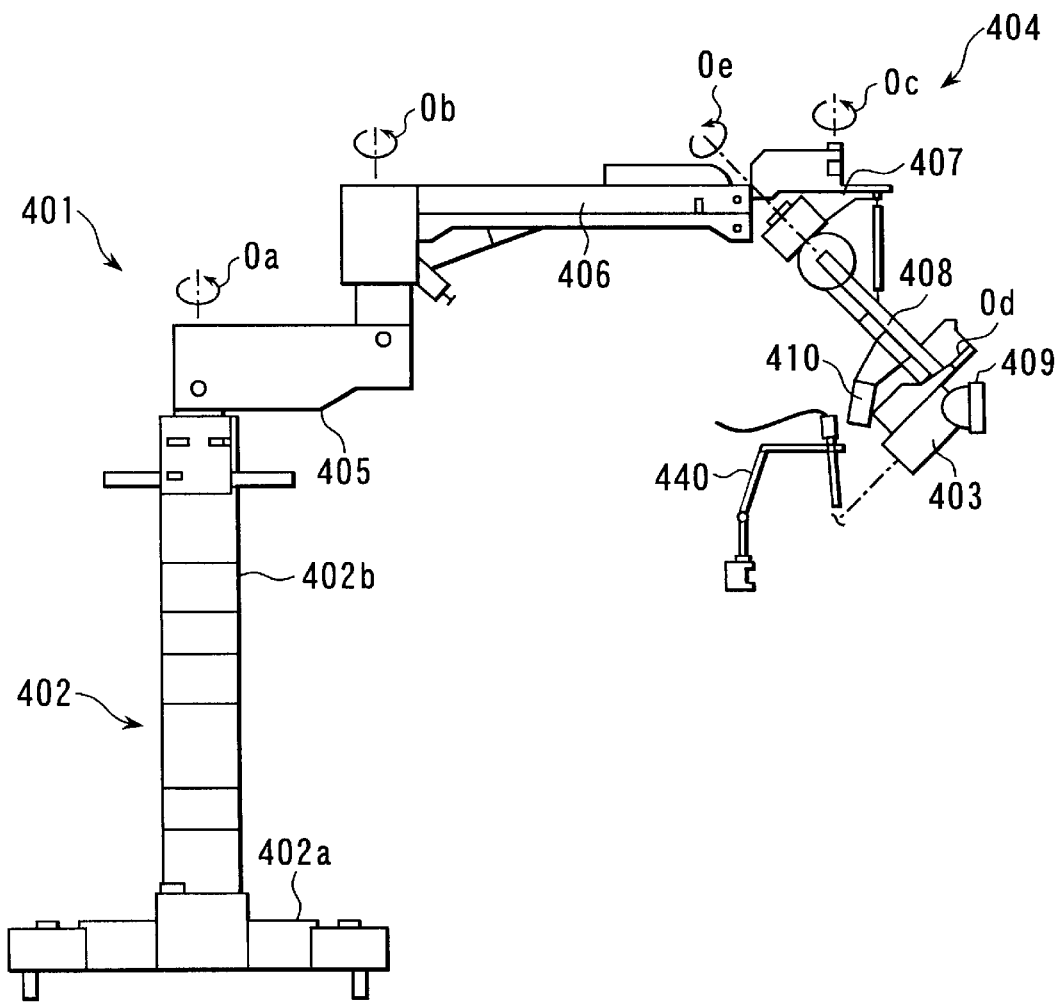
FIG. 43 is a view schematically showing an outline of an operating microscope and an endoscopic apparatus according to a twelfth embodiment.

FIG. 43 shows an outline of an operating microscope apparatus 401 and an endoscopic apparatus according to the present embodiment. The microscopic apparatus 401 of the present embodiment is supported on a stand 402. The stand 402 is provided with a base 402a movable on a floor surface and a support post 402b set up on the base 402a. A moving arm mechanism 404 for movably supporting a microscope body 403 of the microscopic apparatus 401 is provided on the top portion of the support post 402b. The mechanism 404 is formed of a plurality of moving arms including first, second, and third arms 405, 406 and 407 and a swing arm 408.

One end of the first arm 405 is mounted on the upper end portion of the support post 402b for rocking motion around an axis Oa. The first arm 405 has an illumination light source (not shown) therein. One end of the second arm 406 is mounted on the other end of the first arm 405 for rocking motion around an axis Ob.

The second arm 406 is a pantograph arm that is formed of a link mechanism and a balancing spring member, whereby the microscope body 403 can be moved in the vertical direction. The third arm 407 is mounted on the other end of the second arm 406 for rocking motion around an axis Oc.

The proximal end portion of the swing arm 408 is coupled to the third arm 407. The microscope body 403, a binocular tube 409 for stereoscopic observation, and a handle 410 are provided on the distal end portion of the arm 408. The swing arm 408 is supported for longitudinal swinging motion such that it causes the microscope body 403 to rock in the longitudinal direction around an axis Od, which extends at right angles to the drawing plane of FIG. 43, with respect to the direction of the operator's observation, and for transverse swinging motion such that it causes the microscope body 403 to rock in the transverse direction of the operator around an Oe.

Further, electromagnetic brakes (not shown) are provided individually on rocking portions corresponding to the axes Oa to Oe of the moving arm mechanism 404, whereby the position of the microscope body 403 can be freely spatially adjusted and fixed. These brakes are designed so that their locking or free state can be freely selected by operating a switch (not shown) on the handle 410. Preferably, a light source unit (not shown) for the moving arm mechanism 404 should be incorporated in the support post 402b of the stand 402, for example.

The binocular tube 409 of the microscope body 403 is formed having left- and right-hand observational optical paths for stereoscopic observation. Each of the observational optical paths of the lens tube 409 is provided with an objective lens (not shown) and a variable-scale optical system (not shown). Numeral 440 denotes an endoscopic system for observing dead angles of the operating microscope.

Figure 44:
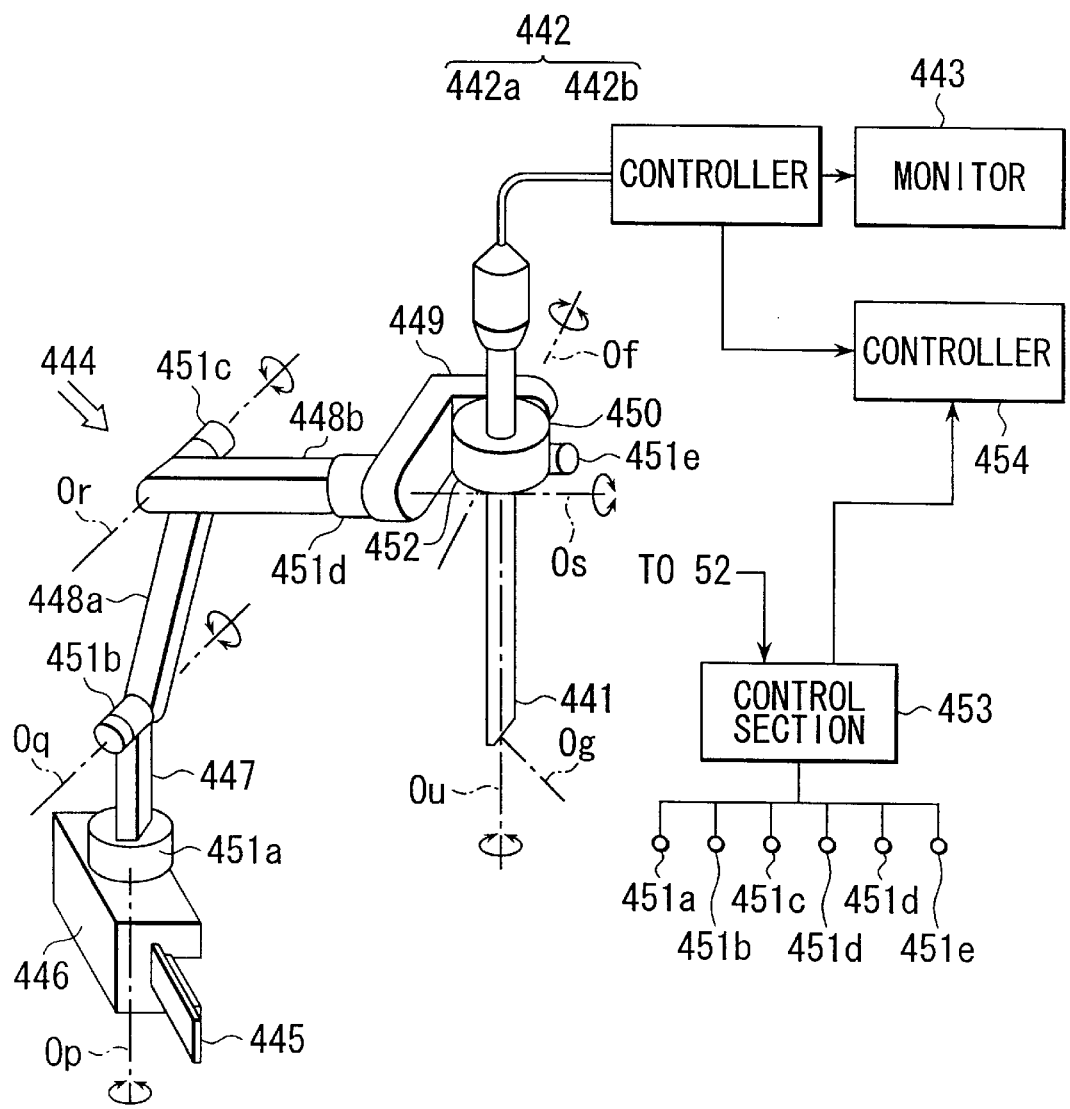
FIG. 44 is a schematic view showing an endoscopic system along with a scope holder for supporting an endoscope shown in FIG. 43.

As shown in FIG. 44, the endoscopic system 440 comp a rigid scope 441 having an observation port axis Og at a given angle to the direction of insertion, a TV camera 442 including a TV camera head 442a for picking up an observational image of the scope 441 and a TV controller 442b, and a monitor 443 connected to the controller 442b and displaying the observational image of the scope 441. The rigid scope 441 is fixed to a bedside stay 445 by means of a scope holder 444.

The scope holder 444 is provided with a fixing portion 446 fixed to the bedside stay 445, vertical arm 447, moving arms 448a and 448b, slanting arm 449, and holding portion 450, which are connected to one another in the order named. The arms 447, 448a, 448b and 449 and the holding portion 450 are rotatable around axes Op, Oq, Or, Os and To, respectively. Electromagnetic brakes 451a to 451e are provided individually at portions corresponding to these axes of rotation, whereby the position of the rigid scope 441 can be freely three-dimensionally adjusted and fixed.

These electromagnetic brakes are designed so that their locking or free state can be selected by operating a switch 452 on the holding portion 450. The switch 450 and the brakes 451a to 451e are connected to a holder control section 453. The control section 453 is provided with a driver circuit (not shown), which outputs driving signals for disengagement to the brakes 451a to 451e while an operating signal from the switch 452 is being inputted, and a circuit that delivers the input signal from the switch 452 to an in-field display controller 454 (mentioned later).

Figure 45:
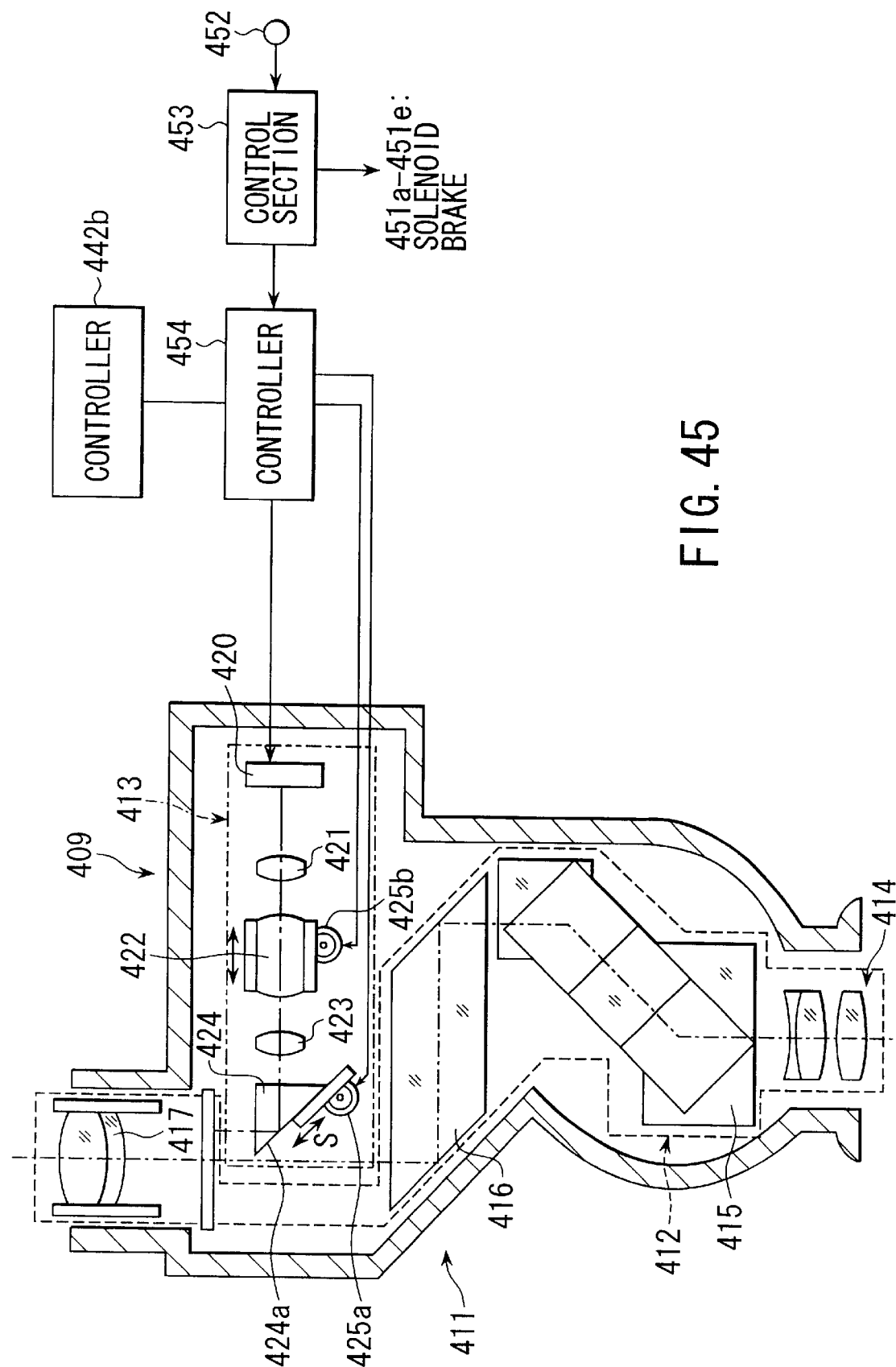
FIG. 45 is a view showing an outline of a binocular tube of the operating microscope of FIG. 43.

FIG. 45 shows an outline of the binocular tube 409 according to the present embodiment. The lens tube 409 is provided with a right-eye observational optical system 411 shown in FIG. 45 and a left-eye observational optical system (not shown). FIG. 45 shows a part of the right-eye optical system 411, viewed from the lateral of the lens tube 409. Since the left-eye observational optical system is constructed in the same manner as the optical system 411 shown in FIG. 45, the following is a description of the optical system 411 only.

The right-eye optical system 411 according to the present embodiment comprises a binocular tube optical system (first observational optical system) 412 for observing the observational image of the operating microscope and an image projection optical system (second observational optical system) 413 for observing optional image information that is different from the observational image. The binocular tube optical system 412 is provided with an imaging optical system 414, image rotator 415, parallelogrammatic prism 416, and eyepiece optical system 417. The observational image of the operating microscope, incident upon the binocular tube optical system 412, is guided from the imaging optical system 414 to the eyepiece optical system 417 via the image rotator 415 and the prism 416 in succession.

Further, the image projection optical system 413 is provided with an LCD display 420 as an in-field display function, collimating optical system 421, variable-scale optical system 422 having a variable projection magnification, imaging optical system 423, and movable prism 424. The prism 424, which is oriented in the direction of arrow S within the plane of a reflective surface 424a, is movable with respect to the image projection optical system 413 by means of a motor 425a. On the other hand, the variable-scale optical system 422 is connected so that its magnification can be changed by driving a motor 425b.

The movable prism 424 and the variable-scale optical system 422 are driven in a relation such that the image on the LCD display 420 is enlarged in proportion to the depth of insertion of the prism 424 in the binocular tube optical system 412 as it is projected by means of the optical system 422.

The image information displayed on the LCD display 420 is guided to the eyepiece optical system 417 successively through the collimating optical system 421, variable-scale optical system 422, imaging optical system 423, and movable prism 424. The eyepiece optical system 417 ensures simultaneous observation of the observational image of the operating microscope transmitted through the binocular tube optical system 412 and the optional image information transmitted through the image projection optical system 413.

Numeral 454 denotes the in-field display controller (display format changing means), which is connected to the holder control section 453 to which the switch 452 of the scope holder 444 is connected, LCD display 420, TV controller 442b, and motors 425a and 425b. The controller 454 is composed of driver circuits for the motor 425a for moving the prism 424 and the motor 425b for driving the variable-scale optical system 422, control circuits for controlling the drive of the driver circuits, and a display control circuit that is supplied with a video signal from the TV controller 442b of the TV camera 442 and displays an image on the LCD display 420.

The observational image of the operating microscope apparatus 401 ensures stereoscopic observation of an affected region through the microscope body 403 by means of the binocular tube optical system 412 of the binocular tube 409. As this is done, the movable prism 424 of the image projection optical system 413 is on the optical path of the binocular tube optical system 412, as shown in FIG. 45. The image of the affected region observed through the rigid scope 441 is picked up by means of the TV camera head 442a shown in FIG. 44. This image is displayed on the monitor 443 and the LCD display 420 by means of the TV controller 442b and the in-field display controller 454 shown in FIG. 45, respectively. The display image is observed through the image projection optical system 413 and the eyepiece optical system 417.

Figure 46:
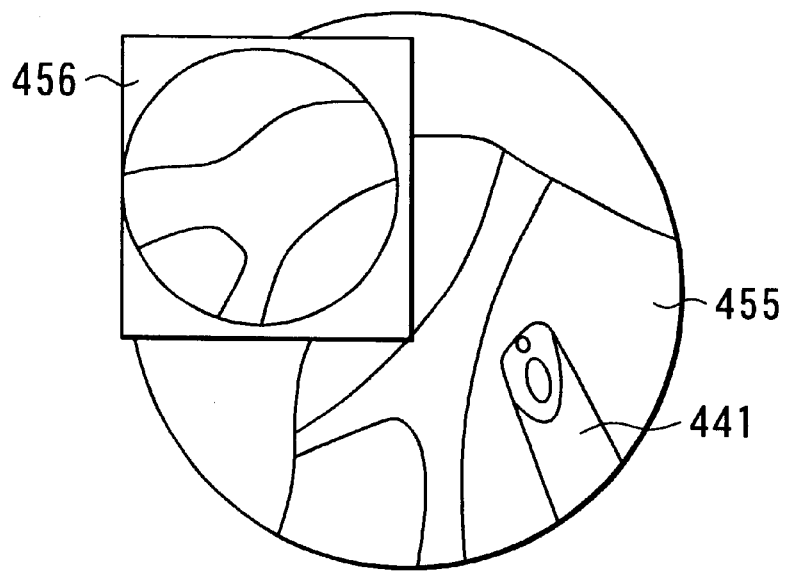
FIG. 46 is a view showing an observational state of the operating microscope for the case where an endoscopic image is mainly observed as a surgical operation is carried out.
Figure 47:
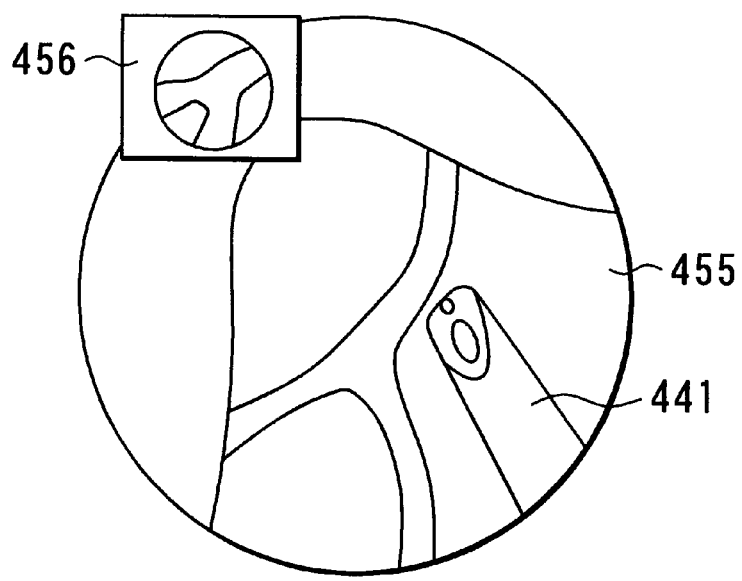
FIG. 47 is a view similar to FIG. 46, showing an observational state of the operating microscope for the case where the observational position of the endoscope is moved.

FIG. 46 shows a state of observation for the case where the image of the rigid scope is mainly observed as the surgical operation is carried out. In FIG. 46, numerals 455 and 456 denote a microscopic image and an image observed through the rigid scope 441, respectively. The rigid scope 441 itself is displayed in the microscopic image 455.

On the other hand, the operator can change the observational position of the rigid scope 441 by depressing the switch 452 of the scope holder 444 to disengage the electromagnetic brakes 451a to 451f. By doing this, the rigid scope 441 can be freely moved in a three-dimensional manner. As this is done, the holder control section 453 disengages the electromagnetic brakes 451a to 451b to cancel the locked state, and delivers an ON-signal of the switch 452 to the in-field display controller 454.

On receiving this input signal, the in-field display controller 454 drives the motors 425a and 425b to a previously stored specified extent, and the depth of insertion of the movable prism 424 in the binocular tube optical system is reduced. At the same time, the magnification of the variable-scale optical system 422 is changed into (or lowered to) a value that is settled properly for the movement of the movable prism 424. Thereupon, the image observed through the eyepiece optical system 417 looks like the one shown in FIG. 47. Thus, the image 456 of the rigid scope, compared to the microscopic image 455, moves to an end of the field of vision, and is displayed in a contracted form.

In this manner, the image 456 of the rigid scope 441, compared to the observational image 455 of the operating microscope, is observed in a wide range in the case where the observational position of the scope 441 is fixed, and in a narrow range if the observational position of the scope 441 is changed (or if the scope 441 is moved). When no normal rigid scope observation is carried out, a footswitch (not shown) of the microscope can be operated entirely to remove the movable prism 424 from the optical path of the binocular tube optical system 412 with ease. Thus, observation can be effected in the same manner as the observation by means of the conventional operating microscope.

The rigid scope image 456 is displayed wide on the observational image 455 of the operating microscope when it is used for a required treatment or observation, so that the treatment operation is easy. Since the display of the rigid scope image 456 is small while the rigid scope 441 is being moved, on the other hand, the state of insertion of the rigid scope 441 in the microscopic image 455 can be observed satisfactorily.

According to the present embodiment, the operating state of the rigid scope 441 is detected by detecting the disengagement of the scope holder 444 for holding the scope 441, so that the surgical operation can be smoothly carried out without requiring use of any special device for detection and its operation.

Further, the movement of the rigid scope 441 can be detected more easily than by using an optical position detector according to a thirteenth embodiment described below.

Thirteenth Embodiment

FIGS. 48 to 50B show a thirteenth embodiment.

Figure 48:
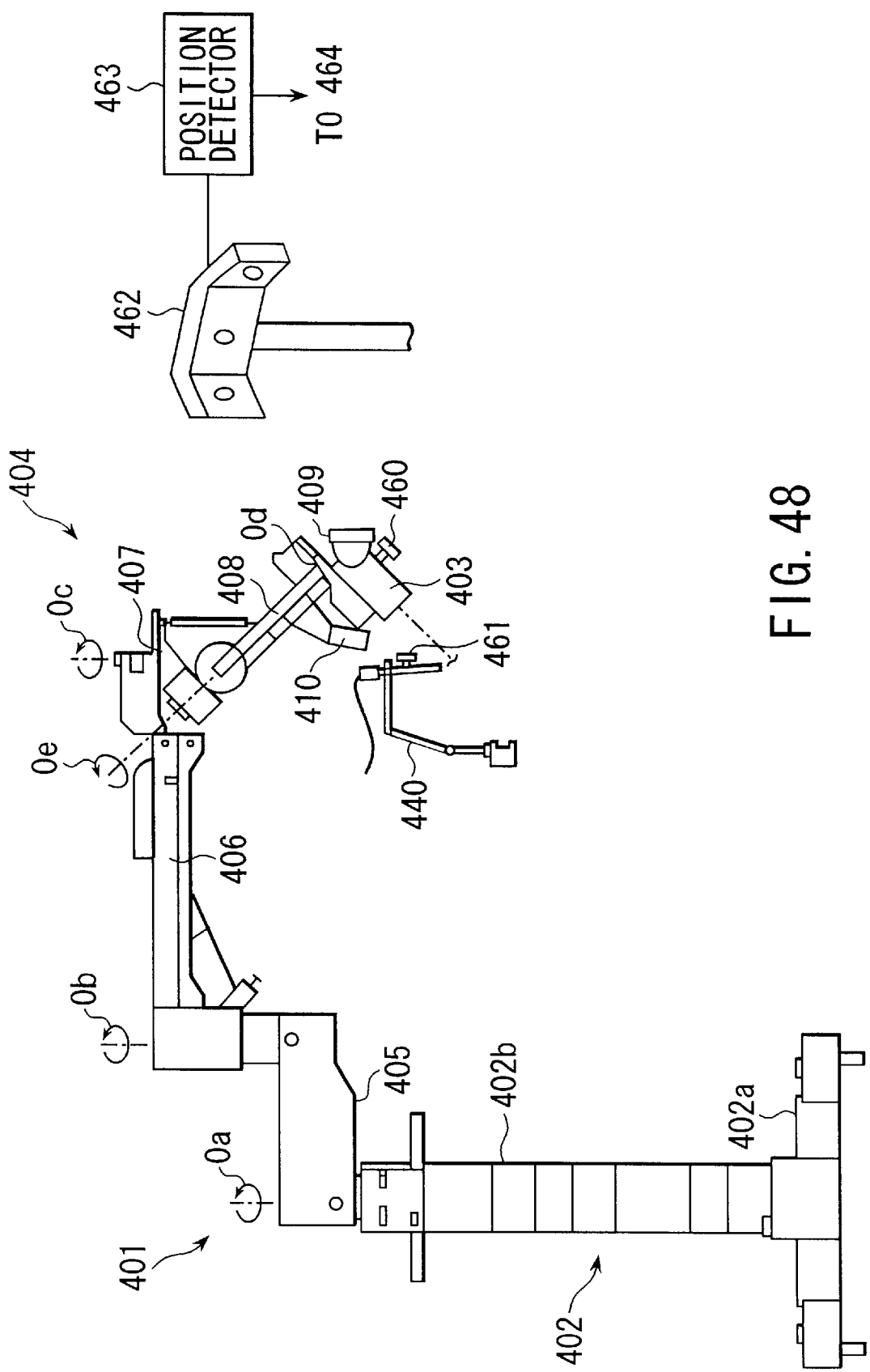
FIG. 48 is a view similar to FIG. 43, schematically showing an outline of an operating microscope and an endoscopic system according to a thirteenth embodiment.

As is schematically shown in FIG. 48, an operating microscope apparatus 401 and an endoscopic system 440 according to the present embodiment are constructed in the same manner as the ones according to the twelfth embodiment, so that a detailed description of those elements is omitted. The following is a description of the optical position detector for the operating microscope apparatus 401 and the endoscopic system 440. This optical position detector may be a conventional one.

As shown in FIG. 48, emissive indexes 460 and 461 are attached to the operating microscope apparatus 401 and the endoscopic system 440, respectively. The indexes 460 and 461 can be shot by means of an illuminant image-pickup device 462 that is provided with image-pickup means. The device 462 is connected with a position detecting section 463 for computing the position and angle of an illuminant in response to a signal from the device 462. The position detecting section 463 is composed of a position data computing section for a microscope body 403, a position data computing section for a rigid scope 441, and a position calculating section for calculating the position of the rigid scope 441 relative to the position of the microscope body 403. The detecting section 463 delivers information on the observational direction of the rigid scope with respect to the microscope body 403 to an in-field display controller 464, which will be mentioned later.

Figure 49:
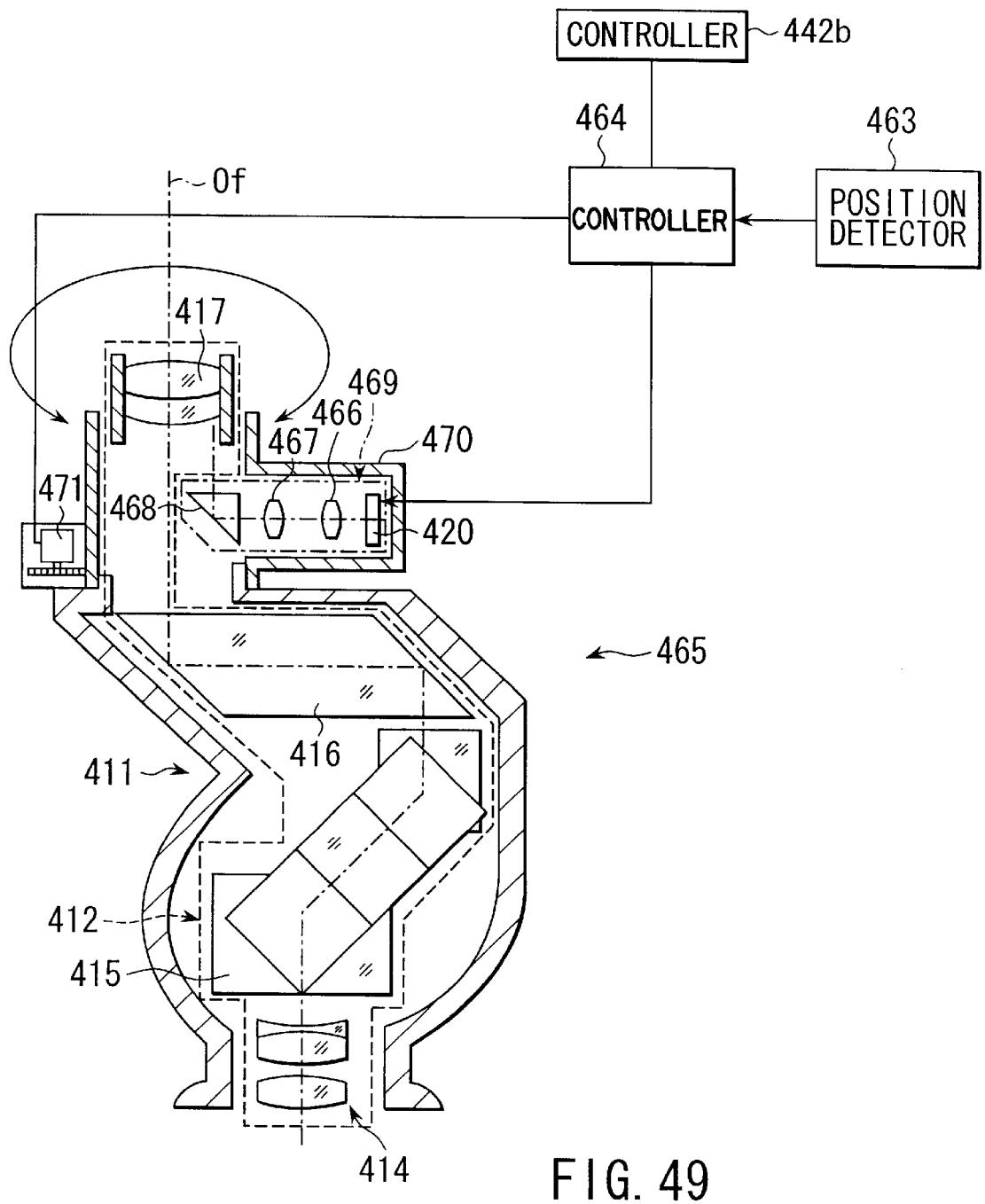
FIG. 49 is a view showing an outline of a binocular tube of the operating microscope of FIG. 48.

FIG. 49 shows an outline of a binocular tube 465 according to the present embodiment.

A binocular tube optical system 412 of the binocular tube 465 is constructed in the same manner as the one according to the twelfth embodiment. Therefore, a description of the system 412 is omitted, and the following is a description of an arrangement of an image projection optical system 469, a unique element.

The image projection optical system 469 comprises an LCD display 420 for use as an in-field display function, collimating optical system 466, imaging optical system 467, and prism 468. Image information displayed on the LCD display 420 is guided to an eyepiece optical system 417 successively through the collimating optical system 466, imaging optical system 467, and prism 468.

The image projection optical system 469, which is incorporated in a chassis 470, is connected so that it can be rocked integrally with the chassis 470 around an optical axis Of of the eyepiece optical system 417 of the binocular tube 465 by means of a motor 471. The eyepiece optical system 417 ensures simultaneous observation of the observational image of the operating microscope transmitted through the binocular tube optical system 412 and optional image information transmitted through the image projection optical system 469.

The in-field display controller 464 is connected to the position detecting section 463 of the aforesaid optical position detector, a TV controller 442b, the LCD display 420, and the chassis rotating motor 471. The controller 464 is composed of a driver circuit for the chassis rotating motor 471, control circuit for controlling the drive of the driver circuit, display control circuit for the LCD display 420, control circuit for controlling the rotation of the motor 471 in response to a position signal from the position detecting section 463, and a display control circuit that is supplied with a video signal from the TV camera 442 and displays an image on the LCD display 420.

The observational image of the operating microscope apparatus according to the thirteenth embodiment ensures stereoscopic observation of an affected region through the microscope body 403 by means of the binocular tube optical system 412 of the binocular tube 465. As this is done, the movable prism 468 of the image projection optical system 469 is on the optical path of the binocular tube optical system 412, as shown in FIG. 49. The image of the affected region observed through the rigid scope 441 is picked up by means of a TV camera head 442a. This image is displayed on a monitor 443 and the LCD display 420 by means of the TV controller 442b and the in-field display controller 464, respectively. The display image on the display 420 is observed through the image projection optical system 469 and the eyepiece optical system 417.

Figure 50A:
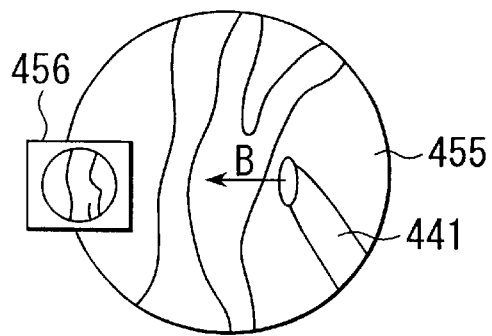
FIGS. 50A and 50B are views individually showing states of observation through an eyepiece optical system of the binocular tube shown in FIG. 49.
Figure 50B:
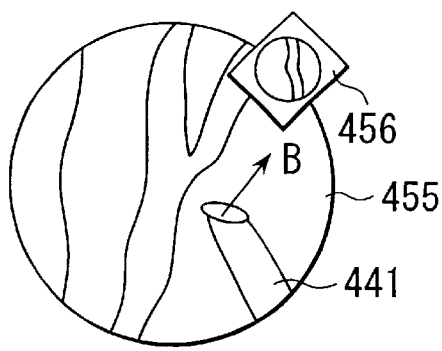

During a surgical operation, the respective positions of the microscope body 403 and the rigid scope 441 are always detected by means of a conventional optical position detector. The position detecting section 463 obtains the direction (angle) of observation of the rigid scope 441 with respect to the observation direction of the microscope body 403, and delivers angle information to the in-field display controller 464. In response to this angle information, the controller 464 rotates the motor 471 as required, thereby causing the image projection optical system 469 always to rotate integrally with the chassis in the same direction as the observation direction of the rigid scope. FIGS. 50A and 50B show states that are observed by means of the eyepiece optical system 417. In this case, an image of the rigid scope 441 is displayed in the same direction as the observational direction (indicated by arrow B) of the scope 441.

According to the operating microscope 401 of the present embodiment, the image 456 that is obtained through the rigid scope 441 and displayed in the field of observation is displayed in the same direction as the observational direction of the rigid scope, so that the operator can intuitively recognize the observational direction of the rigid scope 441. Thus, the operator can be intent on the surgical operation without suffering troublesomeness, and therefore, the operation time can be shortened.

Since the optical position detecting means is used in the present embodiment, moreover, the system is readily compatible with a conventional navigation system that displays the respective observational positions of the surgical operation and the rigid scope 441 on a diagnostic image.

According to the present embodiment, furthermore, the optical position detecting means is used to detect the observational direction of the rigid scope 441 with respect to the microscope body 403. Alternatively, however, the observational direction of the rigid scope 441 can be easily detected by means of an encoder or the like that is attached to a joint portion of the scope holder of the twelfth embodiment and serves as rotational angle detecting means. In this case, a simple system can be enjoyed.

Fourteenth Embodiment

A fourteenth embodiment will be described with reference to FIG. 51. According to the present embodiment, the operating microscope apparatus of the twelfth embodiment is modified so that the binocular tube is designed differently and its visibility is automatically adjusted to the operator's eyes.

Figure 51:
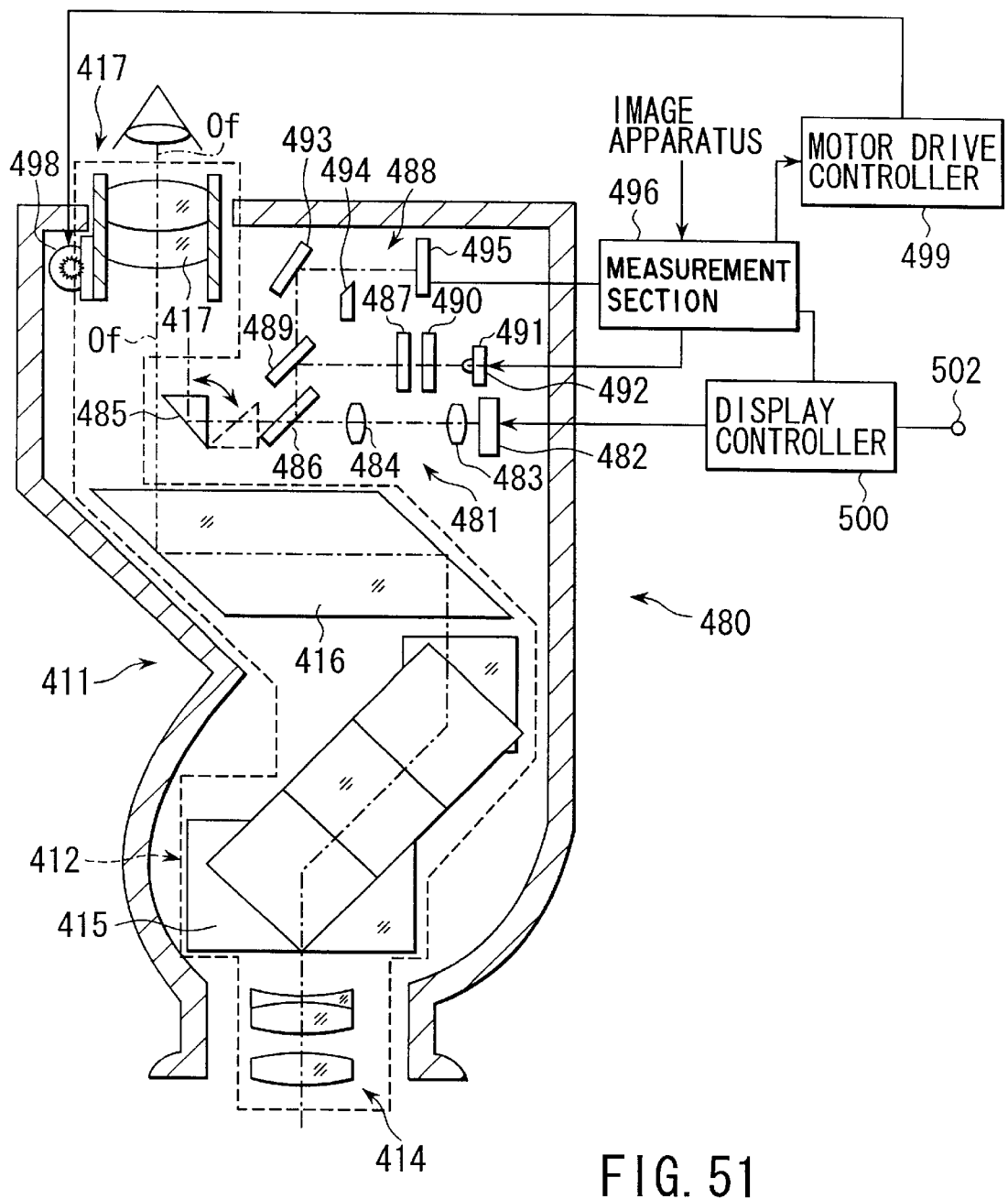
FIG. 51 is a view illustrating a binocular tube optical system of an operating microscope according to a fourteenth embodiment.

FIG. 51 shows an outline of a binocular tube 480 according to the present embodiment. The binocular tube 480 is provided with a binocular tube optical system (first observational optical system) 412, which is similar to the one according to the first embodiment, an image projection optical system 481 for observing optional image information that is different from an observational image, a measurement optical system 487 for refractive index measurement, and a light receiving optical system 488. The optical systems 481, 487 and 488 constitute a second observational means. A detailed description of the binocular tube optical system 412, which is constructed in the same manner as the one according to the twelfth embodiment, is omitted.

The image projection optical system 481 comprises an LCD display 482 for use as in-field display means, collimating optical system 483, imaging optical system 484, and movable prism 485. A dichroic mirror 486 is located on an optical path between the prism 485 and the imaging optical system 484. The movable prism 485 is provided on the optical path in a manner such that it can be removed by means of a motor (not shown).

The measurement optical system 487 comprises the movable prism 485, the dichroic mirror 486, a half-mirror 489, a slit plate 490 in a position conjugate to the eyeground of a subject eye having a reference refractive force, a diffuser panel 491, and a light emitting diode for emitting infrared light. Thus, the optical system 487 shares some components with the image projection optical system 481.

The light receiving optical system 488 comprises the movable prism 485, the dichroic mirror 486, the half-mirror 489, a shielding member 494 in a position conjugate to the slit plate 490, and a light receiving element 495 in a position conjugate to the pupil. Thus, the optical system 488 shares some components with the measurement optical system 487. Numeral 496 denotes a measurement section for computing the refractive force of the subject eye according to the light quantity distribution of the light receiving element 495. The measurement section 496 is connected to a visibility correction motor drive control section 499 and an in-field display controller 500 (mentioned later), as well as to the light emitting diode 492.

The eyepiece optical system 417 ensures simultaneous observation of the observational image of the operating microscope transmitted through the binocular tube optical system 412 and optional image information transmitted through the image projection optical system 481. Further, the optical system 417 is designed so that it can make visibility adjustment by moving in the direction of its optical axis Of. A motor 498 can be used for the movement in the direction of the optical axis Of. Numeral 499 denotes the visibility correction motor drive control section that is connected to the motor 498 and the in-field display controller (mentioned later). The control section 499 is provided with a driver circuit for the motor 498 and a control circuit for controlling the drive of the motor. The motor 498 and the visibility correction motor drive control section 499 constitute visibility correction motor drive means.

The in-field display controller 500 is connected to the LCD display 482, the measurement section 496, a switch 502 that is connected to the operating microscope apparatus, a motor (not shown) for the movable prism 485, and an external image apparatus. The controller 500 comprises a motor drive control circuit for the prism 485, a display control circuit, and a driving signal output circuit for driving the measurement section. The display control circuit displays an image on the LCD display 482 and displays a stored fixed-view display pattern for measurement in response to input from the switch 502.

The observational image of the operating microscope according to the present embodiment and the image displayed on the LCD display 482 are observed through the eyepiece optical system 417 in the same processes of operation of the twelfth and thirteenth embodiments. The images can be observed in the same manner as in the conventional operating microscope if the movable prism 485 is removed from the optical path.

The following is a description of visibility adjustment.

If the operator turns on the switch 502 of the operating microscope apparatus, the in-field display controller 500 displays the previously stored fixed-view display pattern on the LCD display 482. This image is observed through the image projection optical system 481 and the eyepiece optical system 417 by the operator. The operator's eyes are fixed as they gaze steadily at the fixed-view display pattern. At the same time, the controller 500 causes the measurement section 496 to start measuring the refractive force.

The following is a description of operation for the refractive force measurement.

In response to a signal from the measurement section 496, infrared light is emitted from the light emitting diode 492. This infrared light is projected on the operator's eyeground via a slit (not shown) of the slit plate 490, half-mirror 489, dichroic mirror 486, movable prism 485, and eyepiece optical system 417. Thus, a slit image of the slit plate 490 is projected on the eyeground.

The projected infrared light is reflected by the eyeground and delivered to the light receiving element 495 via the eyepiece optical system 417, the movable prism 485, the dichroic mirror 486, the half-mirror 489, a mirror 493, and the shielding member 494. Based on information on the light quantity distribution from the light receiving element, the measurement section computes the refractive force of the operator's eyes. Based on the result of this computation, the visibility correction motor drive control section causes the motor 498 to rotate, thereby moving the eyepiece optical system 417 for a required distance in the direction of the optical axis Of. Thereupon, the operator's visibility adjustment is completed.

The operating microscope of the present embodiment has a very simple construction, since the image projection optical system, which can display another image in the field, and the optical systems (measurement optical system and light receiving optical system) for measuring the refractive force share some of their components. Since the optical path separate from the one for the observational image of the operating microscope is used, moreover, the observational performance of the microscope cannot be ruined.

Since the fixed-view display that causes the operator to gaze steadily at the image is made on the LCD display screen, furthermore, accurate measurement can be accomplished without being influenced by the focusing capability of the eyes.

Further, the observational performance of the operating microscope cannot be lowered if the movable prism is removed from the optical path.

Fifteenth Embodiment

Figure 52:
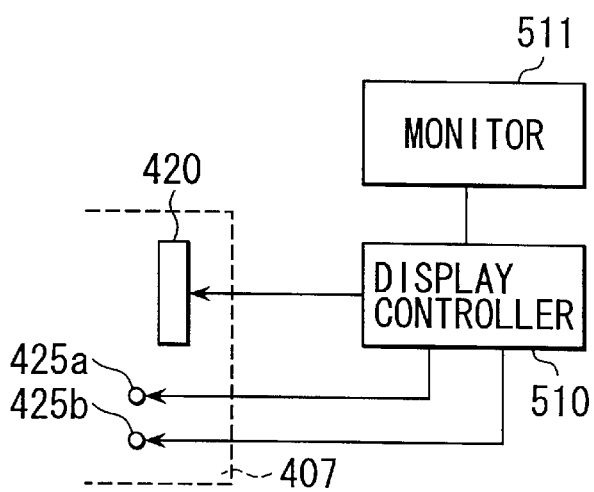
FIG. 52 is a view showing an outline of a in-field display controller of an operating microscope according to a fifteenth embodiment.
Figures 53A, 53B:
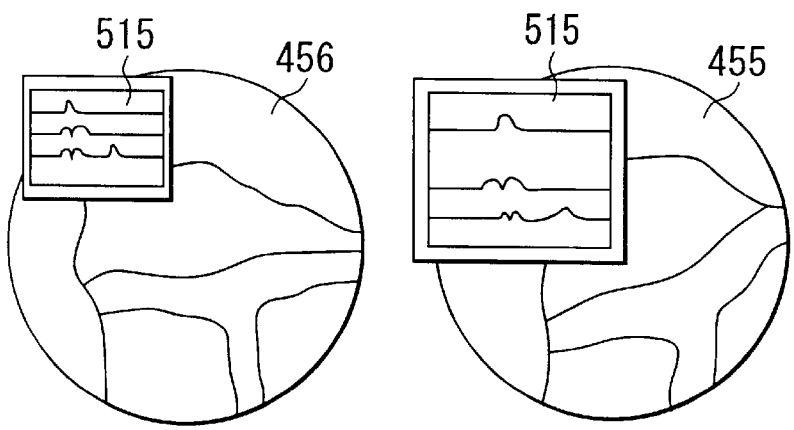
FIGS. 53A and 53B are views individually showing display states in the field of an operating microscope according to a sixteenth embodiment.

According to a fifteenth embodiment shown in FIGS. 52 to 53B, an image of a nerve monitor device that displays the nerve state of a patient in the field of an operating microscope during a surgical operation. The present embodiment differs from the twelfth embodiment only in the construction of the in-field display controller.

As shown in FIG. 52, an in-field display controller 510 of the present embodiment is connected to a binocular tube 409 that is similar to the one according to the twelfth embodiment. A nerve monitor device 511 displays a wavy image indicative of the nerve state on a monitor (not shown), and delivers a video signal for the wavy image to the controller 510. Further, the monitor device 511 is provided with abnormal signal output means through which the operator can be informed of change of the nerve state. The output means is connected to the controller 510.

The in-field display controller 510 is composed of driver circuits for a motor 425a for moving the movable prism 424 of the twelfth embodiment and a motor 425b for driving the variable-scale optical system 422, control circuits that are supplied with signals from the abnormal signal output means from the nerve monitor device 511 and controls the drive of the motors 425a and 425b, and a display control circuit that is supplied with a video signal from the monitor device 511 and displays an image on an LCD display 420.

In the operating microscope according to the present embodiment, an image 515 of the nerve monitor device 511 is normally displayed in the field of the operating microscope in the manner shown in FIG. 53A during the surgical operation. If the nerve state of the patient is changed during the operation, a signal is outputted from the abnormal signal output means of the monitor device 511, whereupon the in-field display controller 510 drives the motors 425a and 425b in the same manner as in the twelfth embodiment.

In consequence, the nerve monitor image 515 is displayed wide, as shown in FIG. 53B.

Thus, the operator can easily recognize the nerve state of the patient.

According to the operating microscope of the present embodiment, therefore, the size of the display information of the nerve monitor device varies despite the operator's concentration on the surgical operation, so that the operator never overlooks the change of the patient's nerve state.

The following is a description of rigid scope systems according to three alternative embodiments that are applicable to the surgical system described above. These embodiments are solutions to the rigid scopes described in Jpn. UM Appln. KOKAI Publications Nos. 5-78201 and 56-176703, U.S. Pat. No. 5,168,863, and Jpn. Pat. Appln. KOKAI Publication No. 11-155798. More specifically, these alternative embodiments are intended to improve a rigid scope that is adapted to be inserted into the body cavity under surgical microscopic observation and ensure observation in the direction at a given angle to the direction of insertion, to prevent the rigid scope and a TV camera and a light guide connected thereto from hindering the microscopic observation or surgical operation, and to enable the operator to observe desired positions with ease.

Sixteenth Embodiment

A system according to a sixteenth embodiment will now be described with reference to FIGS. 54 and 55.

Figure 54:
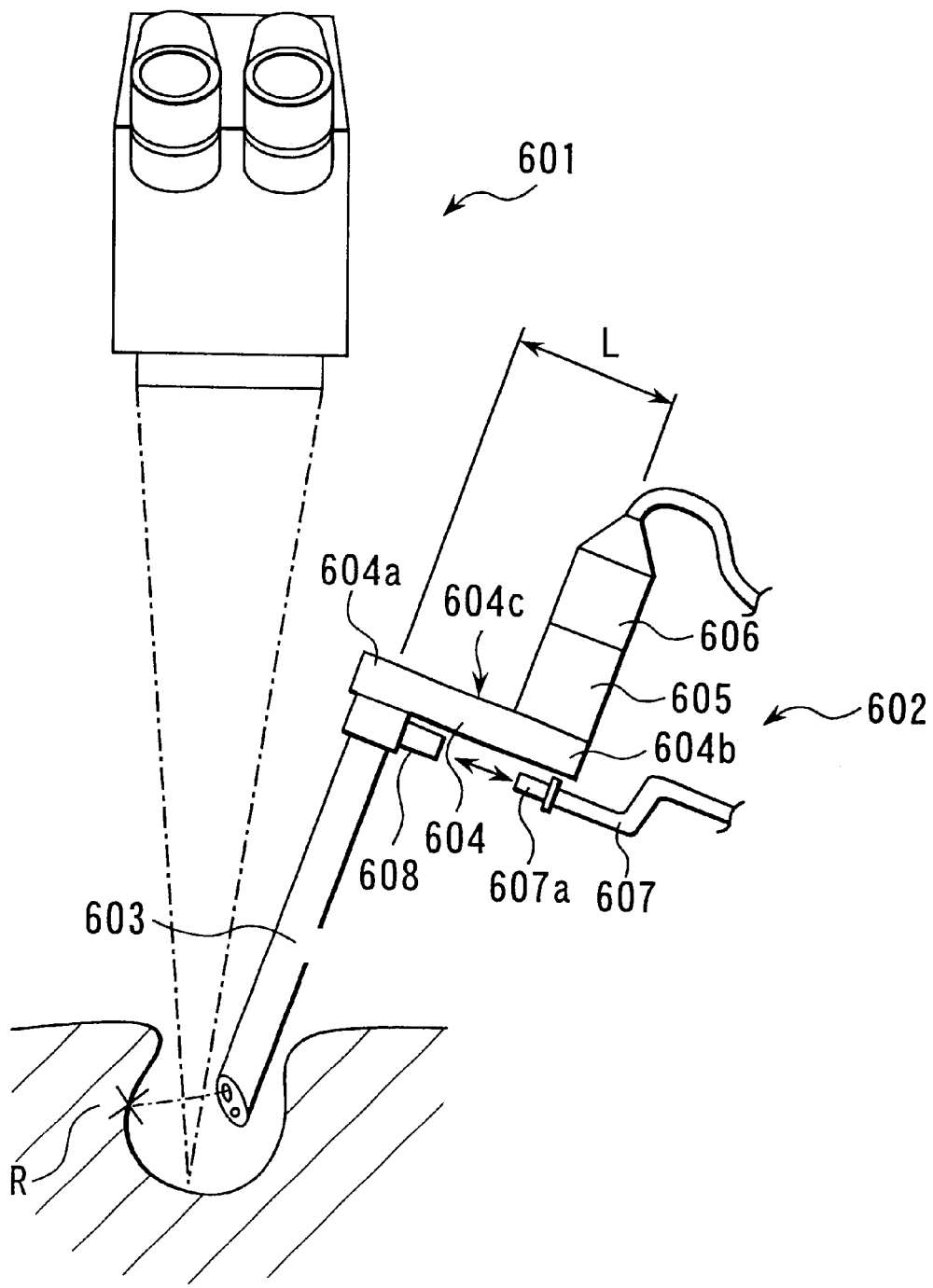
FIG. 54 is a general view of a surgical system using a rigid scope in combination with an operating microscope according to a seventeenth embodiment.

FIG. 54 shows a general configuration of a rigid scope system. In FIG. 54, numeral 601 denotes a body of an operating microscope. The microscope body 601 is held over an affected region by means of an arm stand (not shown) in a manner such that its observational direction can be changed freely. Numeral 602 denotes a rigid scope, which comprises an insert member 603 adapted to be inserted into the affected region (body cavity) and having an objective lens and an internal light guide (mentioned later) fixed therein, a coupling portion 604 composed of first and second bent portions 604a and 604b, and a grip portion 605 having an eyepiece. Symbol R designates a point of observation of the rigid scope 602.

An upper surface 604c of the coupling portion 604 is coated with light absorbing paint such as matte black. The grip portion 605 has therein a camera connecting portion, which is connectable with a TV camera 606 that is connected optically to an imaging lens (mentioned later).

Numeral 607 denotes an external light guide, one end of which is connected to a light source unit (not shown). A connector 607a on the other end of the light guide 607 can be attached to and detached from a light guide mouthpiece 608 that projects substantially parallel to the bending direction of the first bent portion 604a, at the upper end of the insert portion 603 of the rigid scope 602.

The construction of the rigid scope 602 will now be described in detail with reference to FIG. 55. An objective lens 609 is provided in the distal end portion of the insert portion 603. The lens 609 is fixed obliquely to the distal end of the insert portion 603 so that it is inclined at a given angle a to the longitudinal direction of the insert portion 603. A prism 610 and a relay optical system 611 are also arranged in the insert portion 603. The respective optical axes of the objective lens 609 and the optical system 611 are kept at the aforesaid angle a with the prism 610 between them.

A prism 612 is located in the first bent portion 604a of the coupling portion 604, whereby an observational optical axis O1 of the relay optical system 611 can be bent at about 90°. A relay optical system 613 is provided in an intermediate portion of the coupling portion 604, and a prism 614 is disposed in the second bent portion 604b of the coupling portion 604. The prism 614 serves to bend the observational optical axis, bent by means of the prism 612, so as to extend substantially in the longitudinal direction of the insert portion 603. Further, the grip portion 605 has therein a relay optical system 615 located on a luminous flux that is guided by means of the prism 614. An imaging lens 616 is disposed in the rear end portion of the grip portion 605. The lens 616 serves to focus an observational luminous flux on an image-pickup device 617 of the TV camera 606.

A cable 618 that is connected electrically to the image-pickup device 617 of the TV camera 606 is connected to a drive unit (not shown), and a TV monitor (not shown) is connected electrically to the drive unit. The TV camera 606 is detachably connected to the grip portion 605 by means of a mounting screw portion 619.

In the vicinity of the objective lens 609, an illuminating lens 620 is disposed in the distal end of the insert portion 603. The distal end of an internal light guide 621 is fixed to the inside of the lens 620 in a manner such that it is situated on the optical axis of the lens 620 and that the respective centers of the guide 621 and the lens 620 are substantially aligned with each other. The illuminating lens 620 and the internal light guide 621 constitute an illumination optical system according to the present embodiment. In a space portion 622 that is defined at the junction between the insert portion 603 and the coupling portion 604, the light guide 621 is fixed to the light guide mouthpiece 608 with some slack. The light guide mouthpiece 608 is formed having a mounting screw portion 623 that serves to connect the external light guide 607 optically to the internal light guide 621.

The coupling portion 604 is provided with a bearing portion 624, which engages a flange 625 on the rear end of the insert portion 603 so as to hold the insert portion 603 for rotation around its longitudinal central axis. The bearing portion 624 and the flange 625 constitute a rotation mechanism portion 626.

With the arrangement described above, the operator operates the arm stand (not shown) that supports the operating microscope body 601, thereby adjusting the microscope body 601 to a desired position and angle. Further, illumination light is applied to the affected region through the microscope body 601, and the affected region is subjected to enlarged-scale observation.

Then, the observational dead-angle region R of the operating microscope in the affected region is observed by means of the rigid scope 602. First, the connector 607a of the external light guide 607 is connected to the light guide mouthpiece 608 of the rigid scope 602, and the other end of the light guide 607 is connected to the light source unit (not shown). Further, the cable 618 of the TV camera 606 is connected to the drive unit (not shown).

As shown in FIG. 54, the insert portion 603 is inserted into the affected region with the grip portion 605 and the TV camera 606 kept at a distance L from the microscope body 601, and the objective lens 609 is directed to a position near the observational dead-angle region R.

The illumination light emitted from the light source (not shown) guided to the observational dead-angle region R by means of the external light guide 607, internal light guide 621, and illuminating lens 620. The light from the region R is transmitted through the objective lens 609, prism 610, and relay optical system 611, and then bent at about 90° by means of the prism 612. After it is transmitted through the relay optical system 613, moreover, the light is bent in the same direction as the longitudinal direction of the insert portion 603 by means of the prism 614, and focused on the image-pickup device 617 of the TV camera 606 via the relay optical system 615 and the imaging lens 616. A video image of the observational dead-angle region R is displayed on the TV monitor (not shown) by means of the drive unit (not shown) and observed by the operator.

Figure 55:
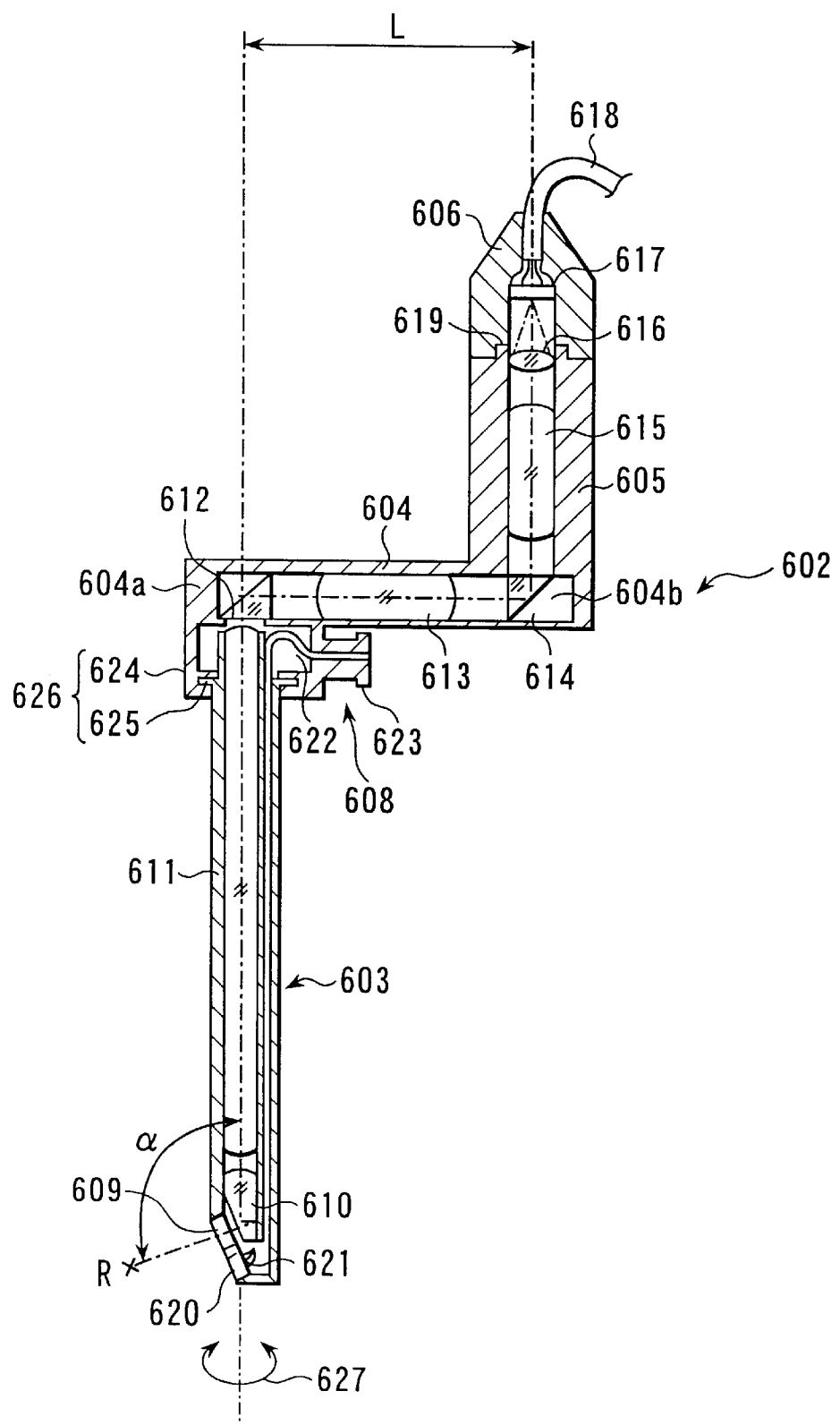
FIG. 55 is a detailed sectional view showing the construction of the rigid scope shown in FIG. 54.

Then, in changing the observational position of the rigid scope 602 from the observational dead-angle region R within a plane perpendicular to the direction of insertion of the insert portion 603, the operator operates the rotation mechanism portion 626 to rotate the insert portion 603 in the direction of an arrow 627 shown in FIG. 55 with respect to the coupling portion 604. As this is done, the rotation of the insert portion 603 is absorbed by the slack of the internal light guide 621 in the space portion 622, so that the light guide 621 can never be pulled. Thus, the observational position of the rigid scope 602 can be changed without changing the respective positions of the coupling portion 604 and the grip portion 605 with respect to the operating microscope body 601.

As the operator's treatment advances, it sometimes may be hindered by the coupling portion 604, grip portion 605, TV camera 606, etc. during the observation of the observational dead-angle region R. In this case, the coupling portion 604 is rotated reversely in the direction of the arrow 627 with respect to the insert portion 603 by means of the rotation mechanism portion 626. Thus, the respective positions of the grip portion 605, coupling portion 604, external light guide 607, and TV camera 606 with respect to the operating microscope body 601 can be changed without changing the observational position of the rigid scope 602.

According to the present embodiment, the grip portion 605 is located at the fixed distance L from the insert portion 603 with the coupling portion 604 between them. If the rigid scope 602 is inserted into the affected region (body cavity) under surgical microscopic observation, therefore, the microscope body 601, grip portion 605, and TV camera 606 can avoid interfering with each other. Since the external light guide 607 that is connected to the light source unit is guided in the same direction as the coupling portion 604, moreover, it can be prevented from unexpectedly intercepting the microscopic field. Thus, the light guide 607 exerts no bad influence upon the microscopic observation.

Since the length of projection of the grip portion 605 and the TV camera 606 within the plane of the affected region is restricted to the minimum, e.g., the distance L, furthermore, the space required by the operator's surgical operation is reasonable, and the possibility of the projecting part hindering the operation can be minimized.

Further, the observational direction of the rigid scope 602 can be changed without changing the respective positions of the grip portion 605 and the TV camera 606. When the observational direction of the rigid scope 602 is changed, therefore, the grip portion 605 and the TV camera 606 can be prevented from interfering with the operator's hands or body, and the external light guide 607 and the TV camera cable 618 can be prevented from intercepting the microscopic field. Thus, the efficiency of the surgical operation cannot be lowered. Since the respective positions of the grip portion 605 and the TV camera 606 can be changed without changing the observational position of the rigid scope 602, moreover, change of a style can be quickly tackled with the progress of the operation, so that the efficiency of the operation is improved further.

Moreover, the upper surface 604c of the coupling portion 604 is coated with light absorbing paint such as matte black. If the coupling portion 604 gets into the surgical microscopic field, therefore, the illumination light of the operating microscope can be prevented from being reflected by the coupling portion 604 and dazzling in the microscopic field.

In connection with the present embodiment, furthermore, the coating method, e.g., matte black coating, has been described as reflection preventing means on the upper surface 604c of the coupling portion 604. However, satin finish, filling, or other means for restraining reflection may be used with the same result.

With the arrangement in which the insert portion and the grip portion are coupled by means of the coupling portion so as to bend like a crank, as in the case of the sixteenth embodiment or the embodiments mentioned later, a plurality of rigid scopes 602 with different squint directions for the insert portion 603 may be prepared, or a joint structure may be provided such that a plurality of rigid scopes or insert portions with different squint directions can be attached and detached for replacement. According to the sixteenth embodiment, the squint direction is opposite to the direction of the coupling portion (and the direction of the mouthpiece for the external light guide 607) against the grip portion. Alternatively, however, the direction of the coupling portion 604 or the mouthpiece for the external light guide 607 may be shifted around the axis of the insert portion. Rigid scopes of the conventional type may be available with various angular relations between the squint direction and the direction of the lateral mouthpiece for the external light guide.

Seventeenth Embodiment

A system according to a seventeenth embodiment will now be described with reference to FIGS. 56 to 58. In the description of the present embodiment to follow, like reference numerals are used to designate the same portions of the sixteenth and seventeenth embodiments, and a description of those portions is omitted.

Figure 56:
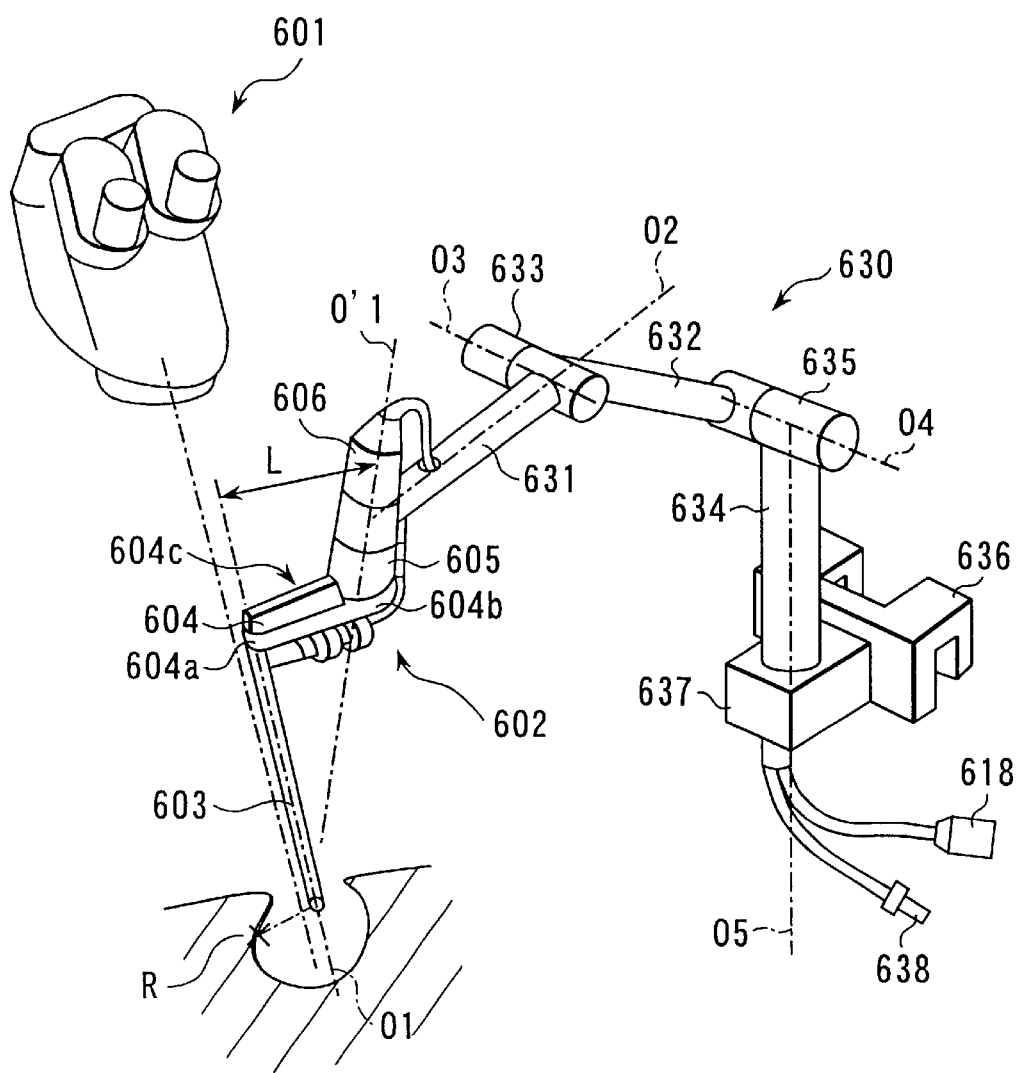
FIG. 56 is a general view of a surgical system using a rigid scope in combination with an operating microscope according to an eighteenth embodiment.

FIG. 56 shows a general configuration of a rigid scope system. The present embodiment is related mainly to an arm-type stand 630 for fixedly locating the rigid scope 602 in the operator's desired angular position.

The arm-type stand 630 for holding the rigid scope 602 comprises a first arm 631 that can be connected to the grip portion 605 of the rigid scope 602. The first arm 631 is connected to a second arm 632 by means of a connecting portion 633 for rotation around axes O2 and O3. Likewise, the second arm 632 is connected to a third arm 634 by means of a connecting portion 635 for rotation around an axis O4, and the third arm 634 is connected to a stand holder 636 by means of a connecting portion 637 for rotation around an axis O5.

The axis O2 is the center line of the first arm 631 that extends at right angles to a reflected light axis O1' (mentioned later) of the rigid scope 602, and the axis O3 extends at right angles to the axis O2. The axis O4 extends at right angles to the center line of the second arm 632, while the axis O5 extends at right angles to the axis O4.

The third arm 634 is supported vertically on the stand holder 636 and connected thereto for up-and-down motion. The holder 636 can be attached integrally to a side rail of an operating table (not shown).

Each of the connecting portions 633, 635 and 637 has an electromagnetic lock (brake, not shown) therein. The rotation around each of the axes O2 to O5 can be allowed by turning on an input switch (not shown) on the distal end of the first arm 631, for example, and it can be prohibited by turning off the input switch.

All of the first to third arms 631, 632 and 634 have a hollow structure. The cable 618 of the TV camera 606, an arm light guide 638 (mentioned later), etc. are passed through the respective bores of these arms. The cable 618 and the guide 638 are exposed downward to the outside from the lower surface of the connecting portion 637. The cable 618 and the arm light guide 638, like the ones according to the sixteenth embodiment, can be connected to a drive unit and a light source unit (not shown).

The construction of the rigid scope 602 will now be described in detail with reference to FIG. 57. In FIG. 57, numeral 640 denotes a mirror that is fixed in the first bent portion 604a of the coupling portion 604. The mirror 640 serves to bend a luminous flux, guided by the insert portion 603, at about 90° to the longitudinal direction of the insert portion 603. A relay optical system 641 is fixed in the coupling portion 604. Located in the middle of the coupling portion 604 is a mirror 642, which bends the luminous flux guided by the optical system 641 and guides it to the imaging lens 616. The mirror 642 is fixed in the second bent portion 604b of the coupling portion 604 in a manner such that an extension of the reflected light axis O1' crosses the optical axis O1 of the relay optical system 611, which is substantially in line with the central axis of the insert portion 603, in the vicinity of the objective lens 609. The reflected light axis O1' is substantially in line with the central axis of the grip portion 605.

The insert portion 603 is provided with an internal light guide 643, which, in conjunction with the illuminating lens 620, constitutes an illumination optical system. One end of the guide 643 is connected optically to the lens 620. The rear end portion of the guide 643 is led out in the same direction as the bending direction of the first bent portion 604a in a manner such that it is attached integrally to a light guide mouthpiece 644 on the rear end of the insert portion 603 by means of a sheathing 645. A connecting portion 646 is provided on the other end of the internal light guide 643. Further, the guide 643 can be fixed to the underside of the coupling portion 604 by means of hooks 647.

A connecting portion 648 is provided on the rear end portion of the grip portion 605. The connecting portion 648 engages a mounting portion 649 on the first arm 631 of the arm-type stand 630, and is positioned by being fixed to the arm 631 by means of a so-called click mechanism that includes a groove portion 650 and a fixing ball 651. Thus, the rigid scope 602 can be attached integrally to the stand 630. The TV camera 606 can be also attached integrally to the first arm 631 of the stand 630 so that its image-pickup device 617 is located in the imaging position of the imaging lens 616.

The connecting portion 648 of the grip portion 605 is provided with a bearing portion 652 that engages a flange 653. The bearing portion 652 constitutes a rotation mechanism portion 654 for holding the coupling portion 604 for rotation around the axis O1'.

As mentioned before, moreover, the arm light guide 638 is incorporated in the arms that constitute the arm-type stand 630. One end of the guide 638 is fixed by means of a light guide mouthpiece 656 at the distal end of the first arm 631. The mouthpiece 656 has a mounting screw portion 657 that engages the connecting portion 646 to be connected optically to the internal light guide 643.

Figure 58:
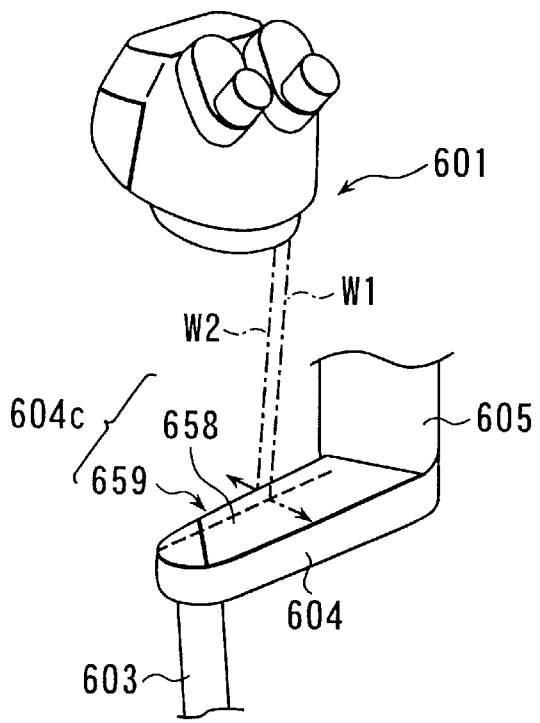
FIG. 58 is a view showing the configuration of the upper surface portion of a coupling portion of the rigid scope shown in FIG. 54.

As shown in FIG. 58, the upper surface 604c of the coupling portion 604 has slopes 658 and 659 that are inclined at right angles to their longitudinal direction.

With this arrangement, the operator observes the observational dead-angle region R of the operating microscope by means of the rigid scope 602, as in the case of the sixteenth embodiment. First, the operator holds the grip portion 605 of the rigid scope 602 and inserts the scope 602 into an affected region. Then, the operator, holding the grip portion 605, turns on the input switch (not shown) on the first arm 631. Thereupon, the electromagnetic locks in the connecting portions of the arm-type stand 630 are disengaged, so that the rotation around each of the axes O2 to O5 is allowed, and the rigid scope 602 can be operated freely. In this state, the objective lens 609 of the rigid scope 602 is located on the extension of the axis O1' that corresponds to the axis of the grip portion 605. Accordingly, the operator can insert the insert portion 603 into the affected region and locate the objective lens 609 near the observational dead-angle region R with a feeling such that the rigid scope is a conventional rod-shaped scope without the coupling portion 604 and in a manner such that the grip portion 605 and the TV camera 606 are kept at the distance L from the microscope body 601, as in the case of the sixteenth embodiment.

When the objective lens 609 is located in the observational dead-angle region R, the operator then turns off the input switch on the arm-type stand 630. Thereupon, the respective electromagnetic locks of the connecting portions are fixed, and the rigid scope 602 is fixed with the objective lens 609 kept near the region R. If the coupling portion 604 then gets into the microscopic field of the microscope body 601, as shown in FIG. 58, the illumination light from the body 601 is reflected away from the microscopic field by the slopes 658 and 659 of the coupling portion 604, as indicated by arrows W1 and W2 in FIG. 58.

The illumination light emitted from the light source (not shown) is guided to the observational dead-angle region R by means of the arm light guide 638, internal light guide 643, and illuminating lens 620. The light from the region R is transmitted through the objective lens 609, prism 610, and relay optical system 611, and then bent at about 90° by means of the mirror 640. After it is transmitted through the relay optical system 641, moreover, the light is bent in the direction of the axis O1' by means of mirror 642, and focused on the image-pickup device 617 of the TV camera 606 via the relay optical system 615 and the imaging lens 616. A video image of the observational dead-angle region R is displayed on a TV monitor (not shown) by means of the drive unit (not shown) and observed by the operator.

Figure 57:
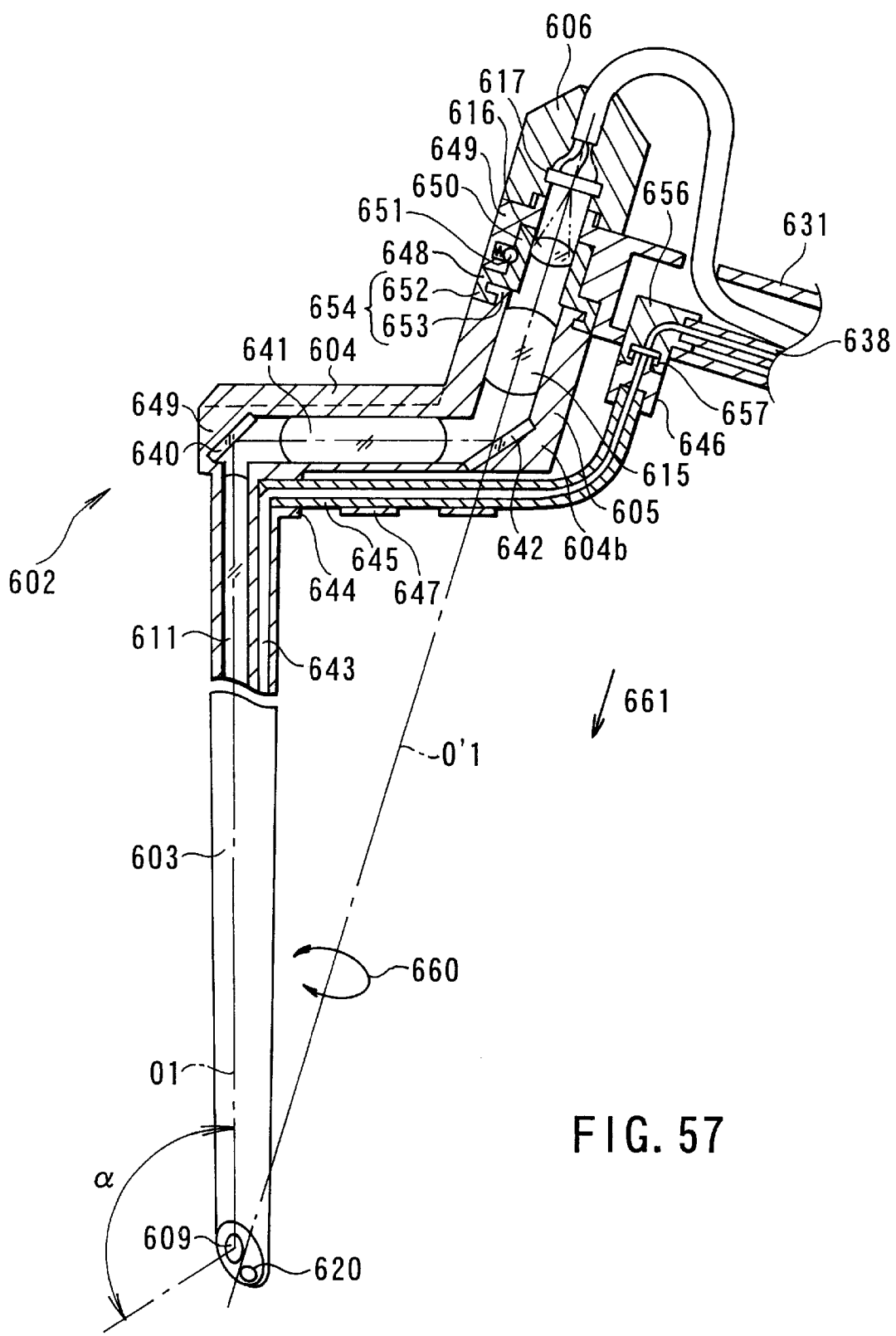
FIG. 57 is a detailed sectional view showing the construction of the rigid scope shown in FIG. 56.

Then, in changing the observational position of the rigid scope 602 from the observational dead-angle region R within a plane perpendicular to the direction of insertion of the insert portion 603, the operator operates the rotation mechanism portion 654 to rotate the coupling portion 604 in the direction of an arrow 660 shown in FIG. 57 with respect to the grip portion 605. As this is done, the internal light guide 643 is rotated integrally with the coupling portion 604 around the axis O1', since it is guided in the same direction as the bending direction of the first bent portion 604a and fixed integrally to the coupling portion 604 by means of the hooks 647. Thus, the observational position of the rigid scope 602 can be changed without changing the respective positions of the grip portion 605, TV camera 606, and arm-type stand 630.

If the operator's treatment is hindered by the grip portion 605, coupling portion 604, TV camera 606, and arm-type stand 630 during the observation of the observational dead-angle region R as it advances, as in the case of the sixteenth embodiment, the grip portion 605 is rotated reversely in the direction of the arrow 660 with respect to the coupling portion 604 by means of the rotation mechanism portion 654. Thus, the respective positions of the grip portion 605, the TV camera 606, and the arms that constitute the arm-type stand 630 with respect to the operating microscope body 601 can be changed without changing the observational position of the rigid scope 602.

Depending on the conditions of the region to be observed, moreover, the operator must change the rigid scope 602 during a surgical operation. The rigid scope may be selected among ones of which the observational angle a of the objective lens 609 to the longitudinal direction of the insert portion 603 is different or the outside diameter of the insert portion 603 varies depending on the diameter of the opening of the body cavity to be penetrated thereby. In this case, the operator first loosens the mounting screw portion 657 to remove the connecting portion 646 of the internal light guide 643 from the light guide mouthpiece 656. Further, the operator, holding the grip portion 605 in one hand and the first arm 631 in the other, pulls out the rigid scope 602 in the direction of an arrow 661 from the first arm 631. Thereupon, the groove portion 650 of the connecting portion 648 is disengaged from the pin 651 of the first arm 631, and the rigid scope 602 is removed from the first arm 631.

Subsequently, a preferred rigid scope that is different from the one described above in the observational angle α and the outside diameter of the insert portion 603 is attached to the first arm 631, reversely following the aforementioned steps of procedure, and is used in the same manner as aforesaid.

According to the present embodiment, the grip portion 605 is located at the fixed distance L from the insert portion 603 with the coupling portion 604 between them, as in the case of the sixteenth embodiment. Therefore, the surgical operation microscope body 601, grip portion 605, and TV camera 606 can avoid interfering with one another. Further, the length of projection of the grip portion 605 and the TV camera 606 within the plane of the affected region is restricted to the minimum or the distance L, and besides, the internal light guide 643 is guided in the same direction as the bending direction of the first bent portion 604a and fixed to the underside of the coupling portion 604. Accordingly, the internal light guide 643 can be securely prevented from wrongly intercepting the microscopic field during the surgical operation.

Since the objective lens 609 of the rigid scope 602 is located on the axis of the grip portion 605, moreover, the operator can adjust the observational position of the rigid scope with the same feeling of operation as that for a conventional rigid scope without the coupling portion 604, and locate the objective lens 609 more quickly and securely in the target region. Since the cable 618 of the TV camera 606 and the light guides are incorporated in the holding arm for fixedly holding the rigid scope 602 itself, furthermore, the whole rigid scope system never unduly occupies the space for the operator's surgical operation, and the efficiency of the surgical operation can be prevented from lowering.

Since the observational direction of the rigid scope 602 can be changed by only rotating the coupling portion 604 with the length L, moreover, the grip portion 605 and the TV camera 606 can be prevented from interfering with the operator's hands or body when the observational direction is changed. Since the respective positions of the grip portion 605, the TV camera 606, and the arms of the arm-type stand 630 can be changed without changing the observational position of the rigid scope 602, furthermore, change of the style can be quickly tackled with the progress of the operation, so that the efficiency of the operation is improved further.

Since the rigid scope 602 can be easily replaced with a new one during the surgical operation, moreover, an optimum rigid scope can be selected according to the progress of the operation, so that the efficiency of the operation is improved additionally.

Furthermore, the upper surface 604c of the coupling portion 604 is composed of the slopes 658 and 659. If the coupling portion 604 gets into the field of the operating microscope, therefore, the illumination light of the operating microscope is reflected to the outside of the microscopic field and prevented from entering the field. Thus, the illumination light can be prevented from dazzling in the field of the operating microscope.

Eighteenth Embodiment

A system according to an eighteenth embodiment will now be described with reference to FIGS. 59 to 61. In the description of the present embodiment to follow, like reference numerals are used to designate the same portions of the sixteenth to eighteenth embodiments, and a description of those portions is omitted.

Figure 59:
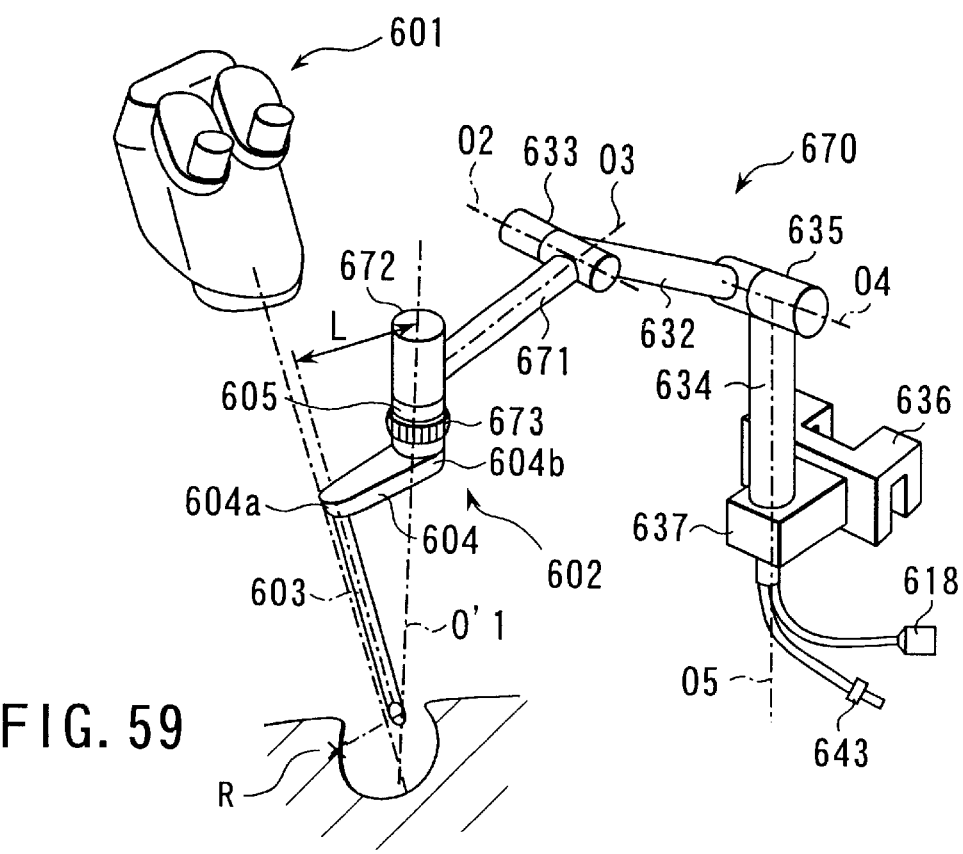
FIG. 59 is a general view of a surgical system using a rigid scope in combination with an operating microscope according to a ninth embodiment.

FIG. 59 shows a general configuration of a rigid scope system. In FIG. 59, numeral 670 denotes an arm-type stand for holding the rigid scope 602. The stand 670 is obtained by modifying only the distal end portion of the first arm 631 of the arm-type stand 630 according to the seventeenth embodiment. More specifically, the TV camera 606 is held in a distal end portion 672 of a first arm 671, and the cable 618 is housed in the arms 671, 632 and 634 without being exposed to the outside. The grip portion 605 of the rigid scope 602 is provided with a control knob 673 for changing the observational direction.

The rigid scope 602 will now be described in detail with reference to FIG. 60. An image guide 674, formed of a light guide fiber, is fixedly incorporated in the coupling portion 604. One end of the image guide 674 is connected optically to the relay optical system 611 in the insert portion 603 at the first bent portion 604a, while the other end of the guide 674 is connected optically to the relay optical system 615 in the grip portion 605 at the second bent portion 604b.

In the present embodiment, as in the seventeenth embodiment, the objective lens 609 is located in a position near the point of intersection of an extension of the optical axis O1' of the relay optical system 615, which is substantially in line with the central axis of the grip portion 605, and the optical axis O1 of the relay optical system 611, which is substantially in line with the central axis of the insert portion 603.

Figure 60:
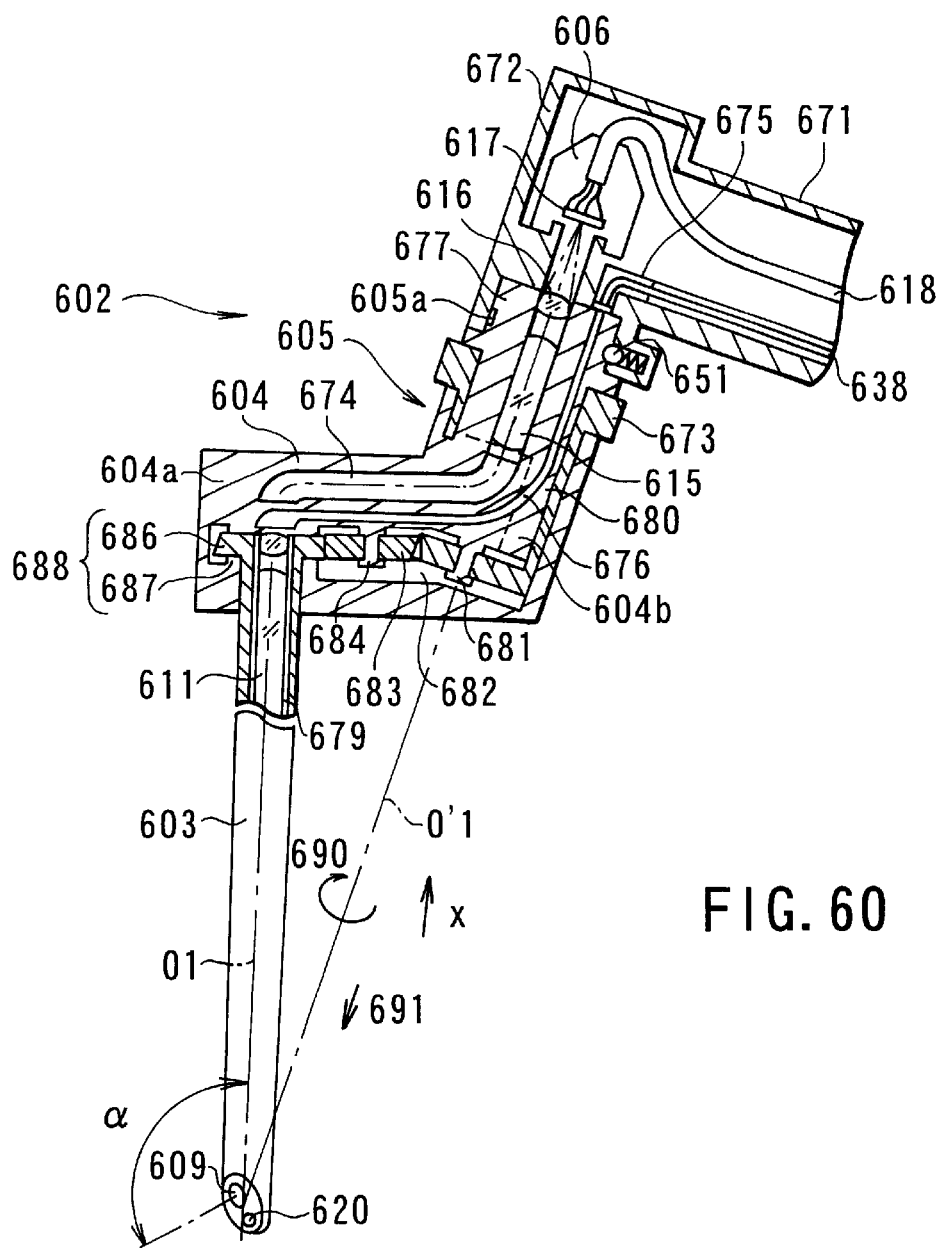
FIG. 60 is a detailed sectional view showing the construction of the rigid scope shown in FIG. 59.
Figure 61:
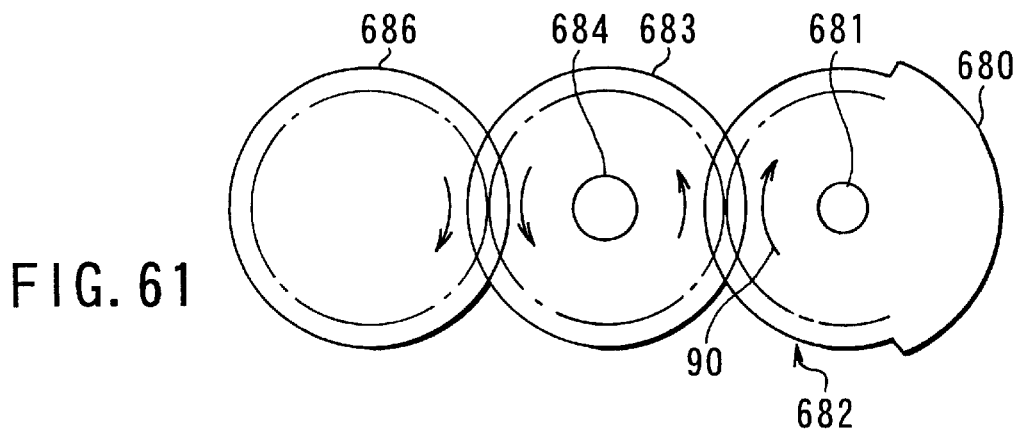
FIG. 61 is a view taken in the direction of arrow X of FIG. 60.

In FIG. 60, numeral 675 denotes a light guide fixing portion, which serves to fix one end of the arm light guide 638 in the first arm 671. A connecting light guide 676 is held in the grip portion 605 and the coupling portion 604. One end of the light guide 676 is fixed in a connecting portion 677 of the grip portion 605 so as to be connected optically to the arm light guide 638. The other end portion 678 of the connecting light guide 676 is circumferentially located so as to cover the outer periphery of the image guide 674 in the first bent portion 604a, and is fixed in the coupling portion 604 so as to be guided in the same direction as the bending direction of the first bent portion 604a.

In the insert portion 603, on the other hand, an internal light guide 679, which is connected optically to the illuminating lens 620, is circumferentially located so as to cover the outer periphery of the relay optical system 611. In the first bent portion 604a, the internal light guide 679 is circumferentially fixed so as to be connected optically to the connecting light guide 676. The illuminating lens 620, internal light guide 679, and connecting light guide 676 constitutes an illumination optical system according to the present embodiment.

Provided in the grip portion 605, moreover, is a cylindrical member 680 that is attached to the coupling portion 604 for rotation around a shaft 681. The cylindrical member 680 is coupled with the observational direction changing control knob 673 on the grip portion 605. As shown in FIG. 61, a gear 682 is provided integrally on the outer periphery of the cylindrical member 680.

In the coupling portion 604, on the other hand, a gear 680 in mesh with the gear 682 is rotatably supported on a shaft 684. In the first bent portion 604a, moreover, a gear 686 is provided in mesh with the gear 683. The gear 686, in conjunction with a bearing portion 687 in the housing of the coupling portion 604, constitutes a rotation mechanism portion 688.

With this arrangement, as in the cases of the sixteenth and seventeenth embodiments, the operator observes the observational dead-angle region R of the surgical microscope by means of the rigid scope 602. First, the electromagnetic locks in the arm-type stand 670 are disengaged with the grip portion 605 of the rigid scope 602 held in position, the objective lens of the rigid scope 602 is moved to the observational dead-angle region R, and the electromagnetic locks of the stand 670 are worked again to hold and fix j rigid scope 602. In this state, as in the case of the second embodiment, the objective lens 609 of the rigid scope 602 is located on the extension of the axis O1' that corresponds to the axis of the grip portion 605. Accordingly, the operator can position the rigid scope 602 with a feeling such that the rigid scope is a conventional one without the coupling portion 604.

Illumination light emitted from a light source (not shown) is guided to the observational dead-angle region R by means of the arm light guide 638, connecting internal light guide 676, and illuminating lens 620. After the light from the region R is transmitted through the objective lens 609, prism 610, and relay optical system 611, it is guided to the relay optical system 615 in the grip portion 605 by means of the image guide 674 in the coupling portion 604 and focused on the image-pickup device 617 of the TV camera 606. Thereupon, a video image of the observational dead-angle region R is displayed on a TV monitor (not shown) by means of a drive unit (not shown) and observed by the operator.

Then, in changing the observational position of the rigid scope 602 from the region R, the operator turns the observational direction changing control knob 673 in the direction of an arrow 690. As the knob 673 rotates, the gear 682 also rotates in the direction of the arrow 690 around the shaft 681, so that the engaging gears 683 and 686 also rotate. Thereupon, the insert portion 603 is rotated in its central axis or the optical axis O1 by means of the rotation mechanism portion 688 that is composed of the gear 686 and the bearing portion 687, whereby the observational direction of the objective lens 609 is changed. In this state, the internal light guide 679 and the connecting light guide 676 are circumferentially connected around the relay optical system 611 that has the optical axis O1. Accordingly, there is no possibility of the light guides being pulled or the illumination light suffering a loss as the insert portion 603 rotates. Thus, the illumination light is guided to the observational region, and the observational position of the rigid scope 602 is changed without changing the respective positions of the grip portion 605, TV camera 606, arm-type stand 670, etc.

If the operator's treatment is hindered by the grip portion 605, coupling portion 604, TV camera 606, and arm-type stand 670 during the observation of the observational dead-angle region R as it advances, the aforementioned processes of operation are carried out the other way around. The rotation mechanism portion 688 is operated by means of the observational direction changing control knob 673 to change the observational direction of the objective lens 609. Thereafter, the arm-type stand 670 is operated to redirect the objective lens 609 to the observational dead-angle region R. Then, respective positions of the grip portion 605, the TV camera 606, and the arms that constitute the arm-type stand 670 are changed without moving the observational position of the rigid scope 602 from the region R.

In replacing the rigid scope 602 with one that is different in the observational angle and the outside diameter of the insert portion, as in the case of the seventeenth embodiment, the operator, holding the grip portion 605 in one hand and the first arm 671 in the other, pulls out the grip portion 605 of the rigid scope 602 in the direction of an arrow 691 from the first arm 671. Thereupon, the groove portion 650 of the connecting portion is disengaged from the pin 651 in the distal end portion 672 of the first arm 671, and the rigid scope 602 is removed from the arm-type stand 670.

Then, the rigid scope that is different in the observational angle a and the outside diameter of the insert portion 603 is attached to the first arm 631, reversely following the aforementioned steps of procedure. As this is done, the connecting light guide 676 is fixed in a position (position shown in FIG. 60) where it is connected optically to the arm light guide 638 by means of the groove portion 650 and the pin 651. The present embodiment has the following effects as well as the effects of the fifth embodiments. Since the cable 618 of the TV camera 606 and the light guides can be incorporated in the rigid scope 602 and the arm-type stand 670, the whole rigid scope system never unduly occupies the space for the operator's surgical operation, and cables can be prevented from coiling around the operator's hands during the operation of the rigid scope 602. Thus, the efficiency of the rigid scope 602 itself can be improved.

Further, the observational direction of the rigid scope 602 can be changed by operating the observational direction changing control knob 673 on the grip portion 605. Thus, the observational direction can be easily changed one-handed according to the operation of the rigid scope 602.

Since the light guides need not be attached or detached when the rigid scope is replaced during a surgical operation, the rigid scope can be changed more quickly, so that the efficiency of the surgical operation is enhanced.

According to the present embodiment, the gears are used as means for connecting the observational direction changing control knob 673 and the rotation mechanism portion 688. It is to be understood, however, that the gears may be replaced with any other suitable motion transmitting mechanism, such as a wire belt or cam mechanism, with the same result.

The present invention is not limited to the embodiments described herein. According to the description of the foregoing embodiments, systems of the following particulars and optional combinations thereof can be obtained at the least.

In short, the rigid scope according to any of the sixteenth to eighteenth embodiments, having the observational optical system and the illumination optical system therein, comprises the insert portion, grip portion, and coupling portion that couples the insert and grip portions. The coupling portion includes the first and second bent portions, and the illumination optical system is guided in the same direction as the bending direction of the first bent portion.

This rigid scope is inserted into and fixed in the affected region under surgical microscopic observation without allowing its grip portion to interfere with the body of the operating microscope. Accordingly, the TV camera, cables, etc. can be securely prevented from interfering with the microscope body or intercepting the microscopic field.

The rigid scope may be provided with a rotation mechanism portion that can hold the insert portion and/or the grip portion for rotation with respect to the coupling portion.

In this case, the rigid scope can be inserted into and fixed in the affected region under surgical microscopic observation without having its grip portion interfere with the body of the operating microscope, and the position of observation by means of the rigid scope can be changed without changing the position of the rigid scope with respect to the operating microscope body. Therefore, the operator can set the observational position (or direction) in the affected region and the respective positions of the TV camera, light guides, holding arm, etc. in his or her desired relation. Further, the rigid scope can be located optimally depending on the location of the operating microscope and the operator's treatment style and method, changes during the surgical operation can be quickly tackled, and besides, the efficiency of the surgical operation can be enhanced considerably.

Moreover, a light guide that is connected to the illumination optical system may be detachably connected near the junction between the insert portion and the coupling portion.

Furthermore, a connecting portion to which the light guide connected to the illumination optical system is detachably connected may be provided in the vicinity of the grip portion.

Preferably, the respective central axes of the grip portion and the insert portion extend substantially parallel to each other.

Preferably, moreover, the objective lens should be fixed in the insert portion near an extension of the central axis of the grip portion.

The rotation mechanism portion should preferably be provided on the grip portion or the coupling portion.

An operating portion for operating the rotation mechanism portion should preferably be provided on the grip portion.

Reflection preventing means may be provided on the grip-portion-side surface of the coupling portion. Preferably, this preventing means is formed of a slope.

The following is a description of an endoscopic surgical system in an alternative form.

Figure 72:
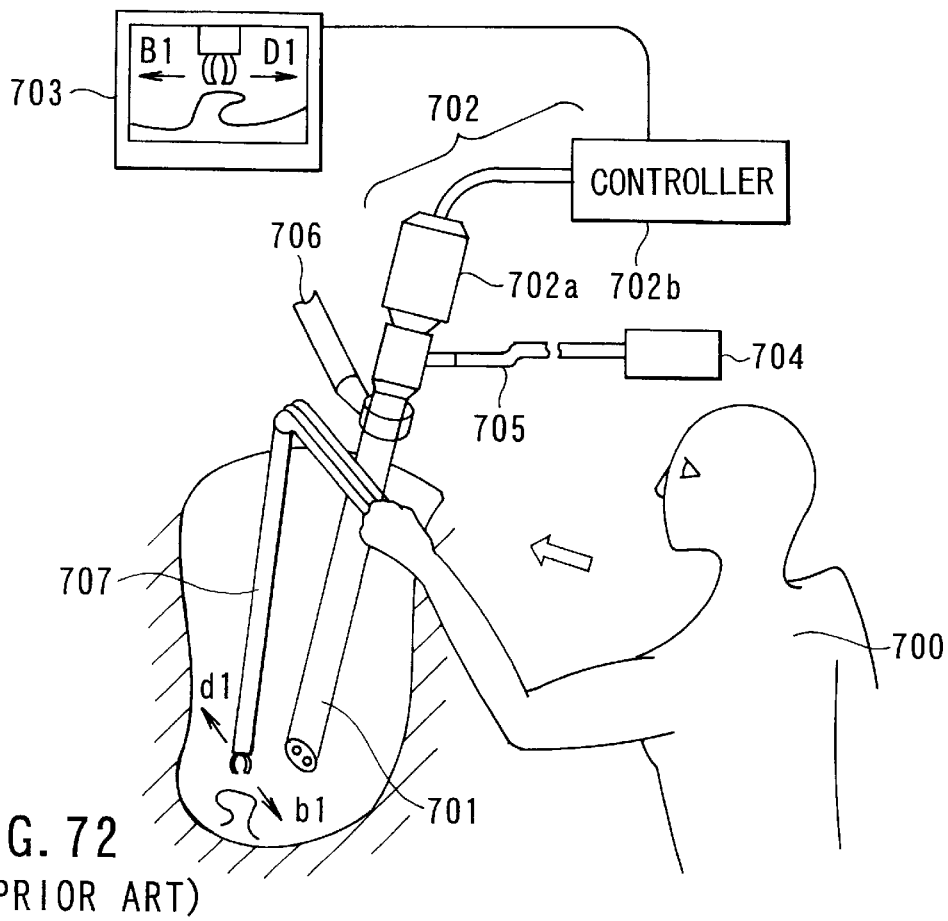
FIGS. 72 and 73 are views showing a prior art endoscopic surgical system.

FIG. 72 shows the conventional endoscopic surgical system that includes a squint-type rigid scope 701. This endoscopic surgical system comprises a TV camera system 702 formed of a TV camera head 702a and a controller 702b, monitor 703 for displaying an image picked up by means of the camera system 702, light source unit 704 for supplying illumination light to the rigid scope 701, and light guide 705. During the surgical operation, the rigid scope 701 is fixedly supported by means of a scope holder 706. The TV camera head 702a is connected to the rigid scope 701 in a manner such that the lower and upper parts of the display screen of the monitor 703 correspond to the deep side (distal end side) and the shallow side (hand side), respectively, with respect to the direction of insertion of the rigid scope 701. An operator 700 operates an instrument 707 to perform extraction of a tumor, hemostasis, etc. while watching an endoscopic observational image on the monitor 703.

Described in Jpn. Pat. Appln. KOKAI Publication No. 7-328015, for example, is a surgical manipulator that remotely operates the instrument under endoscopic observation in place of an operator. If the operator operates this surgical manipulator, a treatment manipulator is then actuated by means of an actuator, whereupon an affected region is treated. Further, the operator gets a display device on his or her head so that s/he can watch a display image thereon as s/he operates the manipulator to carry out a surgical operation. In this case, the operator's head is detected, and the observational position of the endoscope is moved correspondingly.

In FIG. 72, the rigid scope 701 is used to observe a region on the left of the operator 700, and a rigid scope image is displayed on the monitor 703. If the operator moves the instrument 707 to the right (in the direction of arrow D1) on the monitor 703 while watching the image displayed on the monitor 703 in these conditions, the actual instrument 707 is moved forward or away from the operator (in the direction of arrow d1). If the operator 700 moves the instrument 707 to the left (in the direction of arrow B1) on the monitor 703, on the other hand, the actual instrument 707 is moved toward the operator (in the direction of arrow b1).

Figure 73:
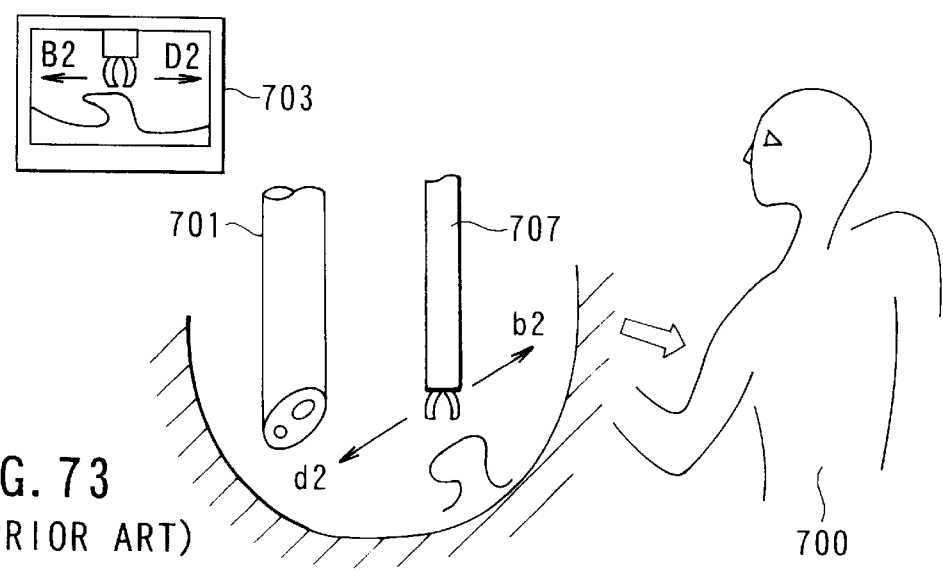

In order to move the instrument 707 on the monitor 703 to the right or left (in the direction of arrow D2 or B2) as the rigid scope in the state of FIG. 72 is turned counterclockwise for 90° to observe the operator side, as shown in FIG. 73, the operator 700 is expected actually to move the instrument 707 in the opposite direction when compared to the image on the monitor 703. Thus, in a surgical operation using an endoscope of which the observational direction is different from the direction of its insertion, the direction of actual movement of the instrument is not coincident with the moving direction of the instrument on the monitor. Accordingly, the operator must deliberate on the direction of the instrument to be moved while watching the monitor or confirm the moving direction by delicately moving the instrument to determine the direction in which the instrument is to be moved next. Therefore, the operation time is so long that the operator is fatigued inevitably. The operator can solve this problem by shifting his or her position relative to the affected region, depending on the observational direction of the endoscope, so that the operator's frontal direction is coincident with the observational direction. It is hard to attain this, however, since the instrument may interfere with a patient's body or some other surgical device.

On the other hand, the system described in Jpn. Pat. Appln. KOKAI Publication No. 7-328015 is designed to detect the operator's head in moving the endoscopic field. This system, however, is large-scaled and not easy to handle. In order to change the observational position of the endoscope, moreover, the operator's body or head must be moved. Therefore, this system is an effective measure for remote-controlled operation. Since the operating room is furnished with a lot of instruments and cables, however, the use of this system in the operating room is obstructive and narrows the range of the operator's movement. If the endoscope rotates around the course of insertion, moreover, the direction of the display image observed by the operator changes inevitably. Thus, the direction in which the master manipulator is to be moved is deviated from the direction in which the manipulator for treatment moves on the display image.

Accordingly, there is a demand for an endoscopic surgical system designed so that the manipulating direction of the instrument with respect to the operator's position is coincident with the moving direction of the instrument even if the observational direction of the endoscope is changed, whereby the operation time can be shortened, and the operator's fatigue can be eased.

FIGS. 62 to 71 show embodiments of endoscopic surgical systems that can fulfill these requirements.

Figure 62:
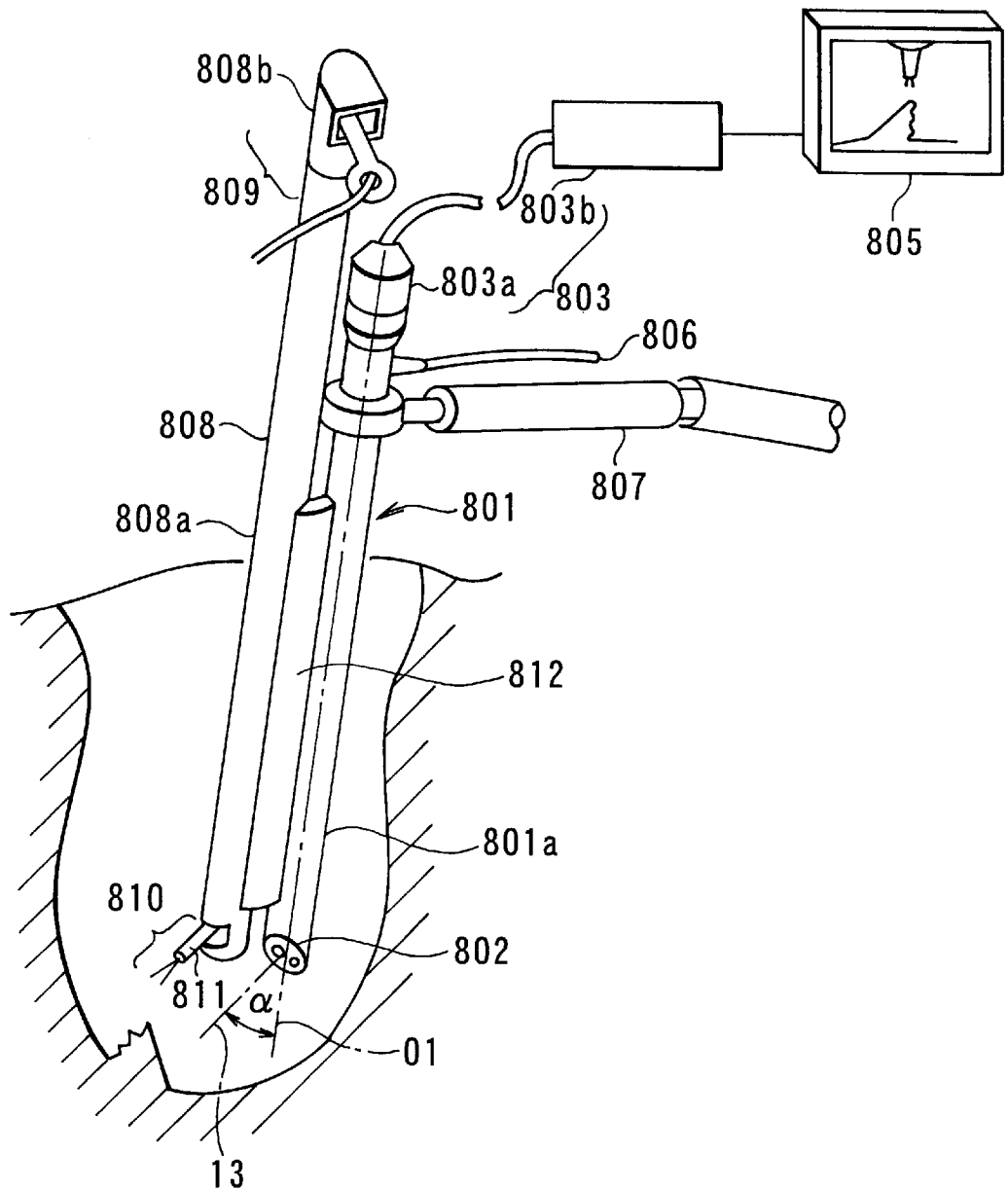
FIG. 62 is a perspective view of an endoscopic surgical system according to a twentieth embodiment of the invention.

The endoscopic surgical system shown in FIG. 62 comprises a rigid scope 801, TV system 803 formed of a TV camera head 803a and a controller 803b attached to the hand-side portion the rigid scope 801, and monitor 805. An optical axis 813 of an objective lens 802 that is provided on the distal end of the rigid scope 801 is inclined at an angle a to a central axis O1 of an insert portion 801a of the rigid scope 801. An observational image that is obtained through the objective lens 802 is picked up by means of an image-pickup device (not shown) of the TV camera head 803a through the medium of a relay optical system and an imaging optical system (not shown). The TV camera head 803a causes the controller 803b to display the observational image on the monitor 805. In FIG. 62, numeral 806 denotes a light guide that is connected to a light source unit (not shown) for supplying illumination light to the field of the rigid scope 801. The TV camera head 803 is connected to the rigid scope 801 in a manner such that the lower and upper parts of the display image of the monitor 805 correspond to the deep side (distal end side) and the shallow side (hand side), respectively, with respect to the direction of insertion of the rigid scope 801.

In FIG. 62, numeral 807 denotes a flexible scope holder for supporting the rigid scope 801. It is fixed to a bedside stay (not shown). The scope holder 807 supports the rigid scope 801 for rocking motion around the central axis O1. In FIG. 62, numeral 808 denotes an instrument 808. The instrument 808 is fixed integrally to the insert portion 801a of the rigid scope 801 by means of a connecting member 812. The instrument 808 includes an input portion 809 for the operator's manipulation and an output portion 810 that operates in response to the manipulation of the input portion 809. Further, the instrument 808 is fitted with a bipolar probe 811 that is adapted to arrest bleeding or coagulate blood in an affected region when a high-frequency current is supplied across electrodes. The instrument 808 is connected to the rigid scope 801 in a positional relation such that the output portion 810 extends along the optical axis 813 of the scope 801 to ensure image-pickup operation by means of the scope 801 at all times.

Figure 63:
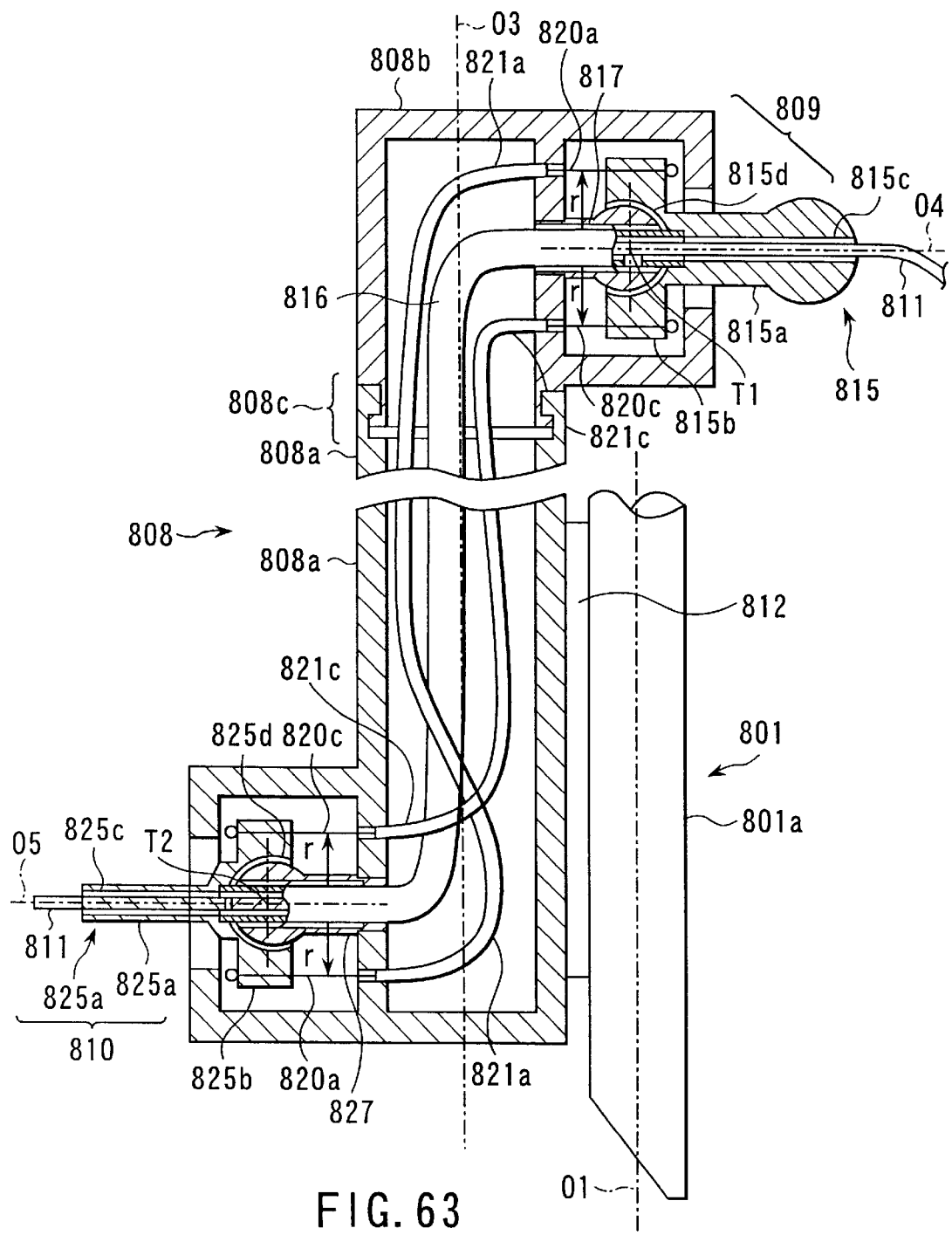
FIG. 63 is a sectional view of an instrument constituting the endoscopic surgical system of FIG. 62.
Figure 64:
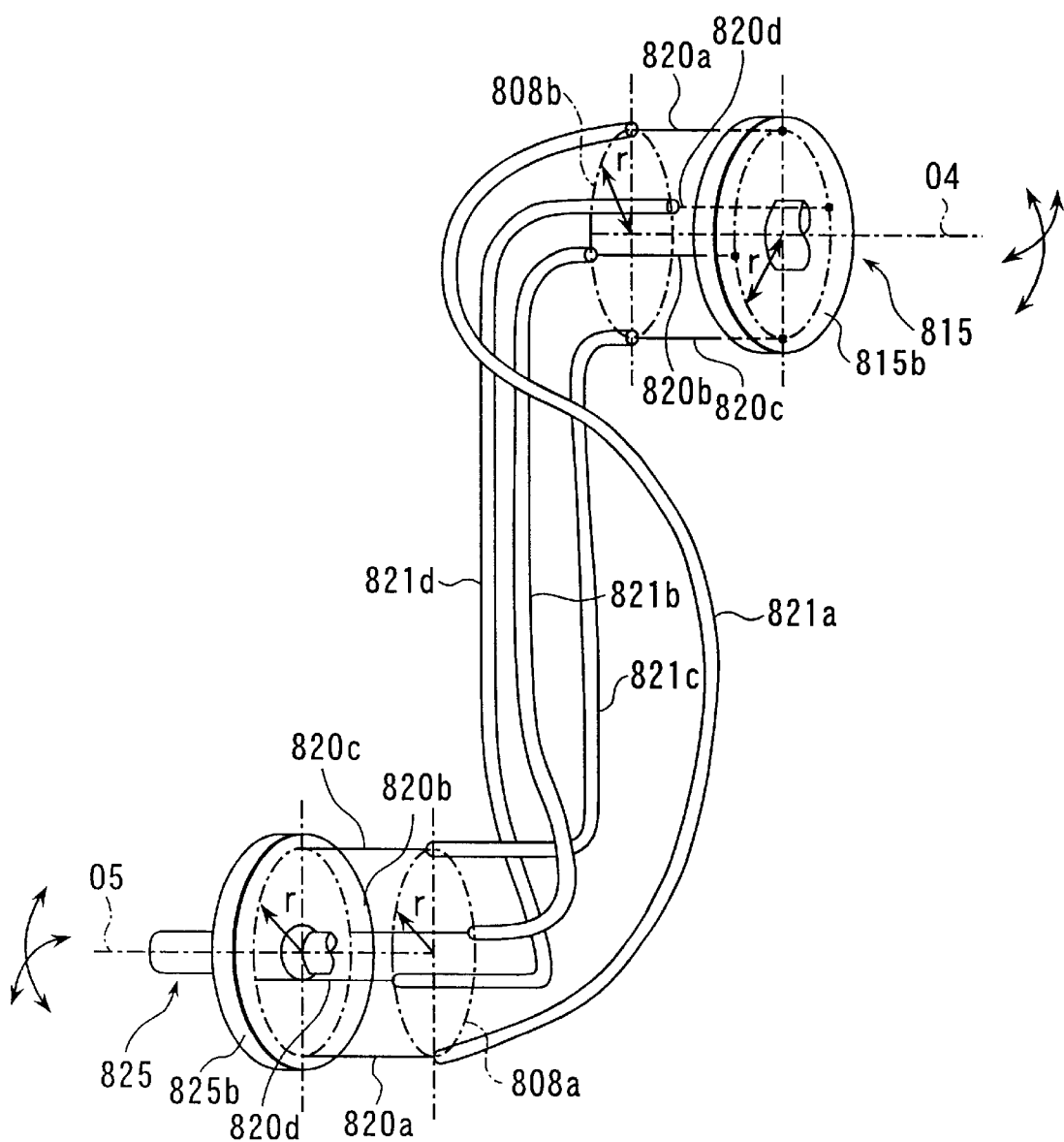
FIG. 64 is a conceptual diagram for illustrating wire-type transmission means of the instrument.

FIGS. 63 and 64 show a specific configuration of the instrument 808. As shown in FIG. 63, the instrument 808 includes a lower chassis 808a connected integrally to the insert portion 801a of the rigid scope 801 by means of the connecting member 812, upper chassis 808b rockably connected to the lower chassis 808a, and a joint 808c that connects the lower and upper chassis 808a and 808b. The upper chassis 808b can rock around an axis O3 that extends substantially parallel to the central axis O1 of the insert portion 801a of the rigid scope 801.

The input portion 809 is provided with a hollow input lever 815. The lever 815 includes a small-diameter grip portion 815a on the hand side (operator side) and a disk-shaped displacement portion 815b on the distal end side. The input lever 815 is formed having a narrow hole 815c and a recess 815d in the form of a spherical depression, located successively from the hand side in the order named. The bipolar probe 811 is inserted in the hole 815c. One end of a flexible tube 816, which has an inside diameter equal to the diameter of the hole 815c, is connected to the terminal end of the hole 815c (or the boundary between the hole 815c and the recess 815d). The bipolar probe 811 is inserted for axial movement in the tube 816. One end of an upper support shaft 817 is fixed integrally to the upper chassis 808b. The other end of the shaft 817, having a spherical shape, is fitted in the recess 815d of the input lever 815, thereby supporting the distal end side of the lever 815 so that the lever 815 can tilt around its central portion T1. The upper support shaft 817 has a hollow structure that is penetrated by the tube 816.

As is also shown in FIG. 64, one end of each of four wires 820a to 820d is fixed to the displacement portion 815b of the input lever 815. The wires 820a to 820d are fixedly arranged at angular spaces of 900 on the circumference of a circle with a radius r around the axis O4 that passes through the central portion T1. On the other hand, one end of each of four hollow flexible hoses 821a to 821d is connected to that part of the upper chassis 808b which faces the displacement portion 815b. The positions where the hoses 821a to 821d are connected correspond to the four positions where the wires 820a to 820d are fixed, respectively. The wires 820a to 820d are passed for axial movement in their corresponding hoses 821a to 821d.

The output portion 810 is provided with a hollow output lever 825. The lever 825 includes a small-diameter portion 825a on the distal end side (affected region side) and a disk-shaped displacement portion 825b on the side farther from the affected region. The output lever 825 is formed having a narrow hole 825c and a recess 825d in the form of a spherical depression, located successively from the affected region side in the order named. The bipolar probe 811 is inserted in the hole 825c. The flexible tube 816, which has the inside diameter equal to the diameter of the hole 825c, is connected to the terminal end of the hole 825c (or the boundary between the hole 825c and the recess 825d).

One end of a lower support shaft 827 is fixed integrally to the lower chassis 808a. The other end of the shaft 827, having a spherical shape, is fitted in the recess 825d of the output lever 825, thereby supporting the lever 825 so that the lever 825 can tilt around its central portion T2. The lower support shaft 827 has a hollow structure that is penetrated by the tube 816.

The respective other ends of the four wires 820a to 820d are fixed to the displacement portion 825b of the output lever 825. The wires 820a to 820d are fixedly arranged at angular spaces of 900 on the circumference of a circle with the radius r around an axis O4 that passes through the central portion T1. Further, the respective other ends of the hoses 821a to 821d are connected to that part of the lower chassis 808a which faces the displacement portion 825b. The positions where the other ends of the hoses 821a to 821d are connected correspond to the four positions where the wires 820a to 820d are fixed, respectively. As shown in FIG. 64, in this case, the wires 820a to 820d and the hoses 821a to 821d are fixed to the displacement portion 825b and the lower chassis 808a in a manner such that the arrangement around the axis O4 on the side of the input portion 809 is rotated for 180° to realize the arrangement around the axis O5.

The following is a description of the operation of the endoscopic surgical system constructed in this manner.

Figure 65:
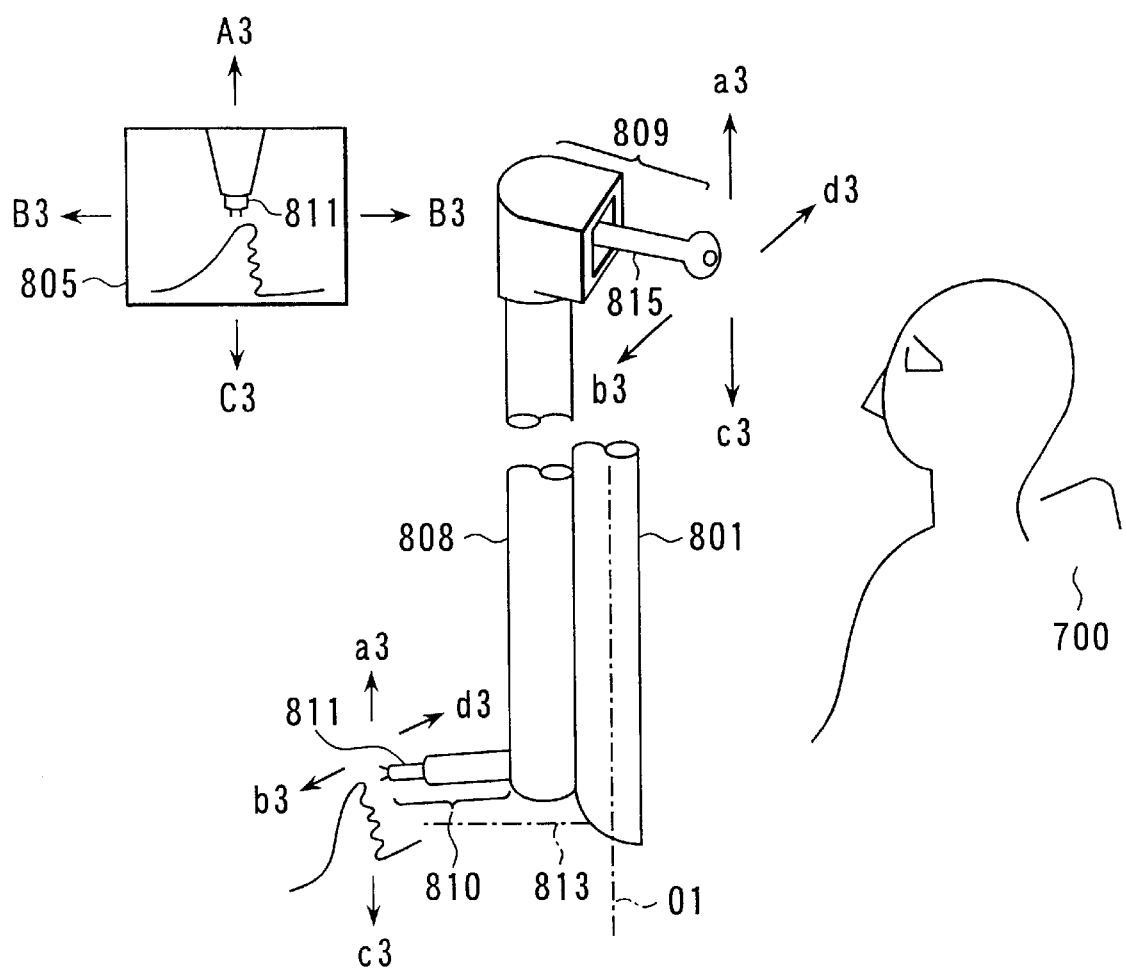
FIG. 65 is a perspective view showing a first operation mode of the endoscopic surgical system of FIG. 62.

When the rigid scope 801 is directed forward from the operator side, the observational image that is picked up by means of the scope 801 and the TV camera system 803 is displayed on the TV monitor 805, as shown in FIG. 65.

The bipolar probe 811 can be actually moved in the directions of arrows A3, B3, C3 and D3 on the screen of the monitor 805 by correspondingly tilting the input lever 815 in the directions of arrows a3, b3, c3 and d3. For example, the probe 811 can be moved to the right on the monitor 805 by tilting the lever 815 to the right. Thus, it is necessary only that the input lever 815 be tilted in a desired direction with reference to the image on the monitor 805.

In moving the distal end of the bipolar probe 811 in the direction of arrow A3 (or upward) on the monitor 805, for example, the input lever 815 is moved in the direction of arrow a3 (or upward). Thereupon, the lever 815 tilts around the central portion T1 with respect to the upper support shaft 817, so that the wire 820c is pulled to the hand side, while the wire 820a is pushed out to the distal end side (or loosens). The pushed wire 820a advances in the hose 821a, thereby causing the output lever 825 to tilt in the direction of arrow a3 around the central portion T2. Thus, the distal end of the bipolar probe 811 moves in the direction of arrow A3 on the monitor 805. For other directions, the system operates in the same manner. More specifically, if the input lever 815 is moved in the direction of arrow b3 (or to the left), the output lever 825 tilts in the direction of arrow b3, and the bipolar probe 811 moves in the direction of arrow B3 on the monitor 805. If the input lever 815 is moved in the direction of arrow c3 (or downward), the output lever 825 tilts in the direction of arrow c3, and the probe 811 moves in the direction of arrow C3 on the monitor 805. If the input lever 815 is moved in the direction of arrow d3 (or to the right), the output lever 825 tilts in the direction of arrow d3, and the probe 811 moves in the direction of arrow D3 on the monitor 805. Moreover, the operator 700 can advance or retreat the bipolar probe 811 to a target region by moving it toward or away from the input lever 815. As this is done, the probe 811 advances or retreats in the tube 816 so that it projects or recedes from the distal end of the output lever 825.

Figure 66:
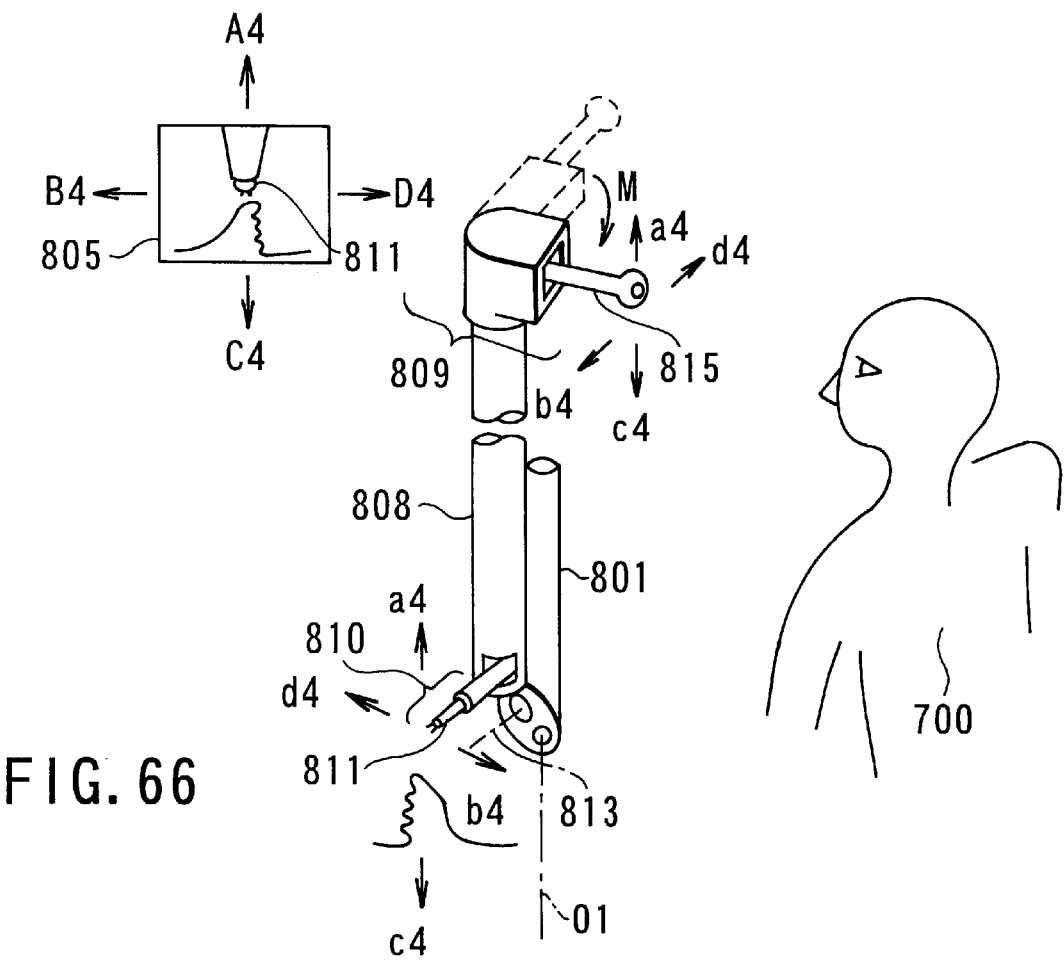
FIG. 66 is a perspective view showing a second operation mode of the endoscopic surgical system of FIG. 62.

The following is a description of the operation of the instrument 808 for the case where the rigid scope 801 is rotated counterclockwise for 90° around the axis O1 with respect to the operator 700 (case where the operator's left-hand side is observed, see FIG. 66).

If the rigid scope 801 is rotated counterclockwise for 90°, as shown in FIG. 66, the instrument 808 also rotates counterclockwise for 90° in one with the scope 801. Since the position of the operator 700 relative to an affected region never changes during a surgical operation, however, the operator 700 can restore the input lever 815 to be operated to the position right in front of him or her by rotating the upper chassis 808b for 90° in the direction of arrow M with respect to the lower chassis 808a. Thus, the output lever 825 is deviated at 90° from the input lever 815. Even in this case, however, the optical axis 813 of the rigid scope 801 and the output portion 810 of the instrument 808 are already moved integrally with each other, so that the relation shown in FIG. 65 is maintained between the moving direction of the output lever 825 of the instrument 808 on the monitor 805 and the manipulating direction of the input lever 815. Thus, the output lever 825 or the bipolar probe 811 can be appropriately moved by tilting the input lever 815 in a desired direction to move the instrument 808 on the monitor 805, only if the monitor 805 is located right in front of the operator 700 and if the input lever 815 of the instrument 808 is directed frontally (or toward the operator) as it is used.

According to the rigid scope system described above, change of the observational direction of the rigid scope 801 is transmitted mechanically to the instrument 808 to change the direction of the output with respect to the input with the scope 801 and the instrument 808 connected integrally with each other. Therefore, the construction of the system is simple and never hinders surgical operations. Since the manipulation of the input portion 809 is transmitted to the output portion 810 by means of the flexible wires and hoses, moreover, the system can enjoy a simple configuration without requiring use of any complicated mechanisms.

According to the present embodiment, the instrument 808 is fixed integrally to the insert portion 801a of the rigid scope 801. Alternatively, however, it may be fitted on the insert portion 801a of the rigid scope 801, as in the case of the sheathing of a conventional endoscope, or may be formed having a bipolar probe or the like inserted therein, as in the case of the present embodiment.

Figure 67:
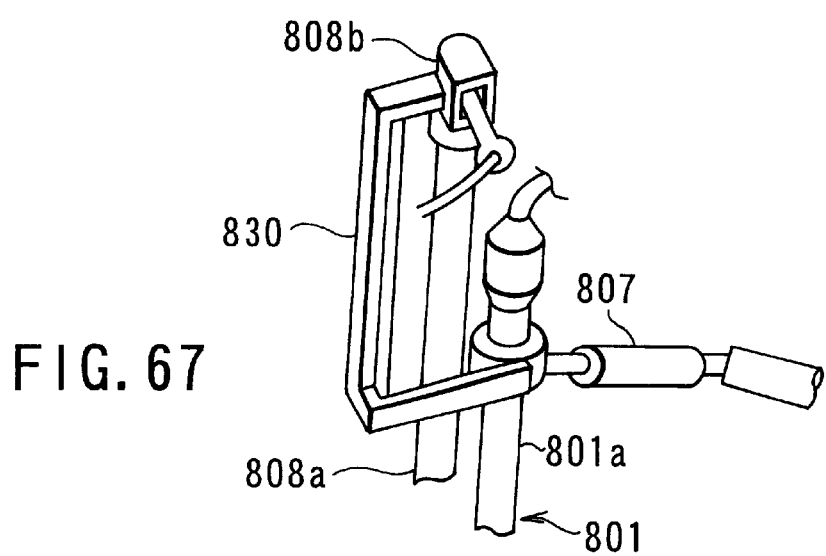
FIG. 67 is a perspective view showing a modification of the endoscopic surgical system of FIG. 62.

FIG. 67 shows a modification. In this modification, the scope holder 807 is fixed mechanically to the upper chassis 808b by means of a rotation regulating member 830. According to this arrangement, the input portion 809 never fails to be situated right in front of the operator if the rigid scope 801 is rotated around the axis O1. Thus, the operation time can be shortened.

Figure 68:
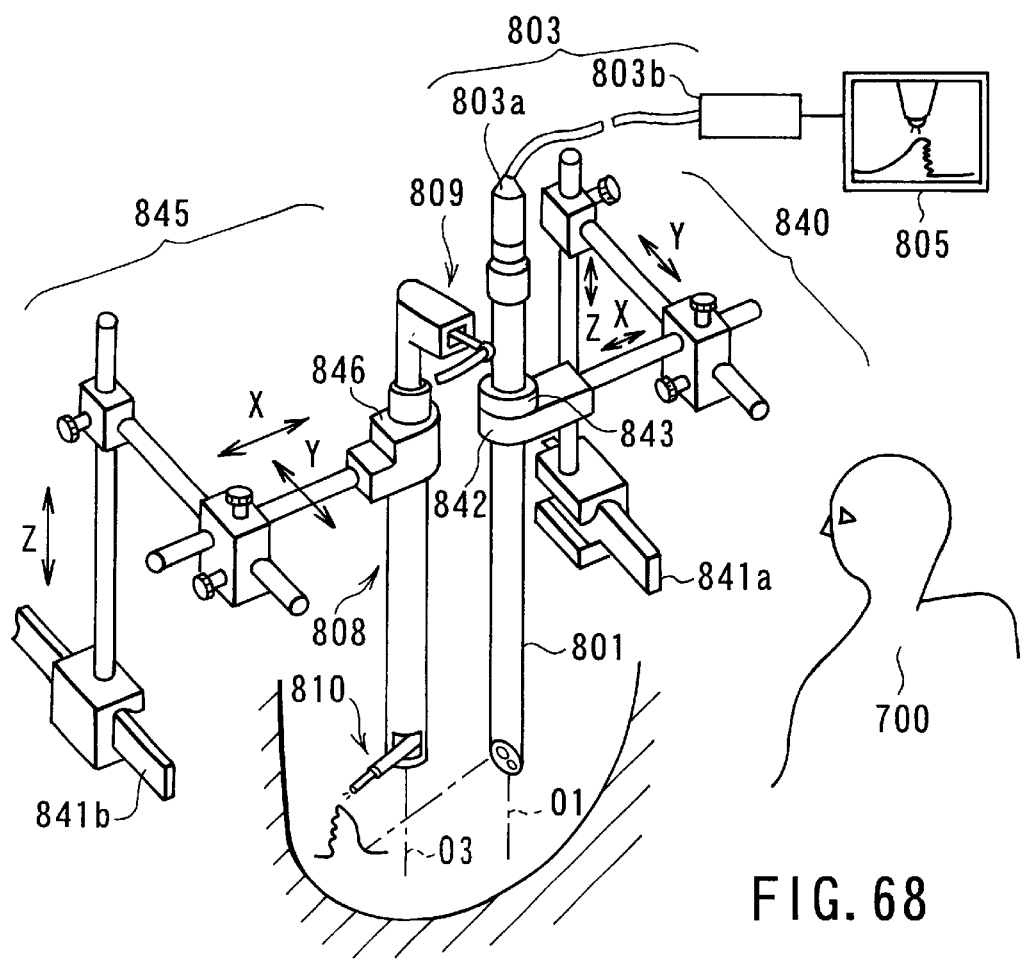
FIG. 68 is a perspective view of an endoscopic surgical system according to a twenty-first embodiment of the invention.
Figure 69:
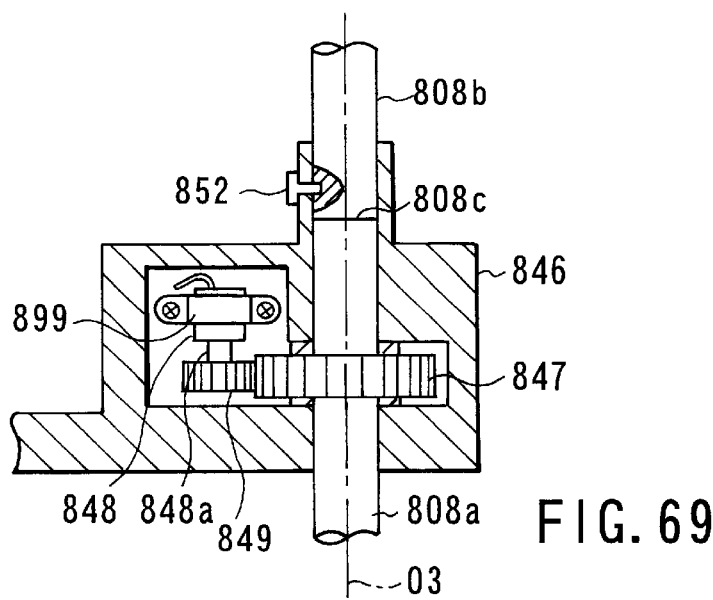
FIG. 69 is a sectional view of an instrument connecting member of the endoscopic surgical system of FIG. 68.
Figure 70:
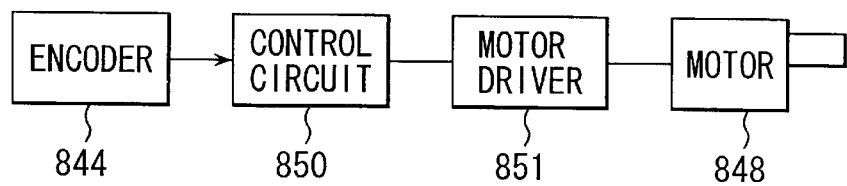
FIG. 70 is a block diagram of an electric control system for the endoscopic surgical system of FIG. 68.

FIGS. 68 to 70 show another embodiment. In the description of the present embodiment to follow, like reference numerals are used to designate those components which are common to the present embodiment and the embodiment shown in FIGS. 62 to 67, and a description of those portions is omitted.

As shown in FIG. 68, an endoscopic surgical system according to the present embodiment comprises a scope holder 840 that supports the rigid scope 801 for sliding motion in X-, Y-, and Z-axis directions. The holder 840 is fixed to a bedside stay 841a. The holder 840 includes a rigid scope connecting member 842. The connecting member 842 is provided with angle detecting means 843 for detecting the rotational angle of the rigid scope 801 compared to the scope holder 840. The detecting means 843, which is formed of an encoder 844 (see FIG. 70), serves to detect the rotational angle of the insert portion 801a of the scope 801 around the central axis O1.

Further, this endoscopic surgical system comprises an instrument holder 845 that holds the instrument 808 for sliding motion in the X-, Y-, and Z-axis directions. The holder 845, which is fixed to a bedside stay 841b, includes an instrument connecting member 846 for supporting the instrument 808.

As shown in FIG. 69, the instrument connecting member 846 on the distal end portion of the instrument holder 845 includes a gear 847 that is fixed to the lower chassis 808a of the instrument 808 in a nonrotatable manner. The gear 847, along with the connecting member 846, restrains the lower chassis 808a from moving along the axis O3 and holds it for rocking motion around the axis O3 at the joint 808c. On the other hand, the upper chassis 808b is restrained from rocking around the axis O3 by means of a pin 852 that is attached to the connecting member 846.

The instrument connecting member 846 is provided with a motor 848 that is fixed to a holding member 899. A gear 849 in mesh with the gear 847 is fixed coaxially to an output shaft 848a of the motor 848. The input and output portions 809 and 810 of the instrument 808 and the mechanism for transmitting their motions are constructed in the same manner as the ones according to the first embodiment.

As shown in FIG. 70, the encoder 844 that constitutes the angle detecting means 843 is connected to a control circuit 850. The circuit 850 is connected to a motor driver circuit 851 that is connected to the motor 848. In response to an input signal from the encoder 844, the control circuit 850 delivers a given signal to the driver circuit 851 according to predetermined conditions, in order to rock the instrument 808 around the axis O3 in the same direction and at the same angle as the rotation of the rigid scope 801 around the central axis O1.

The following is a description of the operation of the endoscopic surgical system constructed in this manner.

If the rigid scope 801 is rotated around the axis O1, the rotational angle of the rigid scope 801 compared to the rigid scope connecting member 842 is detected by means of the encoder 844 of the angle detecting means 843, and angle information is delivered to the control circuit 850. Based on this angle information, the control circuit 850 computes the rotational angle of the rigid scope 801, and delivers a signal to the motor driver circuit 851 to rotate the instrument 808 for the same angle. In response to this input signal, the driver circuit 851 causes the motor 848 to rotate for a required amount. The rotation of the motor 848 is transmitted to the lower chassis 808a with the gear 847 in mesh with the gear 849 that is fixed coaxially to the output shaft 848a, whereupon the chassis 808a rotates for the same angle as the rigid scope 801. Thus, the observational direction of the scope 801 and the direction of the output portion 810 of the instrument 808 have the same relation as in the embodiment shown in FIGS. 62 to 67. In this state, the upper chassis 808b is prevented from rotating with respective to the instrument connecting member 846 by the agency of the pin 852. Therefore, the position of the input portion 809 compared to the operator 700 never changes. Accordingly, the direction of the operator's manipulation of the instrument 808 can be made to coincide with the moving direction of the instrument 808 on the monitor 805. If the output portion 810 of the instrument 808 is deviated from the range of observation as the rigid scope 801 rotates around the central axis O1, the instrument 808 is moved in the X-, Y-, and Z-axis directions for adjustment by means of the instrument holder 845.

As described above, the present embodiment, unlike the embodiment shown in FIGS. 62 to 67, is designed so that the rotation of the rigid scope 801 around the direction of insertion is detected electrically, and the output portion 810 of the instrument 808 is rotated electrically. Therefore, the scope 801 and the instrument 808 can be held separately from each other, so that they can be inserted from different directions into different positions, depending on the conditions of the surgical operation. Thus, the system of the present embodiment can cope with a wide variety of styles of surgical operations.

According to the present embodiment, moreover, the rotation of the rigid scope 801 is detected by means of the encoder 844. Alternatively, however, it may be detected by means of conventional optical position detecting means, which is designed so that an illuminant is connected to the rigid scope 801, its image is picked up by means of image-pickup means (TV camera), and the position and rotational angle of the rigid scope are computed in accordance with the resulting image-pickup signal. Thus, the position detection can be effected even without the use of any scope holder.

Figure 71:
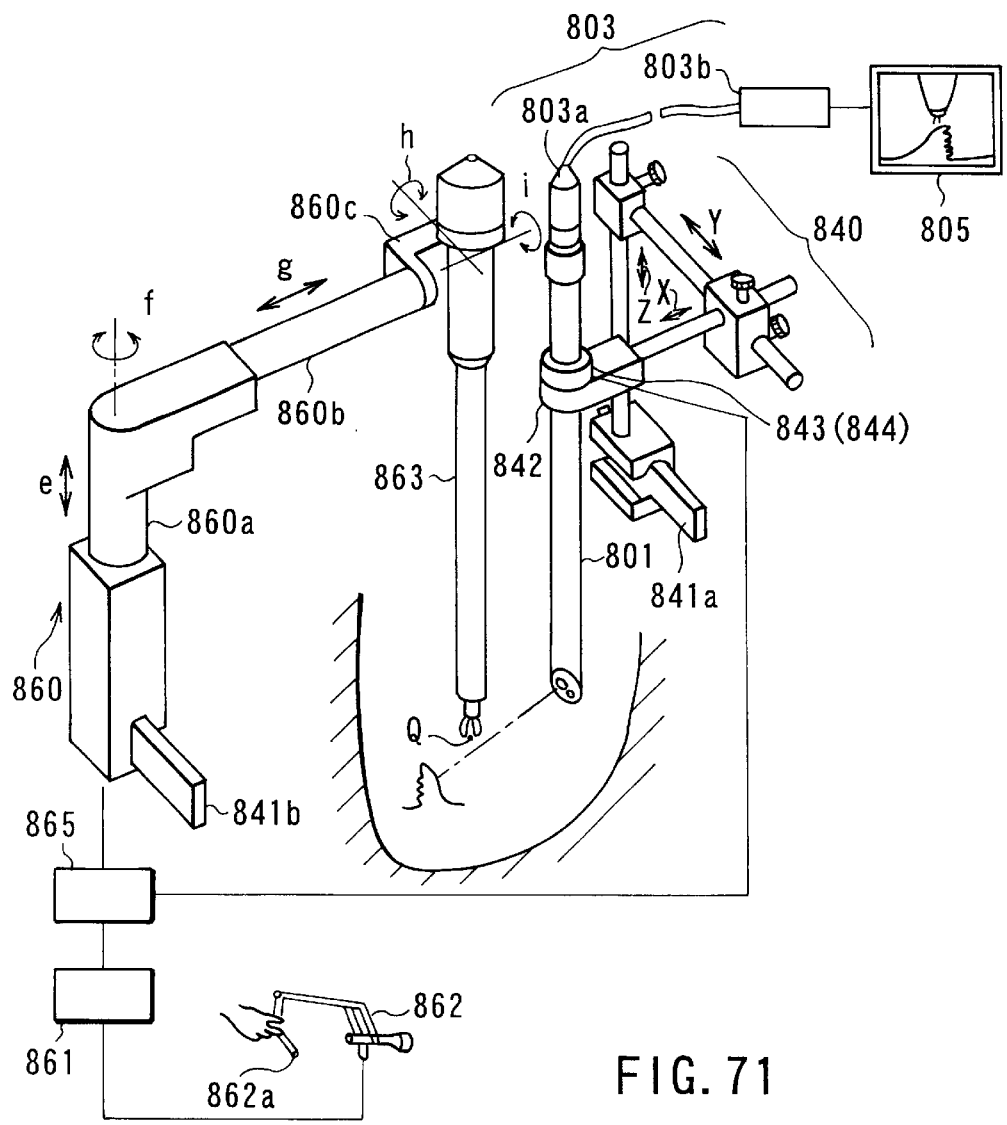
FIG. 71 is a perspective view of an endoscopic surgical system according to a twenty-second embodiment of the invention.

FIG. 71 shows still another embodiment. The rigid scope 801, TV camera system 803, monitor 805, scope holder 840, and rotational angle detecting means for detecting the position of the rigid scope 801 with respect to the holder 840, according to the present embodiment, are constructed in the same manner as the ones according to the foregoing embodiment, so that a description of those components is omitted. The following is a description of an instrument 863, a component of an alternative construction, only.

In FIG. 71, numeral 860 denotes a slave manipulator (hereinafter referred to as treatment manipulator) that has the instrument 863 fixed on its distal end and is attached to the bedside stay 841b. The treatment manipulator 860 is composed of a first operating arm 860a for use as a support mechanism movable in the vertical direction and turning direction, a second operating arm 860b attached to the first arm 860a and movable in the horizontal direction, and a joint portion 860c attached to the distal end portion of the second arm 860b. Further, the treatment manipulator 860 is connected, by means of a manipulator control device 861 and a direction changing circuit 865, to a master manipulator 862 in a region that is accessible to the operator.

As is generally known, the manipulator control device 861 receives a signal from the master manipulator 862 and delivers a driving signal to the treatment manipulator 860 such that the manipulator 860 moves in the same manner as the manipulator 862 does.

The direction changing circuit 865 is connected with an encoder 844 that constitutes the same angle detecting means 843 as aforesaid. On receiving an input signal from the encoder 844, the circuit 865 changes a signal from the manipulator control device 861 according to a given transformation formula, and delivers a driving signal for changing the operating direction of the treatment manipulator 860, compared to the manipulation of the master manipulator 862, to the manipulator 860.

The first and second operating arms 860a and 860b of the treatment manipulator 860 have the drive structure of a manipulator of a so-called cylindrical-coordinate type, formed of vertical, turning, and horizontal operation axes e, f and g that are activated by means of actuators (not shown), such as electromagnetic motors. Alternatively, however, the operating arms may have the structure of a so-called multi-joint manipulator formed of a plurality of joint portions. The joint portion 860c is connected to the instrument 863 so that it can be actuated by means of an actuator, such as an electromagnetic motor, to tilt the instrument 863 around two axes h and i that extend at right angles to each other.

The following is a description of the operation of the endoscopic surgical system constructed in this manner.

A distal end position Q of the instrument 863 that is connected to the treatment manipulator 860 is known by means of the manipulator control device 861, based on the respective operating positions of the vertical, turning, horizontal, and tilting axes e, f, g, h and i and the geometric dimensions of the individual members. On the other hand, the position of a point of action 862a of the master manipulator 862 is obtained by computation by means of the manipulator control device 861. A signal is delivered from the control device 861 to the direction changing circuit 865 such that the instrument distal end Q moves to the position of the point of action 862a of the master manipulator 862. As in the case of the foregoing embodiment, moreover, the observational direction of the rigid scope 801 is detected by means of the encoder 844 of the angle detecting means 843 and transmitted to the direction changing circuit 865.

Based on the signal from the encoder 844, the direction changing circuit 865 computes the input signal from the manipulator control device 861 according to a previously stored computational formula, and delivers a driving signal to the treatment manipulator 860 such that the manipulating direction of the master manipulator 862 is always coincident with the moving direction of the instrument 863 on the monitor 805. Thus, the signal is delivered to the treatment manipulator 860 so that the moving direction of the distal end position Q of the instrument 863 displayed on the screen of the monitor 805 is coincident with the manipulating direction of the master manipulator 862, as in the case of the foregoing embodiment. Thereupon, the direction of the operator's manipulation of the instrument 863 is coincident with the moving direction of the instrument 863 on the monitor 805.

According to the present embodiment, as described above, the instrument 863 can be remotely manipulated by means of the master manipulator 862, so that the operator can carry out a surgical operation in any convenient position without restrictions on the location of the manipulator 862. Thus, the operator can perform the operation in a more comfortable posture.

In short, the endoscopic surgical systems described with reference to FIGS. 62 to 71 comprises an endoscope capable of observation in directions different from the direction of its insertion; image-pickup means connected to the endoscope and capable of picking up an observational image of the endoscope; display means for displaying information from the image-pickup means; an instrument including an input portion for an operator's manipulation, an output portion adapted to operate in response to the manipulation of the input portion, and operating direction changing means capable of changing the operating direction of the output portion with respect to the input portion; and control means adapted to operate the operating direction changing means as the direction of observation around the direction of insertion of the endoscope changes.

In this system, the control means drives the operating direction changing means to control the operating direction of the output portion of the instrument with respect to the direction of manipulation of the input portion, in response to vertical and horizontal shifts of an affected region on the display means caused when the endoscope rotates around the direction of insertion. The operating direction of the output portion of the instrument on the display means is controlled so that it is always coincident with the direction of actual manipulation of the input portion of the instrument. Thus, if the operator manipulates the input portion of the instrument in the same direction as the direction in which the output portion of the instrument is expected to move, while watching the display means, the output portion moves in the intended or expected direction on the display means. Accordingly, the moving direction need not be considered or confirmed during the surgical operation. In consequence, the manipulation of the instrument is easy, the operation time is shortened, and therefore, the operator's fatigue can be eased.

Preferably, the operating direction changing means includes manipulation transmitting means for transmitting the manipulation of the input portion to the output portion and a rotating portion capable of rotating the output portion around the direction of insertion of the instrument into the affected region, with respect to the input portion, and the control means includes rotation transmitting means for transmitting the rotation around the direction of insertion of the endoscope, thereby rotating the rotating portion. When the endoscope rotates around the direction of insertion, in this case, the rotation transmitting means rotates the rotating portion of the instrument. Thereupon, the output portion rotates around the direction of insertion with respect to the input portion of the instrument. In this state, the manipulation transmitting means transmits the manipulation of the input portion to the output portion, so that the operating direction of the output portion is changed with respect to the input operation.

The manipulation transmitting means may be mechanical transmitting means.

In the case where the rotation transmitting means is provided with a connecting member for connecting the endoscope and the instrument integrally to each other, the connecting member causes the instrument to rotate integrally with the rigid scope so that the rotating portion of the instrument rotates when the endoscope rotates around the direction of insertion. Thereupon, the output portion rotates in the direction of insertion with respect to the input portion of the instrument. In this state, the manipulation transmitting means transmits the manipulation of the input portion to the output portion, so that the operating direction of the output portion is changed with respect to the input operation.

Preferably, the rotation transmitting means includes rotation detecting means for detecting the rotational displacement of the endoscope in the direction of insertion with respect to a given region, drive means capable of rotating the rotating portion, and electrical control means for controlling the drive of the drive means in accordance with a signal from the rotation detecting means. In this case, the rotation of the endoscope around the direction of insertion is detected by the rotation detecting means and applied to the electrical control means. Based on this input signal, the electrical control means drives the drive means to rotate the rotating portion. Thereupon, the output portion rotates in the direction of insertion with respect to the input portion of the instrument. In this state, the manipulation transmitting means transmits the manipulation of the input portion to the output portion, so that the operating direction of the output portion is changed with respect to the input operation.

The rotation detecting means may be an encoder.

Preferably, moreover, the rotation detecting means is provided with an optical illuminant, second image-pickup means for picking up an image of the optical illuminant, and optical position detecting means including computing means for computing the rotational angle of the endoscope in accordance with a signal from the second image-pickup means.

The drive means may be a motor.

The mechanical transmitting means may be provided with a first flexible member and a second flexible member capable of being displaced relatively to the first flexible member. Preferably, the first flexible member is a wire, and the second flexible member is a hose fitted on the wire.

Further, there may be provided an endoscopic surgical system comprising an endoscope capable of lateral observation; image-pickup means connected to the endoscope and capable of picking up an observational image of the endoscope; display means for displaying information from the image-pickup means; an instrument including a master manipulator for an operator's manipulation, a slave manipulator adapted to operate in response to the manipulation, and manipulator control means for controlling the slave manipulator so that the slave manipulator operates following the master manipulator; rotation detecting means for detecting the rotational displacement of the endoscope around the direction of insertion, and manipulator operating direction changing means for controlling the operating direction of the slave manipulator in accordance with information from the manipulator control means and the rotation detecting means.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical observational system comprising:

an observational optical system which forms an optical image of an object including an affected region;

first observational means for observing the optical image;

second observational means which obtains an image showing a desired area of the object found in the optical image, the second observational means being different from the first observational means at least in terms of an observational direction or observational method;

display means for displaying the image showing the desired area obtained by the second observational means;

means for optically transmitting the image showing the desired area displayed by the display means to the observation optical system so that the image showing the desired area is superposed on the optical image of the object observed by the first observation means;

detecting means which detects a relative position of the first and second observational means in three dimensions; and means for controlling a display position of the image showing the desired area displayed on the display means in accordance with the detected relative position of the first and second observational means in three dimensions to superpose the image showing the desired area displayed on the display means on the desired area of the optical image.

2. The surgical observational system according to claim 1, wherein the second observational means comprises one of an endoscope, rigid scope and ultrasonic diagnostic apparatus.

3. A surgical observational system comprising:

an observational optical system for forming an optical image of an object including an affected region, first observational means for observing the optical image;

an indicator indicative of a desired position in the optical image;

second observational means which obtains an image including the desired position indicated by the indicator, the second observational means being different from the first observational means at least in terms of an observational direction or observational method;

display means for displaying the image including the desired position indicated by the indicator;

means for optically transmitting the image including the desired position displayed on the display means to the observational optical system so that the image including the desired position is superposed on the optical image of the object observed by the first observational means;

detecting means which detects a relative position of the first and second observational means in three dimensions; and means for controlling a display position of the image including the desired position displayed on the display means in accordance with the detected relative position of the first and second observational means in three dimensions so that the image including the desired position is superposed on the desired position of the optical image.

4. The surgical observational system according to claim 3, wherein the indicator is provided at a predetermined position of the second observational means.

5. The surgical observational system according to claim 3, wherein the second observational means comprises one of an endoscope, rigid scope and ultrasonic diagnostic apparatus.

6. The surgical observational system according to claim 5 wherein the second observational means comprises an ultrasonic diagnostic apparatus, and the indicator comprises a distal end portion of a probe of the ultrasonic diagnostic apparatus.

7. The surgical observational system according to claim further comprising:

setting means for setting a size of the image which is obtained by the second observational means, and is superposed on the desired position of the optical image, in accordance with a magnification of the optical image observed by the first observational means.

8. The surgical observational system according to claim 3, wherein the indicator comprises a cursor displayed on the optical image observed by the first observational means.

9. A surgical observational system comprising:

a first observational apparatus including a first optical system which forms an optical image of an object;

a second observational apparatus different from the first observational apparatus at least in terms of an observational direction or observational method, the second observational apparatus including an elongated member that is capable of obtaining an image showing a desired area of the object found in the optical image;

a monitor provided for the first observational apparatus that is capable of displaying the image showing the desired area obtained by the second observational apparatus;

a second optical system provided for the first observational apparatus that optically transmits the image showing the desired area to the first optical system so that the image showing the desired area obtained by the second observational apparatus is superposed on the optical image observed by the first observational apparatus;

a detector which detects a relative position of the first and second observational apparatuses in three dimensions; and a computer that is electrically connected to the monitor and to the detector, and that is capable of controlling a display position of the image showing the desired area on the monitor in accordance with a detection result of the detector such that the image showing the desired area obtained by the second observational apparatus is superposed on the desired area of the optical image observed by the first observational apparatus.

10. The surgical observational system according to claim 9, wherein the second observational apparatus comprises one of an endoscope, rigid scope and ultrasonic diagnostic apparatus.

11. The surgical observational system according to claim 9, wherein the computer sets a size of the image showing the desired area superposed on the desired area of the optical image and displayed on the monitor in accordance with a magnification of the optical image observed by the first observational apparatus.

12. A surgical observational system comprising:

a first observational apparatus including a first optical system which forms an optical image of an object;

an indicator indicative of a desired position in the optical image;

a second observational apparatus different from the first observational apparatus at least in terms of an observational direction or observational method, the second observational apparatus including an elongated member that is capable of obtaining an image including the desired position indicated by the indicator;

a monitor provided for the first observational apparatus that is capable of displaying the image showing the desired area obtained by the second observational apparatus;

a second optical system provided for the first observational apparatus that optically transmits the image including the desired position to the first optical system so that the image including the desired position obtained by the second observational apparatus is superposed on the optical image observed by the first observational system;

a detector which detects a relative position of the first and second observational apparatuses in three dimensions; and a computer that is electrically connected to the monitor and to the detector, and that is capable of controlling a display position of the image including the desired position displayed on the monitor in accordance with a detection result of the detector such that the image including the desired position obtained by the second observational apparatus is superposed on the desired position of the optical image observed by the first observational apparatus.

13. The surgical observational system according to claim 12, wherein the indicator is provided at a predetermined position of the second observational apparatus.

14. The surgical observational system according to claim 12, wherein the second observational apparatus comprises one of an endoscope, rigid scope and ultrasonic diagnostic apparatus.

15. The surgical observational system according to claim 12, wherein the second observational apparatus comprises an ultrasonic diagnostic apparatus, and the indicator comprises a distal end portion of a probe of the ultrasonic diagnostic apparatus.

16. The surgical observational system according to claim 19, wherein the computer also sets a size of the image including the desired position superposed on the desired position of the optical image and displayed on the monitor in accordance with a magnification of the optical image observed by the first observational apparatus.

17. The surgical observational system according to claim 12, wherein the indicator comprises a cursor displayed on the optical image observed by the first observational means.

18. A surgical observational system comprising:

a first observation apparatus for observing a first image of an object;

a second observation apparatus which obtains a second image which is an image showing a desired area of the object found in the first image, the second observational means being different from the first observational apparatus at least in terms of an observation direction or observational method;

a monitor provided for the first observational apparatus that is capable of displaying the second image obtained by the second observational apparatus;

an optical system provided for the first observational apparatus that optically transmits the second image displayed on the monitor so that the second image is superposed on the first image observed by the first observational apparatus;

a detector which detects a relative position of the first and second observational apparatuses in three dimensions; and a computer that is electrically connected to the monitor and to the detector, and that is capable of controlling a display position of the second image displayed on the monitor in accordance with the detected relative position of the first and second observational apparatus in three dimensions to superpose the second image on the desired area of the first image.

19. A surgical observational system comprising:

a first observational apparatus for observing a first image of an object;

an indicator indicative of a desired position in the first image;

a second observational apparatus which obtains a second image which is an image including the desired position indicated by the indicator and found in the first image, the second observational apparatus being different from the first observational apparatus at least in terms of an observational direction or observational method;

a monitor provided for the first observational apparatus that displays the second image obtained by the second observational apparatus;

an optical system provided for the first observational apparatus that optically transmits the second image displayed on the monitor so that the second image is superposed on the first image observed by the first observational apparatus;

a detector which detects a relative position of the first and second observational apparatuses in three dimensions; and a computer that is electrically connected to the monitor and to the detector, and that is capable of controlling a display position of the second image displayed on the monitor in accordance with the detected relative position of the first and second observational apparatus in three dimensions to superpose the second image on the desired area of the first image.

* * * * *